United States Patent [19]
Kogen et al.

[11] Patent Number: 5,604,256
[45] Date of Patent: Feb. 18, 1997

[54] OCTAHYDRONAPHTHALENE OXIME DERIVATIVES FOR CHOLESTEROL BIOSYNTHESIS INHIBITION

[75] Inventors: Hiroshi Kogen; Masaaki Kurabayashi; Teiichiro Koga; Toru Komai; Haruo Iwabuchi, all of Tokyo, Japan

[73] Assignee: Sankyo Company, Limited, Tokyo, Japan

[21] Appl. No.: 357,062

[22] Filed: Dec. 14, 1994

Related U.S. Application Data

[63] Continuation of Ser. No. 61,911, May 14, 1993, abandoned.

[30] Foreign Application Priority Data

May 15, 1992 [JP] Japan .................................. 4-122476

[51] Int. Cl.$^6$ ...................... A61K 31/335; C07D 319/06
[52] U.S. Cl. ...................... 514/452; 544/165; 548/204; 548/248; 549/71; 549/77; 549/366; 549/373; 549/378; 549/467; 549/494; 560/73; 560/107; 560/252
[58] Field of Search .................. 549/373; 514/452

[56] References Cited

U.S. PATENT DOCUMENTS 4,997,848  3/1991  Kurabayashi et al. .

FOREIGN PATENT DOCUMENTS 0076601  4/1983  European Pat. Off. .
0142146  5/1985  European Pat. Off. .
0314435  5/1989  European Pat. Off. .

OTHER PUBLICATIONS

Heathcock et al, "Synthesis and Biological Evaluation of a Monocyclic, Fully Functional Analogue of Compactin", J. Med. Chem., 32, 197–202, (1989).

*Primary Examiner*—Robert W. Ramsuer
*Attorney, Agent, or Firm*—Frishauf, Holtz, Goodman, Langer & Chick, P.C.

[57] ABSTRACT

Compounds of formula (I):

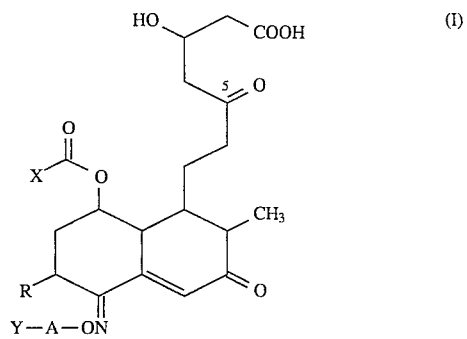

(in which: R is hydrogen, methyl or hydroxy; X is alkyl, alkenyl, cycloalkyl, aryl, aralkyl, or a heterocyclic group; A is a single bond, or an alkylene, alkenylene, alkynylene or alkadienylene group; Y is hydrogen, aryl, cycloalkyl or a heterocyclic group) have the ability to inhibit the biosynthesis of cholesterol, and can thus be used for the treatment and prophylaxis of diseases relating to high blood cholesterol levels.

9 Claims, No Drawings

OCTAHYDRONAPHTHALENE OXIME DERIVATIVES FOR CHOLESTEROL BIOSYNTHESIS INHIBITION

This application is a Continuation of application Ser. No. 08/061,911, filed May 14, 1993, now abandoned.

BACKGROUND OF THE INVENTION

The present invention relates to a series of new octahydronaphthalene oxime derivatives, which have the ability to inhibit the biosynthesis of cholesterol. The invention also provides methods and compositions using these compounds as well as processes for preparing them. A number of compounds which may be generally described as 7-[substituted 1,2,3,5,6,7,8,8a-octahydro-1-naphthyl]-3,5-dihydroxyheptanoates is known, of which the closest are thought to be those compounds having the formula (A):

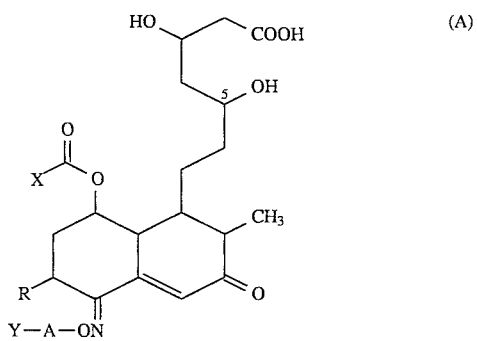

(in which A, R, X and Y are essentially as defined hereafter in relation to the compounds of the present invention). These compounds are disclosed, inter alia, in European Patent Publication No. 314 435, which also describes in greater detail than herein the development and forerunners of these types of compound. These compounds of formula (A) are believed by us to be the closest compounds to those of the present invention. These prior art compounds, like the compounds of the present invention, have the ability to inhibit the biosynthesis of cholesterol, and can thus be used for the treatment and prophylaxis of the various diseases caused by hypercholesterolemia, such as atherosclerosis and various cardiac disorders.

Other, similar, classes of compounds, which also have some resemblances to the compounds of the present invention are those compounds have been described in Japanese Patent Kokai Application, No. Sho 60-123445 (European Patent Publication No. 142 146) and Journal of Medicinal Chemistry 32, 197 (1989). They may be represented by the formulae (B) and (C):

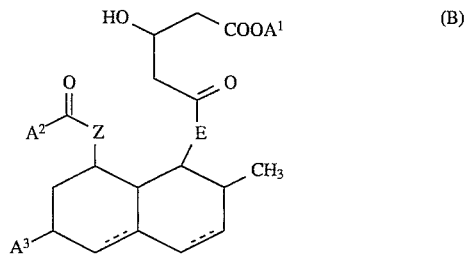

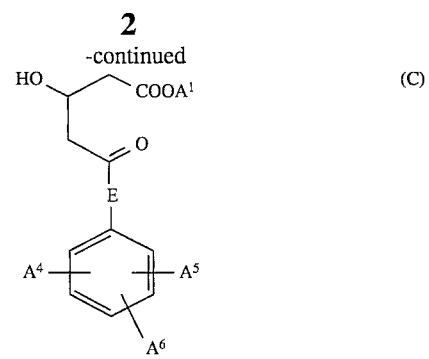

in which:
E represents a group of formula —$CH_2CH_2$—, —CH=CH— or —$(CH_2)_3$—; $A^1$ represents a hydrogen atom or a lower alkyl group; $A^2$ represents a lower alkyl group; $A^3$ represents a hydrogen atom or a methyl group; and $A^4$, $A^5$ and $A^6$, which are the same as each other or different from each other, each represents a hydrogen atom, a halogen atom, a lower alkyl group or an unsubstituted phenyl group.

Compounds corresponding to these compounds of formula (B) and (C) but having a hydroxy group at the 5-position in place of the 5-oxo group are also known. They are known to have an ability to inhibit the biosynthesis of cholesterol which is consistently greater then that of the corresponding 5-oxo compounds.

We have now surprisingly found that the 5-oxo compounds corresponding to the 5-hydroxy compounds of formula (A) have a significantly greater cholesterol biosynthesis inhibitory activity than do the 5-hydroxy compounds of formula (A).

BRIEF SUMMARY OF INVENTION

Thus the present invention provides new compounds of formula (I):

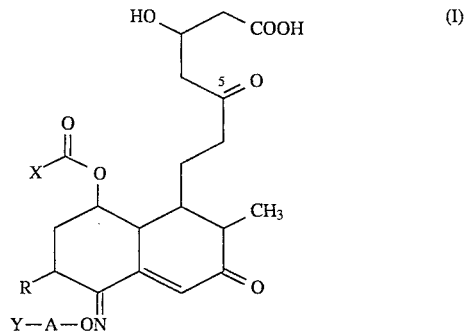

in which:
R represents a hydrogen atom, a methyl group or a hydroxy group;
X represents:
   an alkyl group having from 1 to 10 carbon atoms,
   an alkenyl group having from 3 to 10 carbon atoms,
   a cycloalkyl group having from 3 to 10 carbon atoms,
   an aryl group having from 6 to 10 carbon atoms,
   an aralkyl group in which an alkyl group having from 1 to 6 carbon atoms is substituted by at least one carbocyclic aryl group having from 6 to 10 carbon atoms, or
   a heterocyclic group having 5 or 6 ring atoms of which from 1 to 3 are hetero-atoms selected from the group consisting of nitrogen, oxygen and sulfur atoms,
said alkyl and alkenyl groups being unsubstituted or having at least one substituent selected from the group consisting of substituents A, defined below, and said cycloalkyl, aryl, aralkyl and heterocyclic groups being unsubstituted or having at least one substituent selected from the group consisting of substituents B, defined below;

A represents a single bond, an alkylene group having from 1 to 10 carbon atoms, an alkenylene group having from 3 to 10 carbon atoms, an alkynylene group having from 3 to 10 carbon atoms or an alkadienylene group having from 5 to 10 carbon atoms, said alkylene, alkenylene, alkynylene and alkadienylene groups being unsubstituted or having at least one substituent selected from the group consisting of substituents C, defined below;

Y represents:
  a hydrogen atom,
  an aryl group having from 6 to 14 carbon atoms,
  a cycloalkyl group having from 3 to 10 carbon atoms,
  a heterocyclic group having 5 or 6 ring atoms of which from 1 to 3 are hetero-atoms selected from the group consisting of nitrogen, oxygen and sulfur hetero-atoms or
  a heterocyclic group which has 5 or 6 ring atoms of which from 1 to 3 are hetero-atoms selected from the group consisting of nitrogen, oxygen and sulfur hetero-atoms and which is fused to a benzene ring,
said aryl, cycloalkyl and heterocyclic groups being unsubstituted or having at least one substituent selected from the group consisting of substituents D, defined below;

substituents A:
  halogen atoms, hydroxy groups, alkoxy groups having from 1 to 4 carbon atoms, aliphatic carboxylic acyloxy groups having from 2 to 5 carbon atoms, amino groups, carboxy groups and protected carboxy groups;

substituents B:
  halogen atoms, hydroxy groups, alkoxy groups having from 1 to 4 carbon atoms, aliphatic carboxylic acyloxy groups having from 2 to 5 carbon atoms, amino groups, carboxy groups, protected carboxy groups, alkyl groups having from 1 to 5 carbon atoms and haloalkyl groups having from 1 to 5 carbon atoms;

substituents C:
  halogen atoms, hydroxy groups, alkoxy groups having from 1 to 4 carbon atoms, aryloxy groups having from 6 to 14 carbon atoms, aralkyloxy groups, aliphatic carboxylic acyloxy groups having from 2 to 5 carbon atoms, aromatic carboxylic acyloxy groups having from 7 to 15 carbon atoms, amino groups, alkylamino groups having from 1 to 4 carbon atoms, dialkylamino groups in which each alkyl group has from 1 to 4 carbon atoms, arylamino groups having from 6 to 14 carbon atoms, diarylamino groups in which each aryl group has from 6 to 14 carbon atoms, aralkylamino groups, diaralkylamino groups, aliphatic carboxylic acylamino groups having from 2 to 5 carbon atoms, aromatic carboxylic acylamino groups having from 7 to 15 carbon atoms, carboxy groups and protected carboxy groups, wherein the aryl groups of said aryloxy, aralkyloxy, aromatic carboxylic acyloxy, arylamino, diarylamino, aralkylamino, diaralkylamino and aromatic carboxylic acylamino groups are unsubstituted or have at least one substituent selected from the group consisting of substituents E, defined below, and in which the aralkyl part of each of said aralkyloxy, aralkylamino and diaralkylamino groups is an alkyl group which has from 1 to 6 carbon atoms which is substituted by at least one aryl group having from 6 to 10 carbon atoms;

substituents D:
  halogen atoms, hydroxy groups, alkoxy groups having from 1 to 4 carbon atoms, aryloxy groups having from 6 to 14 carbon atoms, aralkyloxy groups, aliphatic carboxylic acyloxy groups having from 2 to 5 carbon atoms, aromatic carboxylic acyloxy groups having from 7 to 15 carbon atoms, mercapto groups, alkylthio groups having from 1 to 4 carbon atoms, arylthio groups having from 6 to 14 carbon atoms, aralkylthio groups, amino groups, alkylamino groups having from 1 to 4 carbon atoms, dialkylamino groups in which each alkyl group has from 1 to 4 carbon atoms, arylamino groups having from 6 to 14 carbon atoms, diarylamino groups in which each aryl group has from 6 to 14 carbon atoms, aralkylamino groups, diaralkylamino groups, aliphatic carboxylic acylamino groups having from 2 to 5 carbon atoms, aromatic carboxylic acylamino groups having from 7 to 15 carbon atoms, nitro groups, cyano groups, carboxy groups, protected carboxy groups, alkyl groups having from 1 to 5 carbon atoms and alkyl groups which have from 1 to 5 carbon atoms and which are substituted by at least one substituent selected from the group consisting of substituents F, defined below, wherein the aryl groups of said aryloxy, aralkyloxy, aromatic carboxylic acyloxy, arylthio, aralkylthio, arylamino, diarylamino, aralkylamino, diaralkylamino and aromatic carboxylic acylamino groups are unsubstituted or have at least one substituent selected from the group consisting of substituents E, defined below, and in which the aralkyl part of each of said aralkyloxy, aralkylthio, aralkylamino and diaralkylamino groups is an alkyl group which has from 1 to 6 carbon atoms which is substituted by at least one aryl group having from 6 to 10 carbon atoms;

substituents E:
  alkyl groups having from 1 to 4 carbon atoms, hydroxy groups, halogen atoms, alkoxy groups having from 1 to 4 carbon atoms, carboxy groups, protected carboxy groups and amino groups;

substituents F:
  halogen atoms, hydroxy groups and aliphatic carboxylic acyloxy groups having from 2 to 5 carbon atoms;

pharmaceutically acceptable salts and esters thereof.

The present invention is also directed to a compound selected from the group consisting of 7-[5-(1,3-dioxan-5-yl)methoxyimino-2-methyl-8-(2-methylbutyryloxy)-3-oxo-1,2,3,5,6,7,8,8a-octahydro-1-naphthyl]-3-hydroxy-5-oxo-heptanoic acid and pharmaceutically acceptable salts thereof.

The invention also provides a pharmaceutical composition comprising an agent for inhibiting cholesterol biosynthesis in admixture with a pharmaceutically acceptable carrier or diluent, wherein said agent is selected. from the group consisting of compounds of formula (I), as defined above, and pharmaceutically acceptable salts and esters thereof.

The invention still further provides a method of treating a mammal suffering from a disorder arising from a blood cholesterol imbalance, which comprises administering to said mammal an effective amount of an agent inhibiting cholesterol biosynthesis, wherein said agent is selected from the group consisting of compounds of formula (I), as defined above, and pharmaceutically acceptable salts and esters thereof.

The invention also provides processes for preparing the compounds of the present invention, which are described in more detail hereinafter.

DETAILED DESCRIPTION OF INVENTION

In the above formula (I), when X represents an alkyl group, it may be a straight or branched chain alkyl group having from 1 to 10 carbon atoms, preferably from 1 to 7 carbon atoms, for example a methyl, ethyl, propyl, isopropyl, butyl, sec-butyl, isobutyl, t-butyl, pentyl, 1-methylbutyl, 2-methylbutyl, isopentyl, 1,1-dimethylpropyl, neopentyl, 1,2-dimethylpropyl, 1-ethylpropyl, hexyl, 1-methylpentyl, 2-methylpentyl, 1,1-dimethylbutyl, 1,3-dimethylbutyl, 1-ethylbutyl, 2-ethylbutyl, 1-methyl-1-ethylpropyl, heptyl, 1-methyl-1-ethylbutyl, 2-methyl-2-ethylbutyl, octyl, 1-methylheptyl, 2-ethylhexyl, 1,1,3,3-tetramethylbutyl, nonyl, decyl or 3,7-dimethyloctyl group. Such groups may be unsubstituted or they may be substituted by at least one substituent selected from the group consisting of substituents A, defined above and exemplified below. There is no particular restriction on the number of such substituents, except such as may be imposed by the number of substitutable positions (e.g. 3 in the methyl group, 5 in the ethyl group, and so on) or by steric constraints. However, in general from 1 to 4, more preferably from 1 to 3, substituents are preferred. The same applies to other substituted groups where no specific number of substituents is referred to. Specific examples of preferred substituted alkyl groups include the trichloromethyl, trifluoromethyl, chloromethyl, fluoromethyl, bromomethyl, iodomethyl, hydroxymethyl, carboxymethyl, methoxycarbonylmethyl, ethoxycarbonylmethyl, methoxymethyl, ethoxymethyl, propoxymethyl, butoxymethyl, aminomethyl, acetoxymethyl, propionyloxymethyl, butyryloxymethyl, pivaloyloxymethyl, 2,2,2-trichloroethyl, 2,2,2-trifluoroethyl, 1-chloroethyl, 2-chloroethyl, 1-fluoroethyl, 2-fluoroethyl, 2-bromoethyl, 2-iodoethyl, 1-hydroxyethyl, 2-hydroxyethyl, 2-carboxyethyl, 2-methoxycarbonylethyl, 2-ethoxycarbonylethyl, 2-methoxyethyl, 2-ethoxyethyl, 2-propoxyethyl, 2-butoxyethyl, 1-aminoethyl, 2-aminoethyl, 2-acetoxyethyl, 2-propionyloxyethyl, 2-butyryloxyethyl, 2-pivaloyloxyethyl, 3-chloropropyl, 1-fluoropropyl, 3-fluoropropyl, 3-bromopropyl, 3-iodopropyl, 1,1-difluoropropyl, 3-hydroxypropyl, 3-carboxypropyl, 3-methoxycarbonylpropyl, 3-ethoxycarbonylpropyl, 1-ethoxycarbonyl-1-methylethyl, 1-amino-3-methoxycarbonylpropyl, 1-fluoro-1-methylpropyl, 1-ethyl-1-fluoropropyl, 1-amino-2-methylpropyl, 4-hydroxybutyl, 3-acetoxy-1,1-dimethylpropyl, 4-acetoxy-1-methylbutyl, 3-hydroxy-1,1-dimethylpropyl, 4-ethoxycarbonyl-1-methylbutyl, 1-chloro-1-methylpropyl and 4-hydroxy-1,1-dimethylbutyl groups.

When X represents an alkenyl group, it may be a straight or branched chain alkenyl group having from 3 to 10 carbon atoms, preferably from 3 to 7 carbon atoms. Examples include the 1-propenyl, 2-propenyl, 1-methylvinyl, 2-butenyl, 3-butenyl, 1-methyl-1-propenyl, 2-methyl-2-propenyl, 3-methyl-2-butenyl, 2-pentenyl, 3-pentenyl, 4-hexenyl, 1-hexenyl, 5-heptenyl, 2-octenyl, 4-octenyl, 2-nonenyl, 3-nonenyl, 4-nonenyl, 3-decenyl or 5-decenyl group. Such groups may be unsubstituted or they may be substituted by at least one substituent selected from the group consisting of substituents A, defined above and exemplified below.

When X represents a cycloalkyl group, it may be a cycloalkyl group having from 3 to 10 carbon atoms, preferably from 3 to 7 carbon atoms, and may be a monocyclic or polycyclic, e.g. bicyclic, group, and, in the case of the polycyclic groups, it may be a fused or bridged cyclic hydrocarbon group. Examples of such groups include the cyclopropyl, cyclobutyl, cyclopentyl, cyclohexyl, cycloheptyl, cyclooctyl, cyclononyl, cyclodecyl, bornyl, norbornyl and adamantyl groups. Of these, we especially prefer the monocyclic groups having from 3 to 7 ring carbon atoms, and most especially the cyclopropyl, cyclopentyl and cyclohexyl groups.

When X represents an aryl group, it is a carbocyclic aromatic group and may have from 6 to 10 ring carbon atoms, more preferably 6 or 10 ring carbon atoms. Examples include the phenyl, 1-naphthyl and 2-naphthyl groups, preferably the phenyl group. Such groups may be unsubstituted or they may be substituted by at least one substituent selected from the group consisting of substituents B, defined above and exemplified below. Specific examples of preferred substituted aryl groups include the 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-hydroxyphenyl, 3-hydroxyphenyl, 4-hydroxyphenyl, 2-methoxyphenyl, 3-methoxyphenyl, 4-methoxyphenyl, 2-acetoxyphenyl, 3-acetoxyphenyl, 4-acetoxyphenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2,6-dimethylphenyl, 3,4-dimethylphenyl, 3,5-dimethylphenyl and 2,5-dimethylphenyl groups.

When X represents an aralkyl group, it is an alkyl group having from 1 to 6 carbon atoms which is substituted by at least one aryl group, as defined above. It preferably has in total from 7 to 12 carbon atoms, more preferably from 7 to 9 carbon atoms; the alkyl part thereof preferably has from 1 to 6 carbon atoms, more preferably from 1 to 3 carbon atoms, most preferably 1 or 2 carbon atoms; and the aryl part preferably has from 6 to 10 carbon atoms, more preferably 6 or 10 carbon atoms, and is most preferably the phenyl group. It may have one or more, preferably from 1 to 3, such aryl groups, most preferably one such aryl group. Examples of such groups include the benzyl, benzhydryl, trityl, α-methylbenzyl, α-naphthylmethyl, β-naphthylmethyl, phenethyl, 3-phenylpropyl, 1,1-dimethylbenzyl, 4-phenylbutyl, 1-methyl-3-phenylpropyl, 5-phenylpentyl and 6-phenylhexyl groups. Such groups may be unsubstituted or they may be substituted by at least one substituent selected from the group consisting of substituents B, defined above and exemplified below. Specific examples of preferred substituted aryl groups include the above unsubstituted groups in which the phenyl group is replaced by one of the substituted aryl groups exemplified above in relation to the substituted aryl groups which may be represented by X.

When X represents a heterocyclic group, it contains 5 or 6 ring atoms, of which from 1 to 3 are oxygen atoms and/or sulfur atoms and/or nitrogen atoms. Where the group contains 1 or 2 hetero-atoms, this or these may be freely selected from the nitrogen, oxygen and sulfur hetero-atoms. Where the group contains 3 hetero-atoms, we prefer that 1, 2 or 3 of these should be nitrogen atoms, and correspondingly 0 at 2, 1 or 0 should be oxygen or sulfur atoms. It may be a fully unsaturated heterocyclic group and examples of such groups include the 2-furyl, 3-furyl, 2-thienyl, 3-thienyl, 2-thiazolyl, 4-thiazolyl, 1-pyrrolyl, 2-pyrrolyl, 3-pyridyl, 4-pyridyl, 2-pyrimidinyl, 5-pyrimidinyl, 2-pyranyl, 4-pyranyl, 3-isoxazolyl, 5-isoxazolyl, 2-oxazolyl and 5-oxazolyl groups. Alternatively, it may be a a wholly or partially saturated group, for example a 2-tetrahydrofuryl, 3-tetrahydrofuryl, 2-tetrahydrothienyl, 3-tetrahydrothienyl, 1-pyrrolidinyl, 3-pyrrolidinyl, 2-piperazyl, piperidino, 2-piperidyl, morpholino, 3-morpholinyl, 2-tetrahydropyranyl, 4-tetrahydropyranyl, 1,4-dioxan-2-yl, 1,3-dioxan-4-yl or 1,3-dioxan-5-yl group. Of these, we prefer the 5- and 6-membered unsaturated heterocyclic groups containing from 1 to 3 oxygen atoms and/or sulfur atoms and/or nitrogen atoms.

When X represents an alkyl group or an alkenyl group, such groups may be substituted or unsubstituted and, if substituted, the substituents are selected from the group consisting of substituents A, defined above. There is, in principle, no restriction on the number of substituents on any alkyl or alkenyl group represented by X, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine, iodine and fluorine atoms;

the hydroxy group;

alkoxy groups having from 1 to 4 carbon atoms, such as the methoxy and ethoxy groups;

$C_2$–$C_5$ aliphatic carboxylic acyloxy groups, especially $C_2$–$C_5$ alkanoyloxy groups, such as the acetoxy, propionyloxy, butyryloxy, valeryloxy, isovaleryloxy and pivaloyloxy groups;

the amino group;

the carboxy group; and protected carboxy groups in which the protecting group is preferably as defined below.

Protecting groups for carboxy groups are well known in this field and the skilled man would have no difficulty in determining what groups may be used. By way of illustration only, examples of such groups include lower alkyl groups (e.g. having from 1 to 4 carbon atoms), to form a protected group such as the methoxycarbonyl, ethoxycarbonyl or t-butoxycarbonyl group; aralkyl groups (preferably as defined above as such groups which may be represented by X), to form an aralkyloxycarbonyl group, such as the benzyloxycarbonyl, diphenylmethoxycarbonyl, 4-nitrobenzyloxycarbonyl and 2-nitrobenzyloxycarbonyl groups; lower alkenyl and haloalkenyl groups (e.g. having from 1 to 4 carbon atoms), to form an alkenyloxycarbonyl or haloalkenyloxycarbonyl group, such as the allyloxycarbonyl and 2-chloroallyloxycarbonyl groups; lower haloalkyl groups (e.g. having from 1 to 4 carbon atoms), to form a haloalkoxycarbonyl group such as the 2,2,2-trichloroethoxycarbonyl and 2,2,2-tribromoethoxycarbonyl groups; and tri(substituted)silylalkyl groups in which the substituents are preferably alkyl groups having from 1 to 4 carbon atoms and/or phenyl groups and in which the alkyl group has from 1 to 4 carbon atoms, to form a silylalkoxycarbonyl group such as the 2-(trimethylsilyl)ethoxycarbonyl group. Other protecting groups which may be used are listed hereafter as the ester groups for forming esters of the compounds of the present invention. When reference is made herein to "protected carboxy" groups, e.g. in relation to substituents A, B, C, D and E, all such protecting groups are included.

Of these substituents, the most preferred are the halogen atoms, the hydroxy group, the aliphatic carboxylic acyloxy groups having from 2 to 5 carbon atoms, the carboxy group, and protected carboxy groups; and most preferred of all are the halogen atoms and the carboxy group.

When X represents a cycloalkyl group, an aryl group, an aralkyl group or a heterocyclic group, such groups may be substituted or unsubstituted and, if substituted, the substituents are selected from the group consisting of substituents B, defined above. There is, in principle, no restriction on the number of substituents on any cycloalkyl, aryl, aralkyl or heterocyclic group represented by X, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine, iodine and fluorine atoms;

the hydroxy group;

alkoxy groups having from 1 to 4 carbon atoms, such as the methoxy and ethoxy groups;

$C_2$–$C_5$ aliphatic carboxylic acyloxy groups, especially $C_2$–$C_5$ alkanoyloxy groups, such as the acetoxy, propionyloxy, butyryloxy, valeryloxy, isovaleryloxy and pivaloyloxy groups;

the amino group;

the carboxy group;

protected carboxy groups in which the protecting group is preferably as defined above for the protected groups of substituents A, such as the methoxycarbonyl, ethoxycarbonyl, t-butoxycarbonyl, benzyloxycarbonyl, diphenylmethoxycarbonyl, 4-nitrobenzyloxycarbonyl, 2-nitrobenzyloxycarbonyl, allyloxycarbonyl, 2-chloroallyloxycarbonyl, 2,2,2-trichloroethoxycarbonyl, 2,2,2-tribromoethoxycarbonyl and 2-(trimethylsilyl)ethyloxycarbonyl groups;

$C_1$–$C_5$ alkyl groups, such as the methyl, ethyl, propyl, isopropyl, butyl and pentyl groups; and halogen-substituted $C_1$–$C_5$ alkyl groups, such as the trifluoromethyl group.

Of these substituents, the most preferred are the halogen atoms, the hydroxy group, alkoxy groups having from 1 to 4 carbon atoms, $C_2$–$C_5$ aliphatic carboxylic acyloxy groups, $C_1$–$C_5$ alkyl groups and halogen-substituted $C_1$–$C_5$ alkyl groups, and the most preferred of all are the halogen atoms and halogen-substituted $C_1$–$C_5$ alkyl groups.

When A represents a divalent saturated acyclic hydrocarbon group, it may be an alkylene group having from 1 to 10 carbon atoms, preferably from 1 to 5 carbon atoms. The group may be a straight or branched chain group, and the two "free" valences may be on the same carbon atom (in which case, the group is sometimes known as an "alkylidene" group) or they may be on different carbon atoms. Examples of such groups include the methylene, ethylidene, ethylene, 1-methylethylene, trimethylene, 1,2-dimethylethylene, 1-ethylethylene, 1-methyltrimethylene, 2-methyltrimethylene, tetramethylene, 1-propylethylene, 1-ethyl-2-methylethylene, 1-ethyltrimethylene, 2-ethyltrimethylene, 1,3-dimethyltrimethylene, 1-methyltetramethylene, 2-methyltetramethylene, pentamethylene, 1-butylethylene, 1-methyl-2-propylethylene, 1,2-diethylethylene, 1-methyl-1-propylethylene, 2-propyltriethylene, 1-ethyl-3-methyltrimethylene, 1-ethyltetramethylene, 2-ethyltetramethylene, 1,3-dimethyltetramethylene, 1-methylpentamethylene, 2-methylpentamethylene, 3-methylpentamethylene, hexamethylene, 1-pentylethylene, 1-butyl-2-methylethylene, 1-ethyl-2-propylethylene, 1-butyltrimethylene, 2-butyltrimethylene, 1,3-diethyltrimethylene, 1-methyl-3-propyltrimethylene, 1-propyltetramethylene, 2-propyltetramethylene, 1-ethyl-4-methyltetramethylene, 3-ethyl-1-methyltetramethylene, 1-ethylpentamethylene, 3-ethylpentamethylene, 1,3-dimethylpentamethylene, 1-methylhexamethylene, 3-methylhexamethylene, heptamethylene, 1-hexylethylene, 1-methyl-2-pentylethylene, 1-butyl-2-ethylethylene, 1,2-dipropylethylene, 1-pentyltrimethylene, 2-pentyltrimethylene, 1-butyl-3-methyltrimethylene, 1-butyl-2-methyltrimethylene, 1-ethyl-3-propyltrimethylene, 1,2-dimethyl-3-propyltrimethylene, 1-butyltetramethylene, 1-methyl-4-propyltetramethylene, 1-propylpentamethylene, 3-propylpentamethylene, 2-ethyl-4-methylpentamethylene, 1-ethylhexamethylene, 3-ethylhexamethylene, 1,3-dimethylhexamethylene, 1-methylheptamethylene, 4-methylheptamethylene, octamethylene and 2,6-dimethyloctamethylene.

When A represents a divalent unsaturated acyclic hydrocarbon group, it may be an alkenylene group having from 3 to 10 carbon atoms, preferably from 3 to 7 carbon atoms, and most preferably from 3 to 5 carbon atoms. The group may be a straight or branched chain group, and the two "free" valences may be on the same carbon atom or they may be on different carbon atoms. Examples of such groups include the 2-propenylene, 2-methyl-2-propenylene, 2-butenylene, 3-butenylene, 2-pentenylene, 4-pentenylene, 2-methyl-2-butenylene, 2-hexenylene, 2-heptenylene, 3-methyl-2-hexenylene, 3-ethyl-2-pentenylene, 2-methyl-3-hexenylene, 2-octenylene, 4-octenylene, 3-methyl-2-heptenylene, 3,5-dimethyl-2-hexenylene, 2-nonenylene, 3-methyl-2-octenylene, 3,5-dimethyl-3-heptenylene, 2-decenylene and 3,7-dimethyl-2-octenylene groups. Alternatively, it may be an alkadienylene group having from 5 to 10 carbon atoms, preferably from 5 to 8 carbon atoms. The group may be a straight or branched chain group, and the two "free" valences may be on the same carbon atom or they may be on different carbon atoms. Examples of such groups include the 2,4-pentadienylene, 2,4-hexadienylene, 4-methyl-2,4-pentadienylene, 2,4-heptadienylene, 2,6-heptadienylene, 3-methyl-2,4-hexadienylene, 2,6-octadienylene, 3-methyl-2,6-heptadienylene, 2-methyl-2,4-heptadienylene, 2,8-nonadienylene, 3-methyl-2,6-octadienylene, 2,6-decadienylene, 2,9-decadienylene and 3,7-dimethyl-2,6-octadienylene groups. It may also be an alkynylene group having from 3 to 10 carbon atoms, preferably from 3 to 5 carbon atoms. The group may be a straight or branched chain group, and the two "free" valences may be on the same carbon atom or they may be on different carbon atoms. Examples of such groups include the 2-propynylene, 2-butynylene, 2-pentynylene, 2-hexynylene, 4-methyl-2-pentynylene, 2-heptynylene, 3-octynylene and 4-decynylene groups.

These divalent saturated or unsaturated acyclic hydrocarbon groups may be substituted or unsubstituted and, if substituted, the substituents are selected from the group consisting of substituents C, defined above. There is, in principle, no restriction on the number of substituents on any such group, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine, iodine and fluorine atoms;

the hydroxy group;

alkoxy groups having from 1 to 4 carbon atoms, such as the methoxy and ethoxy groups;

aryloxy groups having from 6 to 14 carbon atoms, such as the phenoxy, 1-naphthyloxy or 2-naphthyloxy group, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, $C_1$–$C_4$ alkoxy groups, carboxy groups, protected carboxy groups, e.g. as exemplified above in relation to substituents A, and amino groups; examples of such groups include the 4-tolyloxy, 4-hydroxyphenoxy, 4-chlorophenoxy, 4-fluorophenoxy, 4-methoxyphenoxy, 4-carboxyphenoxy, 4-methoxycarbonylphenoxy and 4-aminophenoxy groups;

aralkyloxy groups in which the alkoxy part has from 1 to 6 carbon atoms and is substituted by at least one aryl group having from 6 to 10, more preferably 6 or 10, ring carbon atoms; in general, we prefer those aralkyloxy groups having in total from 7 to 13 carbon atoms in which the aryl part is preferably a phenyl group and the alkyl part is preferably $C_1$–$C_3$, such as the benzyloxy or phenethyloxy groups; the aryl moieties may be unsubstituted or may have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the benzyloxy, phenethyloxy, 1-phenylethoxy, 4-methylbenzyloxy, 4-hydroxybenzyloxy, 4-chlorobenzyloxy, 4-methoxybenzyloxy, 4-carboxybenzyloxy, 4-methoxycarbonylbenzyloxy and 4-aminobenzyloxy groups;

$C_2$–$C_5$ aliphatic carboxylic acyloxy groups, especially $C_2$–$C_5$ alkanoyloxy groups, such as the acetoxy, propionyloxy, butyryloxy, valeryloxy, isovaleryloxy and pivaloyloxy groups;

$C_7$–$C_{15}$ aromatic carboxylic acyloxy groups, especially benzoyloxy and naphthoyloxy groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the benzoyloxy, 1-naphthoyloxy, 2-naphthoyloxy, 4-methylbenzoyloxy, 2-hydroxybenzoyloxy, 4-hydroxybenzoyloxy, 4-chlorobenzoyloxy, 4-methoxybenzoyloxy, 4-carboxybenzoyloxy, 4-methoxycarbonylbenzoyloxy and 4-aminobenzoyloxy groups;

the amino group; mono- and di-$C_1$–$C_4$ alkyl substituted amino groups, in which, in the case of the dialkylamino groups, the two alkyl groups may be the same or different, such as the methylamino, ethylamino, propylamino, butylamino, t-butylamino, dimethylamino, methylethylamino, methylbutylamino and diethylamino groups;

mono- and di-$C_6$–$C_{14}$ aryl substituted amino groups, especially phenylamino and naphthylamino groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the phenylamino, 1-naphthylamino, 2-naphthylamino, 4-tolylamino, 4-hydroxyphenylamino, 4-chlorophenylamino, 4-methoxyphenylamino, 4-carboxyphenylamino, 4-methoxycarbonylphenylamino and 4-aminophenylamino groups;

mono- and di-aralkyl-substituted amino groups, in which the aralkyl group is an alkyl group having from 1 to 6 carbon atoms which is substituted by at least one aryl group having from 6 to 10 ring carbon atoms, and which most preferably has a total of from 7 to 9 carbon atoms in the aralkyl group; especially benzylamino and phenethylamino groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the benzylamino, phenethylamino, 4-methylbenzylamino, 4-hydroxybenzylamino, 4-chlorobenzylamino, 4-methoxybenzylamino, 4-carboxybenzylamino, 4-methoxycarbonylbenzylamino and 4-aminobenzylamino groups;

$C_2$–$C_5$ aliphatic carboxylic acyl substituted amino groups, especially $C_2$–$C_5$ alkanoylamino groups, such as the acetamido, propionamido, butyramido, valeramido, isovaleramido and pivaloylamino groups;

$C_7$–$C_{15}$ aromatic carboxylic acyl substituted amino groups, especially benzamido and naphthoylamido groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the benzamido, naphthoylamido, 4-methylbenzamido, 4-hydroxybenzamido, 4-chlorobenzamido, 4-methoxybenzamido, 4-carboxybenzamido, 4-methoxycarbonylbenzamido and 4-aminobenzamido groups;

the carboxy group; and protected carboxy groups in which the protecting group is preferably as defined above for the protected groups of substituents A, for example: an alkoxycarbonyl group, such as the methoxycarbonyl, ethoxycarbonyl or t-butoxycarbonyl group; an aralkyloxycarbonyl group, such as the benzyloxycarbonyl, diphenylmethoxycarbonyl, 4-nitrobenzyloxycarbonyl or 2-nitrobenzyloxycarbonyl group; an alkenyloxycarbonyl or haloalkenyloxycarbonyl group, such as the allyloxycarbonyl or 2-chloroallyloxycarbonyl group; a haloalkoxycarbonyl group, such as the 2,2,2-trichloroethoxycarbonyl or 2,2,2-tribromoethoxycarbonyl group; and substituted silylalkoxycarbonyl groups, such as the 2-(trimethylsilyl)ethyloxycarbonyl group.

Of these substituents, the preferred ones are:

halogen atoms; hydroxy groups; alkoxy groups having from 1 to 4 carbon atoms; aryloxy groups having from 6 to 14 carbon atoms (wherein the aryl moieties may have from 1 to 3 substituents, which may be the same or different from one another, such as $C_1$–$C_4$ alkyl, hydroxy, halogen, $C_1$–$C_4$ alkoxy, carboxy, protected carboxy and amino); $C_2$–$C_5$ aliphatic carboxylic acyloxy groups; amino groups; mono- and di-$C_1$–$C_4$ alkyl substituted amino groups; $C_2$–$C_5$ aliphatic carboxylic acyl substituted amino groups; $C_7$–$C_{15}$ aromatic carboxylic acyl substituted amino groups (wherein the aryl moieties may have from 1 to 3 substituents which may be the same or different from one another, such as $C_1$–$C_4$ alkyl, hydroxy, halogen, $C_1$–$C_4$ alkoxy, carboxy, protected carboxy and amino); carboxy groups; and protected carboxy groups;

more preferably:

halogen atoms; hydroxy groups, alkoxy groups having from 1 to 4 carbon atoms; amino groups; mono- or di-$C_1$–$C_4$ alkyl substituted amino groups; and $C_2$–$C_5$ aliphatic carboxylic acyl substituted amino groups; and most preferably:

hydroxy groups and alkoxy groups having from 1 to 4 carbon atoms.

When Y represents an aryl group, it may be an aryl group having from 6 to 14 carbon atoms, preferably from 6 to 10 carbon atoms, and more preferably 6 or 10 ring carbon atoms, and examples include the phenyl, 1-naphthyl, 2-naphthyl, anthracenyl and phenanthryl groups, which may be substituted or unsubstituted, and, if substituted, have at least one substituent selected from the group consisting of substituents D, defined above and exemplified below. Of these, the phenyl and naphthyl groups are preferred, the phenyl group being most preferred.

When Y represents a cycloalkyl group, it may be a monocyclic or polycyclic (e.g. bicyclic or tricyclic) cycloalkyl group (which term, as used herein, includes the terpenyl hydrocarbon groups) having from 3 to 10 carbon atoms, preferably from 3 to 8 carbon atoms, most preferably from 5 to 7 carbon atoms, and examples include the cyclopropyl, cyclobutyl, cyclopentyl, cyclohexyl, cycloheptyl, cyclooctyl, cyclononyl, cyclodecyl, adamantyl, pinanyl, bornyl and menthyl groups, which may be substituted or unsubstituted, and, if substituted, have at least one substituent selected from the group consisting of substituents D, defined above and exemplified below.

When Y represents a heterocyclic group, it may be a simple 5- or 6-membered unsaturated heterocyclic group containing from 1 to 3 oxygen atoms and/or sulfur atoms and/or nitrogen atoms, which may be substituted or unsubstituted. Where the group contains 3 hetero-atoms, we prefer that 1, 2 or 3 of these should be nitrogen atoms, and correspondingly that 2, 1 or 0 should be oxygen or sulfur atoms. More preferably the group contains 1 or 2 hetero-atoms; which, where there is one hetero-atom, may be a nitrogen, oxygen or sulfur atom, or, where there are two hetero-atoms, preferably one of these is a nitrogen atom and the other is a nitrogen, oxygen or sulfur atom. Examples of the unsubstituted groups include the 2-furyl, 3-furyl, 2-thienyl, 3-thienyl, 2-thiazolyl, 4-thiazolyl, 1-pyrrolyl, 2-pyrrolyl, 3-pyridyl, 4-pyridyl, 2-pyrimidinyl, 5-pyrimidinyl, 2-pyranyl, 4-pyranyl, 3-isoxazolyl, 4-isoxazolyl, 5-isoxazolyl, 2-oxazolyl and 5-oxazolyl groups.

Alternatively, it may be a 5- or 6-membered saturated heterocyclic group containing from 1 to 3 oxygen atoms and/or sulfur atoms and/or nitrogen atoms, which may be substituted or unsubstituted. Where the group contains 3 hetero-atoms, we prefer that 1, 2 or 3 of these should be nitrogen atoms, and correspondingly that 2, 1 or 0 should be oxygen or sulfur atoms. More preferably the group contains 1 or 2 hetero-atoms; which, where there is one hetero-atom, may be a nitrogen, oxygen or sulfur atom, or, where there are two hetero-atoms, preferably one of these is a nitrogen atom and the other is a nitrogen, oxygen or sulfur atom, or both are oxygen atoms. Examples of the unsubstituted groups include the 2-tetrahydrofuryl, 3-tetrahydrofuryl, 2-tetrahydrothienyl, 3-tetrahydrothienyl, 1-pyrrolidinyl, 3-pyrrolidinyl, 2-piperazyl, piperidino, 2-piperidyl, morpholino, 3-morpholinyl, 2-tetrahydropyranyl, 4-tetrahydropyranyl, 1,4-dioxan-2-yl, 1,3-dioxan-4-yl and 1,3-dioxan-5-yl groups.

Alternatively, it may be a condensed heterocyclic group in which a 5- or 6-membered saturated heterocyclic group containing from 1 to 3 oxygen atoms and/or sulfur atoms and/or nitrogen atoms is condensed with a benzene ring. The heterocyclic part of such a ring system may be fully unsaturated or partially unsaturated, and the group may be substituted or unsubstituted. Examples of the unsubstituted groups include the 2-benzofuranyl, 2-2H-chromenyl, 2-benzothienyl, 2-indolinyl, 3-indolinyl, 2-dihydrobenzofuranyl, 2-chromanyl, 1,4-benzodioxan-2-yl, 4-quinolyl and 1-isoquinolyl groups.

These heterocyclic groups are preferably 5- or 6-membered unsaturated, saturated or condensed heterocyclic groups having 1 or 2 oxygen atoms and/or nitrogen atoms and/or sulfur atoms, most suitably 5- or 6-membered saturated or unsaturated heterocyclic groups containing 1 or 2 oxygen atoms and/or nitrogen atoms and/or sulfur atoms. Any of these heterocyclic groups may be substituted or unsubstituted, and, if substituted, they have at least one substituent selected from the group consisting of substituents D, defined above and exemplified below.

These aryl, cycloalkyl and heterocyclic groups represented by Y may be substituted or unsubstituted and, if substituted, the substituents are selected from the group consisting of substituents D, defined above. There is, in principle, no restriction on the number of substituents on any such group, except those dictated by the number of substitutable positions and, possibly, by steric constraints. However, in general, we prefer that there should be from 1 to 4, more preferably 1 or 2, of these substituents. Where there are 2 or more such substituents, these may be the same or different from one another, and examples include the following groups and atoms:

halogen atoms, such as the chlorine, bromine, iodine and fluorine atoms;

the hydroxy group;

alkoxy groups having from 1 to 4 carbon atoms, such as the methoxy, ethoxy, propoxy, isopropoxy, butoxy, isobutoxy, sec-butoxy and t-butoxy groups;

aryloxy groups having from 6 to 14 carbon atoms, such as the phenoxy, 1-naphthyloxy and 2-naphthyloxy groups, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the 4-tolyloxy, 4-hydroxyphenoxy, 4-chlorophenoxy, 4-fluorophenoxy, 2-methoxyphenoxy, 4-methoxyphenoxy, 4-carboxyphenoxy, 4-methoxycarbonylphenoxy and 4-aminophenoxy groups;

aralkyloxy groups in which an alkoxy group having from 1 to 6 carbon atoms is substituted by at least one aryl group having from 6 to 10, preferably 6 or 10, ring carbon atoms; the aralkyloxy group preferably has a total of from 7 to 13 carbon atoms, in which the aryl part is preferably a phenyl group and the alkyl part is preferably $C_1$–$C_3$, such as the benzyloxy and phenethyloxy groups; the aryl moieties may be unsubstituted or may have, for example, from 1 to 5 substituents, preferably from 1 to 3 substituents, selected from the group consisting of substituents E, which may be the same or different from one another; examples of such substituents include alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; specific examples of such aralkyloxy groups include the benzyloxy, phenethyloxy, 1-phenylethoxy, 4-methylbenzyloxy, 4-hydroxybenzyloxy, 4-chlorobenzyloxy, 4-methoxybenzyloxy, 4-carboxybenzyloxy, 4-methoxycarbonylbenzyloxy and 4-aminobenzyloxy groups;

$C_2$–$C_5$ aliphatic carboxylic acyloxy groups, especially $C_2$–$C_5$ alkanoyloxy groups, such as the acetoxy, propionyloxy, butyryloxy, valeryloxy, isovaleryloxy and pivaloyloxy groups;

$C_7$–$C_{15}$ aromatic carboxylic acyloxy groups, especially benzoyloxy and naphthoyloxy groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the benzoyloxy, 1-naphthoyloxy, 2-naphthoyloxy, 4-methylbenzoyloxy, 2-hydroxybenzoyloxy, 4-hydroxybenzoyloxy, 4-chlorobenzoyloxy, 4-methoxybenzoyloxy, 4-carboxybenzoyloxy, 4-methoxycarbonylbenzoyloxy and 4-aminobenzoyloxy groups;

the mercapto group;

alkylthio groups having from 1 to 4 carbon atoms, such as the methylthio and ethylthio groups;

arylthio groups having from 6 to 14 carbon atoms, especially phenylthio and naphthylthio groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the phenylthio, 1-naphthylthio, 2-naphthylthio, 4-tolylthio, 4-hydroxyphenylthio, 4-chlorophenylthio, 4-methoxyphenylthio, 4-carboxyphenylthio, 4-methoxycarbonylphenylthio and 4-aminophenylthio groups;

aralkylthio groups in which an alkylthio group having from 1 to 6 carbon atoms is substituted by at least one aryl group having from 6 to 10, preferably 6 or 10, ring carbon atoms; the aralkylthio group preferably has a total of from 7 to 13 carbon atoms; especially preferred are the benzylthio and phenethylthio groups which may be substituted or unsubstituted; in these groups, the aryl moieties may be unsubstituted or may have, for example, from 1 to 5 substituents, preferably from 1 to 3 substituents, selected from the group consisting of substituents E, which may be the same or different from one another; examples of such substituents include alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; specific examples of such aralkylthio groups include the benzylthio, phenethylthio, 4-methylbenzylthio, 4-hydroxybenzylthio, 4-chlorobenzylthio, 4-methoxybenzylthio, 4-carboxybenzylthio, 4-methoxycarbonylbenzylthio and 4-aminobenzylthio groups;

the amino group;

mono- and di-$C_1$–$C_4$ alkyl substituted amino groups, such as the methylamino, dimethylamino and diethylamino groups;

mono- and di-$C_6$–$C_{14}$ aryl substituted amino groups, especially phenylamino and naphthylamino groups which are substituted or unsubstituted, wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the phenylamino, 1-naphthylamino, 2-naphthylamino, 2-tolylamino, 4-tolylamino, 4-hydroxyphenylamino, 4-chlorophenylamino, 4-methoxyphenylamino, 4-carboxyphenylamino, 4-methoxycarbonylphenylamino and 4-aminophenylamino groups;

mono- and di-aralkyl-substituted amino groups, in which the aralkyl part is an alkyl group having from 1 to 6 carbon atoms which is substituted by at least one (and preferably only one) aryl substituent; especially preferred are the benzylamino and phenethylamino groups which may be substituted or unsubstituted; and wherein the aryl moieties may be unsubstituted or may have, for example, from 1 to 5 substituents, preferably from 1 to 3 substituents, selected from the group consisting of substituents E, which may be the same or different from one another; examples of such substituents include alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; specific examples of such aralkylamino groups include the benzylamino, phenethylamino, 4-methylbenzylamino, 4-hydroxybenzylamino, 4-chlorobenzylamino, 4-methoxybenzylamino, 4-carboxybenzylamino, 4-methoxycarbonylbenzylamino and 4-aminobenzylamino groups;

$C_2$–$C_5$ aliphatic carboxylic acyl substituted amino groups, especially $C_2$–$C_5$ alkanoylamino groups, such as the acetamido, propionamido, butyramido, valeramido, isovaleramido and pivaloylamino groups;

$C_7$–$C_{15}$ aromatic carboxylic acyl substituted amino groups, especially benzamido and naphthoylamido groups which are substituted or unsubstituted, and wherein the aryl moieties may be unsubstituted or have, for example, from 1 to 5 substituents, preferably from 1 to 3 substituents, selected from the group consisting of substituents E, which may be the same or different from one another, such as alkyl groups having from 1 to 4 carbon atoms, hydroxy groups, halogen atoms, alkoxy groups having from 1 to 4 carbon atoms, carboxy groups, protected carboxy groups, e.g. as exemplified above in relation to substituents A, and amino groups; examples of such groups include the benzamido, naphthoylamido, 4-methylbenzamido, 4-hydroxybenzamido, 4-chlorobenzamido, 4-methoxybenzamido, 4-carboxybenzamido, 4-methoxycarbonylbenzamido and 4-aminobenzamido groups;

the nitro group;

the cyano group;

the carboxy group;

protected carboxy groups in which the protecting group is preferably as defined above for the protected groups of substituents A, for example: alkoxycarbonyl groups, such as the methoxycarbonyl, ethoxycarbonyl and t-butoxycarbonyl groups; aralkyloxycarbonyl groups, such as the benzyloxycarbonyl, diphenylmethoxycarbonyl, 4-nitrobenzyloxycarbonyl and 2-nitrobenzyloxycarbonyl groups; alkenyloxycarbonyl and haloalkenyloxycarbonyl groups, such as the allyloxycarbonyl and 2-chloroallyloxycarbonyl groups; haloalkoxycarbonyl groups, such as the 2,2,2-trichloroethoxycarbonyl and 2,2,2-tribromoethoxycarbonyl groups; and substituted silylalkoxycarbonyl groups, such as the 2-(trimethylsilyl)ethoxycarbonyl group;

$C_1$–$C_5$ alkyl groups, which may be straight or branched chain groups, such as the methyl, ethyl, propyl, butyl and pentyl groups;

halogen-substituted $C_1$–$C_5$ alkyl groups, which may be straight or branched chain groups, such as the trifluoromethyl group;

$C_1$–$C_5$ hydroxyalkyl groups, such as the hydroxymethyl and hydroxyethyl groups; and $C_1$–$C_5$ alkyl groups having at least one, and preferably only one, $C_2$–$C_5$ aliphatic carboxylic acyloxy substituent; examples of the alkyl group include those exemplified above in relation to substituents B, and examples of the acyloxy group include those exemplified above in relation to substituents A; examples of these acyloxyalkyl groups include the acetoxymethyl, 1- and 2-propionyloxyethyl and 5-butyryloxypentyl groups.

Of these substituents we prefer: the halogen atoms; the hydroxy group; the alkoxy groups having from 1 to 4 carbon atoms; the aryloxy groups having from 6 to 14 carbon atoms (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); the aralkyloxy groups having from 7 to 13 carbon atoms (wherein the aryl moieties are unsubstituted or may have from 1 to 3 substituents, which may be the same or different from one another, such. as $C_1$–$C_4$ alkyl, hydroxy, halogen, $C_1$–$C_4$ alkoxy, carboxy, protected carboxy and amino substituents); the $C_2$–$C_5$ aliphatic carboxylic acyloxy groups; the $C_7$–$C_{15}$ aromatic carboxylic acyloxy groups (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); the mercapto group; the alkylthio groups having from 1 to 4 carbon atoms; the amino group; the mono- and di-$C_1$–$C_4$ alkyl-substituted amino groups; the $C_2$–$C_5$ aliphatic carboxylic acylamino groups; the nitro group; the cyano group; the carboxy group; the protected carboxy groups; the $C_1$–$C_5$ alkyl groups; the halogen-substituted $C_1$–$C_5$ alkyl groups; the $C_1$–$C_5$ hydroxyalkyl groups; and the $C_2$–$C_5$ aliphatic carboxylic acyloxy-substituted $C_1$–$C_5$ alkyl groups.

Of these, the more preferred substituents are: the halogen atoms; the hydroxy group; the alkoxy groups having from 1 to 4 carbon atoms; the aryloxy groups having from 6 to 14 carbon atoms (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); aralkyloxy groups having from 7 to 13 carbon atoms (wherein the aryl moieties are unsubstituted or may have from 1 to 3 substituents, which may be the same or different from one another, such as $C_1$–$C_4$ alkyl, hydroxy, halogen, $C_1$–$C_4$ alkoxy, carboxy, protected carboxy and amino substituents); the amino group; the mono- and di-$C_1$–$C_4$ alkyl-substituted amino groups; the $C_2$–$C_5$ aliphatic carboxylic acylamino groups; the nitro group; the cyano group; the carboxy group; the protected carboxy groups; the $C_1$–$C_5$ alkyl groups; the $C_1$–$C_5$ haloalkyl groups; the $C_1$–$C_5$ hydroxyalkyl groups; and the $C_2$–$C_5$ aliphatic carboxylic acyloxy-substituted $C_1$–$C_5$ alkyl groups.

Most preferred of all are the halogen atoms; the hydroxy group; the alkoxy groups having from 1 to 4 carbon atoms; the amino group; the mono- and di-$C_1$–$C_4$ alkyl-substituted amino groups; the $C_2$–$C_5$ aliphatic carboxylic acylamino groups; the nitro group; the $C_1$–$C_5$ haloalkyl groups; and the $C_1$–$C_5$ hydroxyalkyl groups.

Since the compounds of the present invention necessarily contain at least one carboxy group, these compounds are acids and can thus form salts and esters. There is no particular restriction upon the nature of such salts and esters, provided that, where they are intended for therapeutic use, they should be "pharmaceutically acceptable", which, as is well known to those skilled in the art, means that they should not have a reduced activity (or unacceptably reduced activity) or an increased toxicity (or unacceptably increased toxicity) as compared with the free acids. Where the compounds are intended for non-therapeutic use, for example as intermediates in the preparation of other compounds, even these restrictions do not apply.

Examples of ester groups include:

alkyl groups having from 1 to 20 carbon atoms, more preferably from 1 to 10 carbon atoms, still more preferably from 1 to 7 carbon atoms and most preferably from 1 to 5 carbon atoms, such as those exemplified above in relation to the alkyl groups which may be represented by X and higher alkyl groups as are well known in the art, such as the dodecyl, tridecyl, pentadecyl, octadecyl, nonadecyl and icosyl groups, preferably the methyl, ethyl, propyl, isopropyl, butyl, isobutyl, t-butyl and pentyl groups, but most preferably the methyl, ethyl and t-butyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents D defined and exemplified above, although the unsubstituted groups are preferred; in general, we prefer those aralkyl groups having a total of from 7 to 9 carbon atoms; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl) ethyl, benzhydryl (i.e. diphenylmethyl), triphenylmethyl, bis (o-nitrophenyl) methyl, 9-anthrylmethyl, 2,4, 6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 10 carbon atoms, more preferably from 3 to 10 carbon atoms and still more preferably from 3 to 5 carbon atoms, such as the vinyl, allyl, 2omethylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 1-octenyl, 1-nonenyl and 1-decenyl groups, of which the vinyl, allyl, 2-methylallyl, 1-propenyl, isopropenyl and butenyl groups are preferred, the allyl and 2-methylallyl groups being most preferred.

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the chloromethyl, bromomethyl, iodomethyl, fluoromethyl, trichloromethyl, trifluoromethyl, dichloromethyl, difluoromethyl, 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents D defined and exemplified above, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenyl groups, which may be unsubstituted or have at least one of substituents D defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, norcaryl, norpinanyl, norbornyl, menthenyl, camphenyl and norbornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy) ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy) ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy) ethyl, 3-pinanyloxycarbonyloxymethyl and 3-pinanylcarbonyloxymethyl groups;

5-alkyl or 5-phenyl [which may be substituted by at least one of substituents D, defined and exemplified above] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer: the alkyl esters, especially those in which the alkyl group has from 1 to 6 carbon atoms, such as the methyl, ethyl, propyl, isopropyl, butyl, isobutyl and pentyl esters; the alkenyl esters, especially those in which the alkenyl group has 3 or 4 carbon atoms, such as the allyl and methallyl esters; and aralkyl esters, in which the aralkyl group is preferably as hereinbefore defined in relation to X, such as the benzyl and phenethyl esters. Of these, the most preferred are the methyl, ethyl, allyl and benzyl esters.

Examples of pharmaceutically acceptable salts of the carboxylic acids of formula (I) include metal salts, amino acid salts and amine salts. Examples of the metal salts include: alkali metal salts, such as the sodium and potassium salts; alkaline earth metal salts, such as the calcium and magnesium salts; and other metal salts, such as the aluminum salts, iron salts, zinc salts, copper salts, nickel salts and cobalt salts. Of these we prefer the alkali metal salts, alkaline earth metal salts and aluminum salts, and most prefer the sodium salts, potassium salts, calcium salts and aluminum salts. Examples of the amino acid salts include salts with basic amino acids, such as arginine, lysine, histidine, α,γ-diaminobutyric acid and ornithine. Examples of the amine salts include t-octylamine, dibenzylamine, dicyclohexylamine, morpholine, D-phenylglycine alkyl ester and D-glucosamine salts. Of these, the sodium, potassium and calcium salts are preferred.

Preferred compounds of the present invention are:

(A) Those compounds of formula (I), in which:

R represents a hydrogen atom, a methyl group or a hydroxy group;

X represents an alkyl group having from 1 to 10 carbon atoms, an alkenyl group having from 3 to 10 carbon atoms, a cycloalkyl group having from 3 to 10 carbon atoms, a phenyl group, an aralkyl group having from 7 to 9 carbon atoms or an unsaturated heterocyclic group having 5 or 6 ring atoms, of which 1 or 2 are hetero-atoms selected from the group consisting of oxygen, sulfur and nitrogen hetero-atoms, in which said alkyl and alkenyl groups are unsubstituted or have from 1 to 4 substituents selected from the group consisting of substituents $A^1$, defined below, and said cycloalkyl, phenyl, aralkyl and heterocyclic groups are unsubstituted or have from 1 to 4 substituents selected from the group consisting of substituents B, defined above;

A represents a single bond, an alkylene group having from 1 to 10 carbon atoms, an alkenylene group having from 3 to 10 carbon atoms, an alkadienylene group having from 5 to 10 carbon atoms or an alkynylene group having from 3 to 5 carbon atoms, in which said alkylene, alkenylene, alkadienylene and alkynylene groups are unsubstituted or have 1 or 2 substituents selected from the group consisting of substituents $C^1$, defined below;

Y represents a aryl group having from 6 to 10 carbon atoms or a cycloalkyl group having from 3 to 8 carbon atoms, each of which may be unsubstituted or have 1 or 2 substituents independently selected from the group consisting of substituents $D^1$, defined below;

substituents $A^1$:

halogen atoms, hydroxy groups, alkoxy groups having from 1 to 4 carbon atoms, aliphatic carboxylic acyloxy groups having from 2 to 5 carbon atoms, amino groups, carboxy groups and protected carboxy groups;

substituents $C_1$:

halogen atoms, hydroxy groups, alkoxy groups having from 1 to 4 carbon atoms, aryloxy groups having from 6 to 14 carbon atoms, aliphatic carboxylic acyloxy groups having from 2 to 5 carbon atoms, amino groups, mono- and di-alkyl-substituted amino groups in which the or each alkyl part has from 1 to 4 carbon atoms, aliphatic carboxylic acylamino groups having from 2 to 5 carbon atoms, aromatic carboxylic acylamino groups having from 7 to 15 carbon atoms, carboxy groups and protected carboxy groups, in which the aryl groups of said aryloxy and aromatic carboxylic acylamino groups are unsubstituted or have from 1 to 3 substituents selected from the group consisting of substituents $E^1$, defined below;

substituents $D^1$ halogen atoms, hydroxy groups, alkoxy groups having from 1 to 4 carbon atoms, aryloxy groups having from 6 to 14 carbon atoms, aralkyloxy groups having from 7 to 9 carbon atoms, aliphatic carboxylic acyloxy groups having from 2 to 5 carbon atoms, aromatic carboxylic acyloxy groups having from 7 to 15 carbon atoms, mercapto groups, alkylthio groups having from 1 to 4 carbon atoms, amino groups, mono- and di-alkyl-substituted amino groups in which the or each alkyl part has from 1 to 4 carbon atoms, aliphatic carboxylic acylamino groups having from 2 to 5 carbon atoms, nitro groups, cyano groups, carboxy groups, protected carboxy groups, alkyl groups having from 1 to 5 carbon atoms, haloalkyl groups having from 1 to 5 carbon atoms, hydroxyalkyl groups having from 1 to 5 carbon atoms and acyloxyalkyl groups in which the acyl part is an aliphatic carboxylic acyl group having from 2 to 5 carbon atoms and the alkyl part has from 1 to 5 carbon atoms, in which the aryl groups of said aryloxy, aralkyloxy and aromatic carboxylic acyloxy groups are unsubstituted or have from 1 to 3 substituents selected from the group consisting of substituents $E^1$, defined below; and substituents $E^1$ alkyl groups having from 1 to 4 carbon atoms, hydroxy groups, halogen, alkoxy groups having from 1 to 4 carbon atoms, carboxy groups, protected carboxy groups and amino groups;

and pharmaceutically acceptable salts and esters thereof.

(B) Those compounds of formula (I) in which:

R and X are as defined in (A) above;

A represents an alkylene group having from 1 to 10 carbon atoms, an alkenylene group having from 3 to 10 carbon atoms, an alkadienylene group having from 5 to 10 carbon atoms or an alkynylene group having from 3 to 5 carbon atoms, in which said alkylene, alkenylene, alkadienylene and alkynylene groups are unsubstituted or have 1 or 2 substituents selected from the group consisting of substituents $C^1$, defined in (A) above; and Y represents a heterocyclic group which has 5 or 6 ring atoms of which from 1 to 3 are hetero-atoms selected from the group consisting of nitrogen, oxygen and sulfur hetero-atoms or a heterocyclic group which has 5 or 6 ring atoms of which from 1 to 3 are hetero-atoms selected from the group consisting of nitrogen, oxygen and sulfur hetero-atoms and which is fused to a benzene ring, said heterocyclic groups being unsubstituted or having 1 or 2 substituents selected from the group consisting of substituents $D^1$, defined in (A) above;

and pharmaceutically acceptable salts and esters thereof.

(C) Those compounds of formula (I) in which:

R and X are as defined in (A) above;

A represents an alkylene group having from 1 to 10 carbon atoms, an alkenylene group having from 3 to 10 carbon atoms, an alkadienylene group having from 5 to 10 carbon atoms or an alkynylene group having from 3 to 10 carbon atoms, in which said alkenylene, alkadienylene and alkynylene groups are unsubstituted or have 1 or 2 substituents selected from the group consisting of substituents $C^1$, defined in (A) above; and Y represents a hydrogen atom;

and pharmaceutically acceptable salts and esters thereof.

Still more preferred compounds of the present invention are:

(D) Those compounds of formula (I) in which:

R represents a hydrogen atom, a methyl group or a hydroxy group;

X represents an alkyl group having from 1 to 10 carbon atoms, an alkenyl group having from 3 to 10 carbon atoms or a cycloalkyl group having from 3 to 7 carbon atoms, in which said alkyl and alkenyl groups are unsubstituted or have 1 or 2 substituents selected from the group consisting of substituents $A^2$, defined below and said cycloalkyl groups are unsubstituted or have 1 or 2 substituents selected from the group consisting of substituents $B^1$, defined below;

A represents a single bond, an alkylene group having from 1 to 5 carbon atoms, an alkenylene group having from 3 to 5 carbon atoms or an alkadienylene group having from 5 to 8 carbon atoms, in which said alkylene, alkenylene and alkadienylene groups are unsubstituted or have 1 or 2 substituents selected from the group consisting of substituents $C^2$, defined below;

Y represents an aryl group having from 6 to 10 carbon atoms or a cycloalkyl group having from 5 to 7 carbon atoms, each of which may be unsubstituted or have 1 or 2 substituents independently selected from the group consisting of substituents $D^2$, defined below;

substituents $A^2$:

halogen atoms, hydroxy groups, aliphatic carboxylic acyloxy groups having from 2 to 5 carbon atoms, carboxy groups and protected carboxy groups;

substituents $B^1$:

halogen atoms, hydroxy groups, alkoxy groups having from 1 to 4 carbon atoms, aliphatic carboxylic acyloxy groups having from 2 to 5 carbon atoms, alkyl groups having from 1 to 5 carbon atoms and haloalkyl groups having from 1 to 5 carbon atoms;

substituents $C^2$:

halogen atoms, hydroxy groups, alkoxy groups having from 1 to 4 carbon atoms, amino groups, mono and di-alkyl-substituted amino groups in which the or each alkyl part has from 1 to 4 carbon atoms, and aliphatic carboxylic acylamino groups having from 2 to 5 carbon atoms; and substituents $D^2$:

halogen atoms, hydroxy groups, alkoxy groups having from 1 to 4 carbon atoms, aryloxy groups having from 6 to 14 carbon atoms, aralkyloxy groups having from 7 to 9 carbon atoms, amino groups, mono- and di-alkyl-substituted amino groups in which the or each alkyl part has from 1 to 4 carbon atoms, aliphatic carboxylic acylamino groups having from 2 to 5 carbon atoms, nitro groups, cyano groups, carboxy groups, protected carboxy groups, alkyl groups having from 1 to 5 carbon atoms, haloalkyl groups having from 1 to 5 carbon atoms, hydroxyalkyl groups having from 1 to 5 carbon atoms and acyloxyalkyl groups in which the acyl part is an aliphatic carboxylic acyl group having from 2 to 5 carbon atoms and the alkyl part has from 1 to 5 carbon atoms, in which the aryl groups of said aryloxy, aralkyloxy and aromatic carboxylic acyloxy groups are unsubstituted or have from 1 to 3 substituents selected from the group consisting of substituents $E^1$, defined in (A) above;

and pharmaceutically acceptable salts and esters thereof.

(E) Those compounds of formula (I) in which:

R and X are as defined in (D) above;

A represents an alkylene group having from 1 to 5 carbon atoms, an alkenylene group having from 3 to 5 carbon atoms or an alkadienylene group having from 5 to 8 carbon atoms, in which said alkylene, alkenylene and alkadienylene groups are unsubstituted or have 1 or 2 substituents independently selected from the group consisting of substituents $C^2$, defined in (D) above; and Y represents a heterocyclic group which has 5 or 6 ring atoms of which 1 or 2 are hetero-atoms selected from the group consisting of nitrogen and oxygen hetero-atoms or a heterocyclic group which has 5 or 6 ring atoms of which 1 or 2 are hetero-atoms selected from the group consisting of nitrogen and oxygen hetero-atoms and which is fused to a benzene ring, said heterocyclic groups being unsubstituted or having 1 or 2 substituents independently selected from the group consisting of substituents $D^2$, defined in (D) above;

and pharmaceutically acceptable salts and esters thereof.

(F) Those compounds of formula (I) in which:

R and X are as defined in (D) above;

A represents an alkylene group having from 1 to 10 carbon atoms, an alkenylene group having from 3 to 10 carbon atoms, or an alkadienylene group having from 5 to 10 carbon atoms, in which said alkenylene and alkadienylene groups are unsubstituted or have 1 or 2 substituents independently selected from the group consisting of substituents $C^2$, defined in (D) above; and Y represents a hydrogen atom;

and pharmaceutically acceptable salts and esters thereof.

Of the compounds of the invention described above, even more preferred compounds are:

(G) Those compounds of formula (I), in which:

R represents a hydrogen atom;

X represents an alkyl group having from 1 to 7 carbon atoms, an alkenyl group having from 3 to 5 carbon atoms or a cycloalkyl group having from 3 to 7 carbon atoms, said alkyl and alkenyl groups being unsubstituted or having 1 or 2 substituents independently selected from the group consisting of substituents $A^3$, defined below, and said cycloalkyl groups being unsubstituted or having at least one substituent selected from the group consisting of substituents $B^2$, defined below;

A represents a Single bond, an alkylene group having from 1 to 5 carbon atoms or an alkenylene group having from 3 to 5 carbon atoms, each of which may be unsubstituted or have 1 or 2 substituents independently selected from the group consisting of substituents $C^3$, defined below;

Y represents an aryl group having from 6 to 10 carbon atoms or a cycloalkyl group having from 5 to 7 carbon atoms, each of which may be unsubstituted or have 1 or 2 substituents independently selected from the group consisting of substituents $D^3$, defined below;

substituents $A^3$:

halogen atoms and carboxy groups;

substituents $B^2$:

halogen atoms and haloalkyl groups having from 1 to 5 carbon atoms;

substituents $C^3$:

hydroxy groups and alkoxy groups having from 1 to 4 carbon atoms;

substituents $D^3$:

halogen atoms, hydroxy groups, alkoxy groups having from 1 to 4 carbon atoms, amino groups, mono- and di-alkyl-substituted amino groups in which the or each alkyl part has from 1 to 4 carbon atoms, aliphatic carboxylic acylamino groups having from 2 to 5 carbon atoms, nitro groups, alkyl groups having from 1 to 5 carbon atoms, haloalkyl groups having from 1 to 5 carbon atoms and hydroxyalkyl groups having from 1 to 5 carbon atoms;

and pharmaceutically acceptable salts and esters thereof.

(H) Those compounds of formula (I), in which:

R and X are as defined in (G) above;

A represents an alkylene group having from 1 to 5 carbon atoms or an alkenylene group having from 3 to 5 carbon atoms, each of which may be unsubstituted or have 1 or 2 substituents independently selected from the group consisting of substituents $C^3$, defined in (G) above; and Y represents a heterocyclic group having 5 or 6 ring atoms of which 1 or 2 are hetero-atoms selected from the group consisting of nitrogen, oxygen and sulfur hetero-atoms, which may be unsubstituted or have 1 or 2 substituents independently selected from the group consisting of substituents $D^3$, defined in (G) above;

and pharmaceutically acceptable salts and esters thereof.

(I) Those compounds of formula (I), in which:

R and X are as defined in (G) above;

A represents an alkylene group having from 1 to 10 carbon atoms, an alkenylene group having from 3 to 7 carbon atoms or an alkadienylene group having from 5 to 8 carbon atoms, each of which may be unsubstituted or have 1 or 2 substituents independently selected from the group consisting of substituents $C^3$, defined in (G) above; and Y represents a hydrogen atom;

and pharmaceutically acceptable salts and esters thereof.

Still more preferred are:

(J) Those compounds of formula (I) in which:

R represents a hydrogen atom;

X represents an alkyl group having from 1 to 7 carbon atoms;

A represents an alkylene group having from 1 to 5 carbon atoms;

Y represents an aryl group having from 6 to 10 carbon atoms, or a cycloalkyl group having from 5 to 7 carbon atoms, either of which is unsubstituted or is substituted by 1 or 2 substituents selected from the group consisting of substituents $D^4$, defined below;

substituents $D^4$:

halogen atoms, hydroxy groups, alkoxy groups having from 1 to 4 carbon atoms and alkyl groups having from 1 to 5 carbon atoms;

and pharmaceutically acceptable salts and esters thereof.

The most preferred compounds of the present invention are:

(K) Those compounds of formula (I) in which:

R represents a hydrogen atom;

X represents an alkyl group having from 1 to 7 carbon atoms;

A represents an alkylene group having from 1 to 5 carbon atoms;

Y represents an aryl group having from 6 to 10 carbon atoms which is unsubstituted or is substituted by 1 or 2 substituents selected from the group consisting of substituents $D^5$, defined below;

substituents $D^5$:

halogen atoms and alkoxy groups having from 1 to 4 carbon atoms;

and pharmaceutically acceptable salts and esters thereof.

(L) Those compounds of formula (I) in which:

R, X and A are as defined in (K), above;

Y represents a heterocyclic group having 5 or 6 ring atoms of which 1 or 2 are hetero-atoms selected from the group consisting of nitrogen, oxygen and sulfur hetero-atoms, which may be unsubstituted or have 1 or 2 substituents independently selected from the group consisting of alkyl groups having from 1 to 5 carbon atoms;

and pharmaceutically acceptable salts and esters thereof.

(M) Those compounds of formula (I) in which:

R and X are as defined in (K) above;

A represents an alkylene group having from 1 to 10 carbon atoms; and

Y represents a hydrogen atom;

and pharmaceutically acceptable salts and esters thereof.

Examples of specific compounds of the invention are those compounds of formula (I) in which R, X, Y and A are as defined in the following Table 1. The compounds of the invention are hereinafter, where appropriate, identified by the numbers appended to them in this Table. In the Table, the following abbreviations are used:

| | |
|---|---|
| Ac | acetyl |
| Ada | adamantyl |
| Bdix | 1,4-benzodioxan-2-yl |
| Bfur | benzofuranyl |
| Boz | benzoyl |
| Bthi | benzothienyl |
| Bu | butyl |
| cBu | cyclobutyl |
| sBu | sec-butyl |
| tBu | t-butyl |
| Bz | benzyl |
| Chr | chromanyl |
| Chre | chromenyl |
| Dix | dioxanyl..... |
| | 1,3-Dix(5) is 1,3-dioxan-5-yl & |
| | 1,4-Dix(2) is 1,4-dioxan-2-yl |
| Et | ethyl |
| Etc | ethoxycarbonyl |
| Fur | furyl |
| Hxe | hexenyl |
| cHx | cyclohexyl |
| Ind | indolyl |
| Isox | isoxazolyl |
| Me | methyl |
| Mec | methoxycarbonyl |
| Mor | morpholino |
| Np | naphthyl |
| Ph | phenyl |
| Pin | pinanyl |
| Pip | piperidyl |
| Piz | piperazinyl |
| Pn | pentyl |
| cPn | cyclopentyl |
| tPn | t-pentyl |
| Pr | propyl |
| cPr | cyclopropyl |
| iPr | isopropyl |
| Pre | propenyl |
| iPre | isopropenyl |
| Pyr | pyridyl |
| Pyrd | pyrrolidinyl |
| Pyrr | pyrrolyl |
| Quin | quinolyl |
| iQuin | isoquinolyl |
| Tfm | trifluoromethyl |
| Thf | tetrahydrofuryl |
| Thi | thienyl |
| Thiz | thiazolyl |
| Thp | tetrahydropyranyl |
| Tht | tetrahydrothienyl |
| Tol | tolyl |

TABLE 1

| Cpd No. | R | X | Y | A |
|---|---|---|---|---|
| 1 | H | sBu | Ph | —CH₂— |
| 2 | H | tPn | Ph | —CH₂— |
| 3 | H | 3-AcO-1,1-diMePr | Ph | —CH₂— |
| 4 | H | sBu | 4-ClPh | —CH₂— |
| 5 | H | sBu | 3-HOPh | —CH₂— |
| 6 | H | sBu | 4-MeOPh | —CH₂— |
| 7 | H | CCl₃— | 3,4-diMeOPh | —CH₂— |
| 8 | H | sBu | 2,6-diMePh | —CH₂— |
| 9 | H | sBu | 2-TfmPh | —CH₂— |
| 10 | H | sBu | 3,4,5-triMeOPh | —CH₂— |
| 11 | H | sBu | 2-(HOMe)Ph | —CH₂— |
| 12 | H | tPn | 2-(HOMe)Ph | —CH₂— |
| 13 | H | tPn | 3-(HOMe)Ph | —CH₂— |
| 14 | H | sBu | 4-(AcOMe)Ph | —CH₂— |
| 15 | H | sBu | 4-NO₂—Ph | —CH₂— |
| 16 | H | sBu | Ph | — |
| 17 | H | sBu | Ph | —(CH₂)₂— |
| 18 | H | sBu | Ph | —(CH₂)₃— |
| 19 | H | iPre | 4-H₂N—Ph | —(CH₂)₂— |
| 20 | H | 1-Pre | 4-(Me)₂N—Ph | —(CH₂)₂— |
| 21 | H | tBu | 4-AcHN—Ph | —(CH₂)₂— |
| 22 | H | sBu | Ph | —(OH)CH—CH₂— |
| 23 | H | 1,1-diFPr | 4-EtcPh | —(CH₂)₃— |
| 24 | H | 1,1-diEtPr | 2-HOPh | —(CH₂)₂—(Me)CHCH₂— |
| 25 | H | Ph | 3-HSPh | —(CH₂)₅— |
| 26 | H | 2-MeOPh | 3-MeSPh | —(CH₂)₂(Me₂N)CHCH₂— |
| 27 | H | 2-HOOC—Et | 2-AcOPh | —(CH₂)₂(Me)CH(CH₂)₃(Me)CHCH₂— |
| 28 | H | sBu | Ph | —CH=CHCH₂— |
| 29 | H | 1,1-diMePn | 3,4-diMeOPh | —CH=CHCH₂— |
| 30 | H | sBu | Ph | —C≡C—CH₂— |
| 31 | H | cPr | 4-NC-Ph | —CH=CHCH₂CH=CHCH₂— |
| 32 | H | 1-Et-1-MePr | 2,6-diMeOPh | —CH₂CH=(Me)C—CH₂— |
| 33 | H | 1-NH₂-2-MePr | 2-AcOPh | —CH₂CH=(Me)C(CH₂)₂CH=(Me)CCH₂— |
| 34 | H | sBu | 1-Np | —CH₂— |
| 35 | H | 2-Fur | 5-MeO-1-Np | —CH₂— |
| 36 | H | 2,6-diMePh | 4-HOOC-Ph | —CH₂— |
| 37 | H | sBu | 3-Pyr | —CH₂— |
| 38 | H | sBu | 4-Pyr | —CH₂— |
| 39 | H | sBu | 2-Fur | —CH₂— |
| 40 | H | iPre | 3-Fur | —CH₂— |
| 41 | H | sBu | 2-Fur | —CH=CHCH₂— |
| 42 | H | 1-Etc-1-MeEt | 2-Thi | —CH₂— |
| 43 | H | 4-TfmPh | 2-Thiz | —CH₂— |
| 44 | H | (Me)₂C=CHCH₂— | 2-Pyrr | —CH₂— |
| 45 | H | sBu | 2-Thf | —CH₂— |
| 46 | H | MeCH=C(Me)— | 2-Tht | —CH₂— |
| 47 | H | sBu | 2-Thp | —CH₂— |
| 48 | H | cPn | 2-Pyrd | —CH₂— |
| 49 | H | 4-FPh | 1-Me-2-Pyrd | —CH₂— |
| 50 | H | 2,6-diMePh | 2-Pip | —CH₂— |
| 51 | H | cHx | 1-Piz | —CH₂CH₂— |
| 52 | H | cHx | Mor | —CH₂CH₂— |
| 53 | H | 4-HOPh | 1,4-Dix(2) | —CH₂— |
| 54 | H | sBu | 1,3-Dix(2) | —CH₂— |
| 55 | H | 4-HOBu | cPr | —CH₂— |
| 56 | H | 4-AcOPh | 2,2-diMe.cPr | —CH₂— |
| 57 | H | 4-iPrPh | cBu | —CH₂— |
| 58 | H | 1-F-1-MePr | cPn | —CH₂—(MeO)CH—CH₂— |
| 59 | H | 1,1-diMeBu | 2-HO.cPn | —(CH₂)₃— |
| 60 | H | sBu | cHx | —CH₂— |
| 61 | H | sBu | 4-HO.cHx | —CH₂— |
| 62 | H | tPn | 4-HO.cHx | —CH₂— |
| 63 | H | 1-Et-1-FPr | 4-tBu.cHx | —CH₂— |
| 64 | H | sBu | H | —CH₂—(Me)C=CHCH₂— |
| 65 | H | sBu | H | —(HO)CH—(Me)C=CHCH₂— |
| 66 | H | 4-AcO-1-MeBu | H | —CH₂—(Me)C=CH—(CH₂)₂—(Me)C=CHCH₂— |
| 67 | H | sBu | H | —(HO)CH—(Me)C=CH—(CH₂)₂—(Me)C=CHCH₂— |
| 68 | H | 1-Hxe | 4-Quin | —CH₂— |
| 69 | H | 3-Fur | 1-iQuin | —CH₂— |
| 70 | H | 2-Thi | 4-(2-MeOPhO)Ph | —(H₂N)CH—CH₂— |
| 71 | H | sBu | H | —(2-HOPh)OCOCH—(Me)C=CHCH₂— |
| 72 | H | sBu | H | —(Bz₂N)CH—CH₂— |

TABLE 1-continued

| Cpd No. | R | X | Y | A |
|---|---|---|---|---|
| 73 | H | 1-NH$_2$-3-Mec.Pr | 4-BozOPh | —CH$_2$—(MeO)CH—CH$_2$— |
| 74 | H | 3-Pyr | 4-PhSPh | —CH$_2$—(Mec)CH—(CH$_2$)$_2$— |
| 75 | H | Pn | 4-(2-Tol-HN)Ph | —CH$_2$—(BzO)CH—CH$_2$— |
| 76 | H | sBu | H | -(4-FPhO)CH—(AcO)CH—CH$_2$— |
| 77 | H | 4-HOOC.Bu | 3-PhSPh | —(Cl)CH—(CH$_2$)$_4$— |
| 78 | H | 2-EtcPh | 3-PhOPh | —CH$_2$— |
| 79 | H | sBu | 2-Bfur | —CH$_2$— |
| 80 | H | sBu | 2-Bfur | —CH=CHCH$_2$— |
| 81 | H | sBu | 2-Chr | —CH$_2$— |
| 82 | H | 4-Pyr | 2-Bthi | —CH$_2$— |
| 83 | H | 4-ClPh | 3-Ind | —CH$_2$— |
| 84 | H | 1-EtPr | 2,3-dihydro-2-Bfur | —CH$_2$— |
| 85 | H | sBu | 2-Chre | —(BozO)CH—CH$_2$— |
| 86 | H | sBu | Bdix | —CH$_2$— |
| 87 | H | iPre | 3-Pin | —CH$_2$— |
| 88 | H | 3-HO-2-Me-1-Pre | 1-Ada | —(AcHN)CH—CH$_2$— |
| 89 | Me | sBu | Ph | —CH$_2$— |
| 90 | Me | tPn | Ph | —CH$_2$— |
| 91 | Me | 1,1-diFPr | 3-HOPh | —CH$_2$— |
| 92 | Me | sBu | 3,4-diMeOPh | —(CH$_2$)$_3$— |
| 93 | Me | 1,1-diEtPr | 2-HOMePh | —CH$_2$— |
| 94 | Me | sBu | 3-AcOMePh | —CH=CHCH$_2$— |
| 95 | Me | 1-F-1-MePr | 3-Pyr | —CH$_2$— |
| 96 | Me | tPn | 2-Fur | —CH$_2$— |
| 97 | Me | 3-HO-1,1-diMePr | 2-Fur | —CH=CHCH$_2$— |
| 98 | Me | tBu | 2-Thf | —CH$_2$— |
| 99 | Me | 1-EtBu | Mor | —(CH$_2$)$_2$— |
| 100 | Me | iPre | 1,3-Dix(5) | —CH$_2$— |
| 101 | Me | 4-Etc-1-MeBu | 4-HO.cHx | —CH$_2$— |
| 102 | Me | 1-Cl-1-MePr | 4-HO.cHx | —CH$_2$— |
| 103 | Me | sBu | H | —CH$_2$—(Me)C=CHCH$_2$— |
| 104 | Me | tPn | H | —(HO)CH—(Me)C=CHCH$_2$— |
| 105 | Me | sBu | H | —(PhO)CH—CH$_2$— |
| 106 | Me | iPre | H | -(4-MeOBzO)CH—CH$_2$— |
| 107 | Me | 1,1-diMe-4-HOBu | 2-Bfur | —CH$_2$— |
| 108 | Me | sBu | Bdix | —CH$_2$— |
| 109 | OH | sBu | Ph | —CH$_2$— |
| 110 | OH | tPn | Ph | —CH$_2$— |
| 111 | OH | 1-Et-1-MePr | 2-TfmPh | —CH$_2$— |
| 112 | OH | 1,1-diFPr | 2-AcOMePh | —CH$_2$— |
| 113 | OH | sBu | 3-Pyr | —CH$_2$— |
| 114 | OH | sBu | 2-Fur | —CH$_2$— |
| 115 | OH | 2-MeOEt | 2-Fur | —CH=CHCH$_2$— |
| 116 | OH | MeCH=C(Me)— | cHx | —CH$_2$— |
| 117 | OH | sBu | H | —CH$_2$—(Me)C=CHCH$_2$— |
| 118 | OH | sBu | H | —(BzO)CH—(Me)C=CHCH$_2$— |
| 119 | H | sBu | 3-TfmPh | —CH$_2$— |
| 120 | H | sBu | 3-HOMePh | —CH$_2$— |
| 121 | H | sBu | 2-HOPh | —(CH$_2$)$_2$— |
| 122 | H | sBu | Mor | —(CH$_2$)$_2$— |
| 123 | H | sBu | 4-Tol | —CH$_2$— |
| 124 | H | sBu | 2,5-diMePh | —CH$_2$— |
| 125 | H | sBu | 2-(1-HO-1-MeEt)Ph | —CH$_2$— |
| 126 | H | sBu | 2-EtOPh | —CH$_2$— |
| 127 | H | sBu | 4-BuOPh | —CH$_2$— |
| 128 | H | sBu | 5-Isox | —CH$_2$— |
| 129 | H | sBu | 4-FPh | —CH$_2$— |
| 130 | H | sBu | 1,3-Dix(5) | —CH=CHCH$_2$— |
| 131 | H | sBu | 4,6-diMe-1,3-Dix(5) | —CH$_2$— |
| 132 | H | sBu | 3-MeOPh | —CH$_2$— |
| 133 | H | sBu | 4-BrPh | —CH$_2$— |
| 134 | H | sBu | 4-HOMePh | —CH$_2$— |
| 135 | H | sBu | 2-ClPh | —CH$_2$— |
| 136 | H | sBu | 2,6-diClPh | —CH$_2$— |
| 137 | H | sBu | 2-Thi | —CH$_2$— |
| 138 | H | sBu | 4-Isox | —CH$_2$— |
| 139 | H | sBu | 5-Me-3-Isox | —CH$_2$— |
| 140 | H | sBu | 3-Me-5-Isox | —CH$_2$— |
| 141 | H | sBu | 3,5-diMe-4-Isox | —CH$_2$— |
| 142 | H | sBu | H | —(CH$_2$)$_6$— |

Of the compounds listed above, preferred compounds are Compounds Nos. 1, 6, 17, 18, 39, 45, 47, 54, 60, 61, 122, 123, 124, 126, 128, 129, 132, 134, 135, 136, 137, 138, 139, 140, 141 and 142; and more preferred compounds are Compounds Nos. 1, 39, 54, 126, 135, 136, 137, 138, 139, 140, 141 and 142.

The most preferred specific compounds are Compounds Nos.

1. 7-[5-Benzyloxyimino-2-methyl-8-(2-methylbutyryloxy)-3-oxo-1,2,3,5,6,7,8,8a-octahydro-1-naphthyl]-3-hydroxy-5-oxoheptanoic acid;

54. 7-[5-(1,3-Dioxan-5-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid;

137. 7-[5-(2-Thienyl)methoxyimino-2-methyl-8-(2-methylbutyryloxy)-3-oxo-1,2,3,5,6,7,8,8a-octahydro-1-naphthyl]-3-hydroxy-5-oxoheptanoic acid;

138. 7-[5-(Isoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid;

139. 7-[5-(5-Methylisoxazol-3-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid;

140. 7-[5-(3-Methylisoxazol-5-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid;

141. 7-[5-(3,5-Dimethylisoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid;

and pharmaceutically acceptable salts and esters (especially allyl and benzyl esters) thereof.

The compounds of the present invention contain or can contain several asymmetric carbon atoms, and these can give rise to various optical isomers. Also, because of the presence of the oxime moiety (=NO—A—Y), syn and anti stereoisomers exist for all of the compounds of the invention, both the free acids of formula (I) and their salts and esters. Although these isomers are all represented herein by a single plane formula, it will be understood that the present invention contemplates both the individual isolated isomers and mixtures thereof. If the compounds are prepared by stereospecific synthesis techniques, individual isomers may be prepared. Otherwise, a mixture of isomers may normally be obtained. In this case, the mixture of isomers as such may be used or the individual isomers may be separated by well known resolution techniques.

The compounds of the present invention can be prepared by a variety of methods, whose general techniques are known in the art for the preparation of compounds of this type. For example, they may be prepared by oxidizing a compound of formula (II):

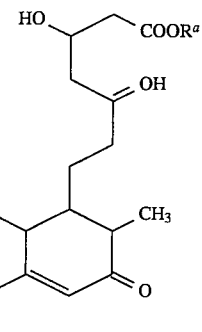

(in which X, Y, R and A are as defined above, and $R^a$ represents an alkyl, alkenyl or aralkyl group, as defined and exemplified above in relation to the ester groups), to give a compound of formula (III):

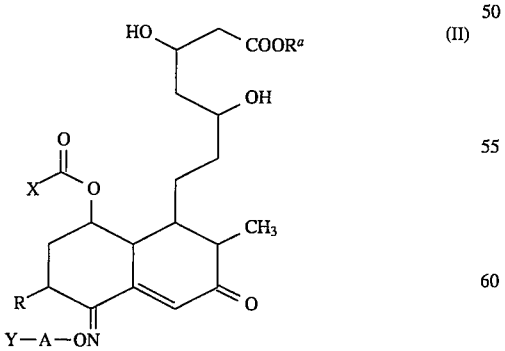

(in which X, Y, R, $R^a$ and A are as defined above), and, if desired, de-esterifying the compound of formula (III) to give a compound of formula (I), and, if desired, converting said compound of formula (III) or (I) to any other ester or to a salt.

In more detail, a suggested procedure for the preparation of the compounds of the present invention is illustrated in the following Reaction Scheme:

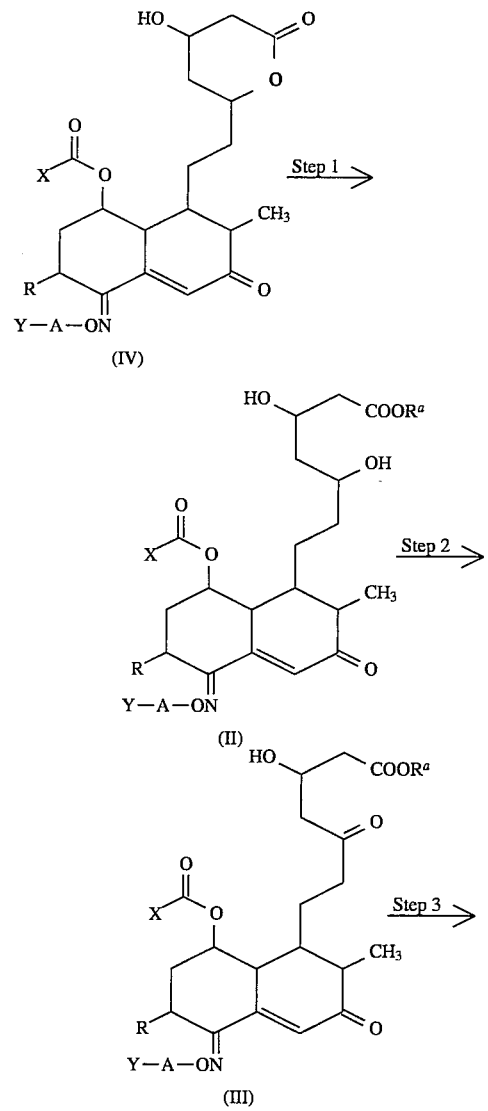

-continued

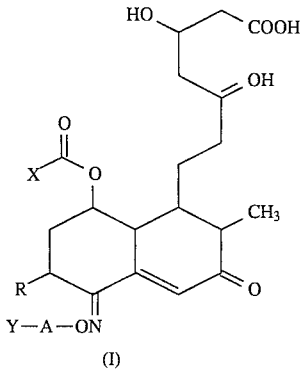

In the above formulae, X, Y, R, $R^a$ and A are as defined above.

The compound of formula (IV) used as a starting material in this reaction scheme is known and may be prepared as described in European Patent Publication No. 314 435, the disclosure of which is incorporated herein by reference, or as described in greater detail below.

In Step 1 of this reaction scheme, the lactone ring of a compound of formula (IV) is subjected to ring-opening hydrolysis, and then the product is esterified, both by known procedures, to give a compound of formula (II).

The lactone ring opening reaction is performed by contacting the compound of formula (IV) with at least an equimolar amount, and preferably a greater than equimolar amount of an alkali, for example an alkali metal hydroxide, such as sodium hydroxide, potassium hydroxide or lithium hydroxide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol, ethanol, propanol or ethylene glycol; ethers, such as tetrahydrofuran; or a mixture of water with any one or more of these organic solvents.

The reaction can take place over a wide range of temperatures, and the precise reaction temperature is not critical to the invention. In general, we find it convenient to carry out the reaction at a temperature of from 0° C. to 100° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 3 to 48 hours, more preferably from 5 to 24 hours, will usually suffice.

The esterification step may be carried out by removing the solvent from the reaction mixture, and then contacting a metal salt of the resulting carboxylic acid with an active esterifying agent appropriate to the desired group $R^a$, for example an alkyl halide, alkenyl halide or aralkyl halide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: amides, especially formamide compounds, such as dimethylformamide; ethers, such as tetrahydrofuran; dialkyl sulfoxides, such as dimethyl sulfoxide; and ketones, such as acetone. Alternatively, a metal salt of the resulting carboxylic acid may be dissolved in an aqueous solvent and converted to the free carboxylic acid by the addition of a mineral acid (for example hydrochloric acid), and then the carboxylic acid is contacted with a diazoalkane, which is preferably used in the form of an ethereal solution.

In Step 2, the compound of formula (II) obtained as described in Step 1 is converted to the corresponding ester compound of the present invention having the formula (III). The reaction may be conducted by contacting a compound of formula (II) with an oxidizing agent by conventional means. Examples of suitable oxidizing agents include: organic active halogen compounds, such as N-bromoacetamide, N-chlorosuccinimide or N-bromophthalimide; or an oxidizing system, such as dimethyl sulfoxide in association with dicyclohexyl carbodiimide, dimethyl sulfoxide in association with oxalyl chloride, dimethyl sulfoxide in association with trifluoroacetic anhydride, dimethyl sulfoxide in association with pyridine and anhydrous sulfuric acid, pyridinium chlorochromate, pyridinium dichromate or silver carbonate in association with a Celite (trade mark) filter aid.

When dimethyl sulfoxide in association with dicyclohexyl carbodiimide is employed, an acid catalyst, such as phosphoric acid or trifluoroacetic acid, is preferably also used. When dimethyl sulfoxide in association with oxalyl chloride, dimethyl sulfoxide in association with trifluoroacetic anhydride or dimethyl sulfoxide in association with pyridine and anhydrous sulfuric acid is employed, the reaction is preferably carried out in the presence of a basic catalyst, such as a tertiary alkylamine (for example triethylamine).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent, and so the preferred solvents will depend on the nature of the oxidizing system employed. For example, when an organic active halogen compound is used, examples of suitable solvents include: aqueous organic solvents, such as aqueous alcohols (for example t-butanol), aqueous ketones (for example acetone) or aqueous amines (for example pyridine). When dimethyl sulfoxide in association with dicyclohexylcarbodiimide, dimethyl sulfoxide in association with oxalyl chloride, dimethyl sulfoxide in association with trifluoroacetic anhydride, dimethyl sulfoxide in association with pyridine and anhydrous sulfuric acid, pyridinium chlorochromate, pyridinium dichromate or silver carbonate in association with Celite is used, suitable solvents include, for example: sulfoxides, such as dimethyl sulfoxide; aromatic hydrocarbons, such as benzene or toluene; and halogenated hydrocarbons, especially halogenated aliphatic hydrocarbons, such as methylene chloride or chloroform.

The reaction can take place over a wide range of temperatures, and the precise reaction temperature is not critical to the invention, although the preferred temperature will vary depending upon the nature of the oxidizing agent used. In general, if dimethyl sulfoxide in association with oxalyl chloride or dimethyl sulfoxide in association with trifluoroacetic anhydride is used, we find it convenient to carry out the reaction at a temperature of from −78° C. to 40° C., more preferably from −50° C. to about room temperature: if silver carbonate in association with Celite is used, a suitable temperature is from 0° C. to 100° C., more preferably from room temperature to 100° C.; if any of the other oxidizing agents is used, a suitable temperature is from 0° C. to 50° C., more preferably from 10° C. to 30° C. The time required for the reaction may also vary widely, depending on many factors, notably the reaction temperature and the nature of the reagents and solvent employed. However, provided that the reaction is effected under the preferred conditions outlined above, a period of from 10 minutes to 12 hours will usually suffice.

After completion of the reaction, the desired compound can be collected from the reaction mixture by conventional means. For example, one suitable recovery procedure comprises: adding a water-immiscible organic solvent to the reaction mixture, in order to extract the desired compound; the organic layer is then washed with water, and the solvent is distilled off to obtain the desired compound. If necessary, the desired compound can be further purified by conventional means such as recrystallization, reprecipitation or the various chromatography techniques, notably column chromatography.

Step 3 is an optional step, in which a carboxylic acid of formula (I) or a salt thereof may be prepared.

The reaction for obtaining a carboxylic acid is carried out by treating an ester compound of formula (III) in a similar manner to that described above in Step 1, where a lactone compound of formula (IV) is hydrolyzed. For example, the reaction may be performed by contacting the ester compound of formula (III) with at least an equimolar amount, and preferably a greater than equimolar amount, of an alkali, for example an alkali metal compound, such as sodium hydroxide, potassium hydroxide or lithium hydroxide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol, ethanol, propanol or ethylene glycol; ethers, such as tetrahydrofuran or dioxane; or a mixture of water with any one or more of these organic solvents.

The reaction can take place over a wide range of temperatures, and the precise reaction temperature is not critical to the invention. In general, we find it convenient to carry out the reaction at a temperature of from 0° C. to 100° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 3 to 48 hours, more preferably from 5 to 24 hours, will usually suffice.

After completion of the reaction, the reaction solution is made to be acidic by the addition of a mineral acid (for example hydrochloric acid). The free carboxylic acid may then be extracted by the addition of a water-immiscible organic solvent. The extract may then be washed with water, and the desired carboxylic acid is obtained from the extract by removal of the solvent. If necessary, the desired carboxylic acid can be further purified by conventional means such as recrystallization, reprecipitation or the various chromatography techniques, notably column chromatography.

Alternatively, a carboxylic acid of formula (I) can be prepared by reacting an ester compound of formula (III) in which $R^a$ represents an alkenyl group with a proton donor in the presence of a palladium complex in an inert solvent. Such a reaction is now well known and the reagents employed may be as used for known reactions of this type. For example, suitable palladium complexes which may be employed include complexes in which 0 valent palladium is coordinated to an organic phosphorus compound, such as triphenylphosphine, tributylphosphine or triethyl phosphite, preferably tetrakis(triphenylphosphine)palladium(O).

Suitable proton donors include, for example: organic carboxylic acids, such as formic acid, acetic acid or benzoic acid; phenols, such as phenol or cresol; and active methylene compounds, such as diethyl malonate or ethyl acetoacetate. Of these, we prefer the organic carboxylic acids.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, including aliphatic and aromatic hydrocarbons, such as hexane or benzene; halogenated hydrocarbons, especially halogenated aliphatic hydrocarbons, such as methylene chloride or chloroform; ethers, such as diethyl ether, tetrahydrofuran or dioxane; alcohols, such as methanol, ethanol or t-butanol; ketones, such as acetone or methyl ethyl ketone; esters, such as methyl acetate or ethyl acetate; amides, such as dimethylformamide or dimethylacetamide; and sulfoxides, such as dimethyl sulfoxide. Of these, we prefer the ethers. A single one of these solvents or a mixture of any two or more of them may be employed.

The reaction is preferably conducted in the absence of oxygen, for example in a stream of nitrogen. The reaction can take place over a wide range of temperatures, and the precise reaction temperature is not critical to the invention. In general, we find it convenient to carry out the reaction at a temperature of from 0° C. to 40° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours will usually suffice. The reaction is preferably effected with stirring or by allowing the reaction mixture to stand.

After completion of the reaction, the desired compound obtained in each reaction can be recovered from the reaction mixture by conventional means. For example, one suitable recovery procedure comprises: cooling the reaction solution and separating the crystals obtained by filtration: alternatively, any insoluble matter is removed by filtration, water is added, and then the mixture is extracted with a water-immiscible organic solvent; alternatively, water is added, the aqueous layer is acidified, and then the mixture is extracted with a water-immiscible organic solvent. The resulting compound can, if necessary, be further purified by conventional means such as recrystallization, reprecipitation or the various chromatography techniques, notably column chromatography.

Alternatively, a carboxylic acid of formula (I) can be prepared by catalytic reduction of an ester compound of formula (III) in which $R^a$ represents an aralkyl group, in the presence of hydrogen. The pressure of hydrogen employed is preferably from 1 to 5 atmospheres.

Examples of suitable catalysts which may be employed include palladium-on-carbon, platinum oxide and Raney nickel, of which we prefer palladium-on-carbon.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as diethyl ether, tetrahydrofuran or dioxane; amides, such as dimethylformamide or dimethylacetamide; and aqueous organic solvents, for example an aqueous organic carboxylic acid such as aqueous formic acid or aqueous acetic acid. Of these, we prefer to use an aqueous organic acid or an alcohol. The reaction can take place over a wide range of temperatures, and the precise reaction temperature is not critical to the invention. In general, we find it convenient to carry out the reaction at a temperature of from 0° C. to 50° C., more preferably from about room temperature to 40° C. The time required for the reaction may also vary widely, depending on many factors, notably the reaction temperature and the nature of the reagents and solvent employed. However, provided that the reaction is effected under the preferred conditions outlined above, a period of from 1 to 6 hours will usually suffice.

After completion of the reaction, the reaction mixture may be filtered to remove the catalyst, and the solvent may then be removed, for example by distillation, to obtain the desired compound. If necessary, the resulting compound can be further purified by conventional means such as recrystallization, reprecipitation or the various chromatography techniques, notably column chromatography.

A metal salt of the carboxylic acid of formula (I) can be prepared by conting the carboxylic acid with a metal hydroxide or carbonate of the metal whose salt is to be prepared, for example sodium hydroide, potassium hydroxide, calcium hydroxide or sodium carbonate, in water or in a suitable aqueous organic solvent, such as aqueous alcohol, aqueous acetone or aqueous dioxane. The amount of the metal compound is not critical, although it is best to use an equimolar amount or greater with respect to the carboxylic acid, so as to minimise waste of the carboxylic acid. In general, we prefer to use from 1 to 1.5 mole of the metal hydroxide or metal carbonate per mole of the carboxylic acid.

After completion of the reaction, the desired compound can be obtained from the reaction mixture by conventional means. For example, the desired compound can be recovered from the reaction mixture by distilling the solvent off under reduced pressure, and then freeze-drying the mixture. The resulting compound can, if necessary, be further purified by conventional means such as recrystallization, reprecipitation or the various chromatography techniques, notably column chromatography.

As mentioned above, compounds of formula (IV), which are used as the starting material in the above reaction schem, are known and have been described in Japanese Patent Kokai Application No. Sho 58-55443 (European Patent Publication No. 76601) and in Japanese Patent Kokai Application No. Hei 2-255 (European Patent Publication No. 314 435) and can be prepared according to the methods described in these patents. The starting materials, ML-236B, MB-530B, M-4 and M-4', which may be used for preparing compounds of formula (IV), are also described in Japanese Patent Kokai Application No. Sho 58-55443 and Japanese Patent Kokai Application No. Hei 2-255, but may also be obtain by cultivating the microorganisms mentioned below.

An example of a strain of microorganism capable of producing ML-236B is *Penicillium citrinum* Thom SANK 13380 which belongs to the genus Penicillium and has been deposited under the terms of the Budapest Treaty at the Research Institute of Microbiological Technology, Agency of Industrial Science & Technology, Ministry of Internal Trade and Industry, Tokyo, Japan, under the Deposition Number FERM BP-4129: Date of Deposition, 22nd, Dec., 1992).

The mycological properties of Strain SANK 13380 are as follows.

Colonies on Czapek yeast autolysate agar (CYA) medium were 1.8 cm in diameter after growth for 7 days at 25° C. The surface colors were white (1 A 1) to light yellow (2 A 4), and the surface was covered with white, floccose aerial hyphae. The reverse was colored white (1 A 1) to light yellow (2 A 4), and radial creases were observed. Neither exudates nor soluble pigments were found.

Colonies on malt extract agar (MEA) medium were 1.3 cm in diameter (after growth at 25° C. for 7 days). The surface was colored pale yellow (2 A 3), and the surface appearance varied from velvety to powdery. The reverse was colored brownish orange (7 C 7).

Colonies on 25% w/v glycerol nitrate agar (G25N) medium were 1.6 cm in diameter (after growth at 25° C. for 7 days). The surface colors ranged from white (1 A 1) to yellowish white (1 A 2), and the surface was covered with floccose hyphae. The reverse was colored pale yellow (2 A 3).

No growth was observed on any of these media at 5° C. or 37° C.

The surfaces of conidiophores are smooth, and biverticillate. Metulae are cylindrical with slightly vesiculate, and 9–15×3–4 µm in size. Phialides are ampulliform, and 8–10× 3–4 µm in size. Conidia are globose, and the surfaces are smooth to slightly rough, 2.5 to 4 µm in diameter.

On comparing these properties with those of known species, the properties of this strain were found to accord with those of *Penicillium citrinum* Thom described by J. I. Pitt in "The genus Penicillium and its teleomorpholic states, Eupenicillium and Talaromyces", p 634, Academic Press (1979). Accordingly, this strain was identified as *Penicillium citrinum* Thom.

The description of the color tones follows the guidelines of A. Kornerup and H. H. Wansher in "Methuen Handbook of Colour", 3rd Ed. (1978) Published by Eyre Methuen (London).

It will be appreciated that SANK 13380, or any other strain capable of producing ML-236B, may be sub-cultured or biotechnologically altered or modified to produce an organism with different characteristics. The only requirement is that the resulting organism be capable of producing the required compound. Alterations may occur naturally or artificially, by induction, for example by ultraviolet radiation, high frequency waves, radiation and chemical mutagens.

Such alterations and modifications may take any desired form, or may be consequent on such considerations as, for example, culture conditions. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in Penicillium spp. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring Penicillium plasmid and inserting a desired gene or genes from another source. Natural plasmids may also be modified in any other manner that may be considered desirable.

Any such modified strain may be employed in the process of the present invention, provided only that the strain is capable of producing ML-236B, a matter which can readily be ascertained by simple and routine experimentation.

In order to obtain ML-236B from a culture of a suitable microorganism, the microorganism should be fermented in a suitable medium. Such media are generally well known in the art, and will frequently be of a type commonly used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism.

Suitable carbon sources include any carbon-containing material which is assimilable by the microorganism, for example: carbohydrates, such as glucose, fructose, maltose, lactose, sucrose, starch, mannitol, dextrin, glycerin, thick malt syrup, molasses, blackstrap molasses, oat powder, rye powder, corn starch, potato, corn powder, soybean powder, or malt extract; oils or fats, such as soybean oil, cotton seed oil, olive oil, cod-liver oil, or lard oil; organic acids, such as citric acid, sodium ascorbate, malic acid, acetic acid, fumaric acid, tartaric acid, succinic acid or gluconic acid; alcohols, such as methanol, ethanol, propanol, isopropanol, butanol, isobutanol, or t-butanol; and amino acids, such as glutamic acid. These substances can be used alone or a mixture of any two or more of them may be used. Typical amounts will be in a range from about 1 to 10% w/v of the amount of medium, although the amount may be varied as desired and in accordance with the desired result.

Suitable nitrogen sources include any nitrogen-containing material which is assimilable by the microorganism, for example any substance containing a protein, or other readily assimilable source of nitrogen. Representative examples of nitrogen sources are: organic nitrogen sources from animals and plants, and may be extracts from such natural sources as soybean meal, wheat bran, wheat germ, peanut meal, cottonseed meal, cottonseed oil, soy protein isolate, casamino acid, casein hydrolysate, fermamine, fish meal, corn steep liquor, peptone, meat extract, yeast, yeast autolysate, yeast extract, malt extract and urea; amino acids, such as aspartic acid, glutamine, cystine, or alanine; ammonium salts, such as ammonium sulfate, ammonium nitrate, ammonium chloride or ammonium phosphate; and inorganic nitrogen compounds, such as sodium nitrate or potassium nitrate. As with the carbon source, these may be employed alone or in any combination. Suitable amounts are typically within a range from about 0.2 to 6% w/v of the amount of medium.

Suitable nutrient inorganic salts are those which provide trace elements as well as the major constituent of the salt. Preferably, salts should provide such ions as sodium, potassium, magnesium, ammonium, calcium, phosphate, sulfate, chloride, or carbonate in an assimilable form, and preferably such trace metals as molybdenum, boron, copper, cobalt, manganese and iron. Examples of suitable compounds include: sodium chloride, manganese chloride, cobalt chloride, potassium chloride, calcium chloride, calcium carbonate, aluminum potassium sulfate, manganese sulfate, cupric sulfate, cobalt sulfate, zinc sulfate, ferrous sulfate, magnesium sulfate, monopotassium phosphate, dipotassium phosphate, disodium phosphate, or ammonium molybdate. In addition, any other additives necessary for the growth of the microorganism and for promoting the formation of ML-236B may be used in any suitable combination.

Addition of a sulfur compound assimilable by the microorganism from the medium may sometimes elevate production of the desired compound. Suitable sulfur compounds include inorganic sulfur compounds including: sulfates, such as zinc sulfate, cupric sulfate, ferrous sulfate or ammonium sulfate; thiosulfates, such as ammonium thiosulfate; and sulfites, such as ammonium sulfite; or organic sulfur compounds including: sulfur-containing amino acids, such as cystine, cystein, or L-thiazoline-4-carboxylic acid; heavy metal sulfate compounds, such as ferrous sulfate or cupric sulfate: vitamins, such as vitamin $B_1$ or biotin; and bacterial growth promoting factors, such as thiamine.

An antifoaming agent such as a silicone oil, a polyalkylene glycol ether, a vegetable oil, or suitable surfactant may be added to the medium. Such addition may be particularly appropriate when the microorganism is fermented as a liquid culture.

It is preferred that the pH of the culture medium for the cultivation of *Penicillium citrinum* Thom SANK 13380, when used for the production of ML-236B, should be maintained in the region of pH 5.0 to pH 8.0, more preferably from pH 6.0 to pH 7.0, although the only requirement is that the pH should not prevent growth of the microorganism, or adversely irreversibly affect the quality of the final product.

*Penicillium citrinum* Thom SANK 13380 will, in general, grow at temperatures ranging from 15° C. to 35° C., and grow well at from 22° C. to 30° C. Other temperatures not falling within these ranges may be applicable where a strain has been developed which can grow at lower or higher temperatures, or for other special purposes, as is well known in the art. For the production of ML-236B, a preferable temperature is between 22° C. and 26° C., more preferably about 24° C.

There is no particular restriction on the culture technique used for the preparation of ML-236B, and any culture method commonly used for bacterial growth may equally be used here. However, ML-236B is ideally obtained by aerobic culture, and any suitable aerobic culture techniques, such as, for example, solid culture, stirring culture, stationary culture, shaking culture or aeration-agitation culture may be employed.

If the culture is conducted on a small scale, then a shaking culture fermented for several days at from 20° C. to 30° C., more preferably about 24° C., is generally preferred.

To start a fermentative culture, a preferred technique employs an initial inoculum prepared in one or two steps, for example, in an Erlenmeyer flask, which is preferably provided with baffles (a water flow controlling wall). A carbon source and a nitrogen source may be used in combination for the culture medium. The seed flask is shaken in a thermostatic incubator at a suitable temperature, for example from 22° C. to 26° C., more preferably at about 24° C., for a suitable period, normally from 2 to 7 days, or until sufficient growth is observed, preferably from 3 to 5 days. The resulting seed culture may then be used to inoculate a second seed culture, or a production culture. If a second seeding is conducted, this may be performed in a similar manner, and partly used for inoculation to the production medium. The flask into which the seed culture is inoculated is shaken for a suitable period, for example from 2 to 7 days, or until maximal production is obtained, at a suitable temperature, for example 24° C. When incubation is complete, the contents of the flask may be collected by centrifugation or filtration.

If the culture is to be performed on a large scale, cultivation in a suitable aeration-agitation fermenter may be preferable. In this procedure, the nutrient medium can be prepared in a fermenter. The medium is first sterilized at a suitably high temperature, for example about 120° C., after which it is cooled and seeded with an inoculum previously grown on a sterilized medium. The culture is preferably performed at a temperature from 20° C. to 26° C., preferably from 22° C. to 24° C., with stirring and aeration. This procedure is suitable for obtaining a large amount of the compound.

The amount of the ML-236B produced by the culture with the passage of time can be monitored by sampling and assessing the content of ML-236B by, for example, high performance liquid chromatography. ML-236B can exist in both the lactone and hydroxy forms, and will usually be produced as a mixture of these forms. It is possible to determine the amounts of each form at the same time. In general, the amount of ML-236B produced reaches a maximum after a period of time of between 72 hours and 300 hours.

The ML-236B produced by the culture exists both in the culture filtrate and in the bacterial cells. ML-236B can exist in either the hydroxy-acid form or the lactone form each of which can change to the other. In addition, the hydroxy-acid form can form a corresponding salt, which will be stable.

Therefore, ML-236B can be extracted and collected directly by using this property in combination with other properties, for example, as follows.

Method 1

The bacterial cells and other solid materials in the medium are centrifuged or filtered using a filter aid such as diatomaceous earth to separate it into the supernatant and bacterial cells.

(1) Supernatant

The lactone ring in the lactone form of the molecule of ML236B existing in the supernatant is hydrolyzed under alkaline conditions (preferably at pH 12 or higher) whereby it opens and all of the ML-236B is converted into the hydroxy-acid salt form. The salt is then converted into the corresponding free hydroxy-acid by careful acidification; and then the ML-236B is obtained from this mixture as the free hydroxy-acid by extraction with a water-immiscible organic solvent, for example: an aliphatic hydrocarbon, such as hexane or heptane; an aromatic hydrocarbon, such as benzene, toluene or xylene; a halogenated hydrocarbon, such as methylene chloride, chloroform, carbon tetrachloride, dichloroethane, chlorobenzene or dichlorobenzene; an ether, such as diethyl ether or diisopropyl ether; or an ester, such as ethyl formate, ethyl acetate, propyl acetate, butyl acetate or diethyl carbonate. A single one of these solvents or a mixture of any two or more of them may be used.

(2) Bacterial cells

The bacterial cells are mixed with a water-miscible organic solvent, for example: an alcohol, such as methanol or ethanol; a ketone, such as acetone; a nitrile, such as acetonitrile or isobutyronitrile; an amide, such as dimethylformamide, dimethylacetamide, $\underline{N}$-methyl-2-pyrrolidone, $\underline{N}$-methylpyrrolidinone or hexamethylphosphoric triamide. The final concentration of bacterial cells in the resulting mixture is preferably from 50% to 90%. The resulting mixture is preferably then treated in a similar manner to that described above for the supernatant, to obtain the free hydroxy-acid.

Method 2

The culture medium is treated under alkaline conditions (preferably at pH 12 or higher), with heating or at room temperature, to destruct the cells, and to hydrolyze and to open the lactone ring in the molecule. At that time, all of the ML-236B is converted into its hydroxy-acid salt form. ML-236B in the free hydroxy-acid form is obtained after conversion of the salt form into its corresponding free hydroxy-acid form by a similar treatment to that described above for the supernatant in Method 1.

The resulting free hydroxy-acid form can be dissolved in the form of a salt in an aqueous solution of an alkali metal base, for example, an alkali metal hydroxide such as sodium hydroxide. Furthermore, the free hydroxy-acid form can be converted into a salt which is easily obtainable and most stable.

Alternatively, the resultant free hydroxy-acid form can be converted into its lactone form by dehydration with heating or by ring closure in an organic solvent.

Isolation and purification of the free hydroxy-acid, hydroxy-acid salt and lactone forms thus obtained can be effected by conventional means commonly used for the isolation and purification of organic compounds. Examples of such methods include a method using a synthetic adsorbent, such as partition chromatography using a carrier, Sephadex LH-20 (trade mark for a product of Pharmacia), Amberlite XAD-11 (trade mark for a product of Rohm and Haas) or Diaion HP-20 (trade mark for a product of Mitsubishi Chem. Ind.). Alternatively, it may be isolated and purified using ordinary phase or reverse phase column chromatography using silica gel or alkylated silica gel (preferably high performance liquid chromatography), followed by elution with a suitable solvent.

The lactone form can be also purified by adsorption column chromatography using a carrier such as silica gel, alumina, or Florisil (a trade mark for a carrier of magnesium—silica gel type).

Examples of solvents which may be employed as the eluent include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; and ethers, such as diethyl ether, diisopropyl ether, tetrahydrofuran, dioxane, dimethoxyethane or diethylene glycol dimethyl ether.

Alternatively, it can be obtained by passing the extracted solution through a column using an adsorbent to remove impurities; or by adsorption of the free hydroxy-acid form on such a column, followed by elution with an aqueous alcohol, such as aqueous methanol, aqueous ethanol, aqueous butanol or aqueous isopropanol, or an aqueous ketone, such as aqueous acetone. Suitable adsorbing agent which may be employed include active carbon, or an adsorbing resin such as Amberlite XASD-2, XAD-4 (trade mark for a product of Rohm and Haas) or Diaion HP-10, HP-20, CHP-20, HP-50 (trade mark for a product of Mitsubishi Chem. Ind.).

The free hydroxy-acid and the salt of the hydroxy-acid can be convered into each other by conventional means, and purified in any desired form.

ML-236B can also be prepared chemically by the methods described in the literature below.

1) D. J. Clive et al.: J. Am. Chem. Soc. 112, 3018 (1990)
2) C. T. Hsu et al.: J. Am. Chem. Soc. 105, 593 (1983)
3) N. N. Girotra et al.: Tetrahedron Lett. 23, 5501 (1982) Tetrahedron Lett. 24, 3687 (1983) Tetrahedron Lett. 25, 5371 (1984)
4) M. Hirama et al.: J. Am. Chem. Soc. 104, 4251 (1982)
5) P. A. Grieco et al.: J. Am. Chem. Soc. 108, 5908 (1986)
6) T. Rosen et al.: J. Am. Chem. Soc. 107, 3731 (1985)
7) G. E. Keck et al.: J. Org. Chem. 51, 2487 (1986)
8) A. P. Kozikowsky et al.: J. Org. Chem. 52, 3541 (1987)
9) S. J. Danishefsky et al.: J. Am. Chem. Soc. 111, 2599 (1989)

Microorganisms capable of producing MB-530B include, for example, *Monascus ruber* van Tieghem SANK 15679 belonging to the genus Monascus. This strain has been deposited under the conditions of the Budapest Treaty at the Research Institute of Life Science Technology, Agency of Industrial Science & Technology, Ministry of Internal Trade and Industry, Tokyo, Japan (formerly known as the Research Institute of Microbiological Technology, Agency of Industrial Science & Technology, Ministry of Internal Trade and Industry) under the Deposition Number FERM BP-4246: Date of Deposition, 24, Mar., 1993. *Monascus ruber* van Tieghem SANK 15679 has been internationally deposited for the second time, since this strain has previously been reported in, for example, British Patent No. 2046737 as *Monascus ruber* 1005, and internationally deposited as FERMBP-682. Its mycological properties and its culture method are the same as described in this British Patent.

M-4 and M-4' can be obtained by enzymatic stereospecific hydroxylation at position 6 of ML-236B. An example of a microorganism capable of converting ML-236B into M-4 by hydroxylation is *Amycolata autotrophica* SANK 62981 belonging to the genus Amycolata. This strain has been internationally deposited under the conditions of the Budapest Treaty at the Research Institute of Microbiological Technology, Agency of Industrial Science & Technology, Ministry of Internal Trade and Industry, under the Deposition Number, FERM BP-4105: Date of Deposition, 8, Dec., 1992.

An example of a microorganism capable of converting ML-236B into M-4' by hydroxylation is *Syncephalastrum nigricans* Vuillemin SANK 42372 belonging to the genus Syncephalastrum. This strain has been internationally deposited under the conditions of the Budapest Treaty at the Research Institute of Microbiological Technology, Agency of Industrial Science a Technology, Ministry of Internal Trade and Industry, under the Deposition Number, FERM BP-4106: Date of Deposition, 8, Dec., 1992.

The mycological properties of these strains are as follows. Mycological properties of *Amycolata autotrophica* SANK 62981

According to the methods of Shirling and Gottlieb [International Journal of Systematic Bacteriology 16, 313–340 (1968)] and of S. A. Waksman [The Actinomycetes], the strain was observed throughout 14 days.

(1) Morphological characteristics

The shape of the top of aerial hyphae: Rectus-flexibilis

The mode of hyphal branching: Simple branching

Hyphal division: Observable

Surface structure of arthrospores: Smooth

Other organs: No (2) Properties on various kinds of media for classification

The strain grows well on any of the media tested.

Strain SANK 62981 grows showing a brownish white to pale yellowish orange color. With the progress of cultivation, brownish violet spots are observed.

On other media than yeast extract—malt extract agar madium, insertion of light brownish grey aerial hyphae is observed.

No formation of soluble pigment is observed.

TABLE 2

Properties after culture for 14 days at 28° C. on various kinds of media

| Medium | Item | SANK 62981 |
| --- | --- | --- |
| Yeast extract - malt extract agar | G | Very good, brownish white (2-9-8) to grayish red brown (ISP 2) (4-3-5) |
|  | AM | Trace, white |
|  | R | Brownish white (2-9-8) to grayish red brown (4-3-5) |
|  | SP | No |
| Oatmeal agar (ISP 3) | G | Very good, dark reddish brown (4-3-4) |
|  | AM | Ordinary, pale pink (2-8-4) |
|  | R | Brownish violet (3-3-2) |
|  | SP | No |
| Starch-inorganic salt agar (ISP 4) | G | Very good, brownish violet, (3-3-2) |
|  | AM | Good, Light brownish gray (2-8-2) |
|  | R | Dark reddish brown (4-3-4) |
|  | SP | No |
| Glycerine - asparagine agar agar (ISP 5) (ISP 5) | G | Very good, pale brown (2-9-9) to brownish violet (3-3-2) |
|  | AM | Abundant, white |
|  | R | Pale yellowish orange (2-9-9) to grayish red brown (4-3-6) |
|  | SP | No |
| Tyrosine agar (ISP 7) | G | Good, grayish brown (4-6-6) |
|  | AM | Trace, white |
|  | R | Pale yellowish orange (2-9-9) to brownish violet (3-3-2) |
|  | SP | No |
| Sucrose nitrate agar | G | Not so good, pale yellowish orange (2-9-9) |
|  | AM | Ordinary, white |
|  | R | Pale yellowish orange (2-9-9) |
|  | SP | No |
| Glucose - asparagine agar | G | very good, pale yellowish orange (2-9-9) to brownish violet (3-3-2) |
|  | AM | Ordinary, white |
|  | R | Pale yellowish orange (2-9-9) to grayish red brown (4-3-6) |
|  | SP | No |
| Nutrient agar | G | Good, pale yellowish orange (2-9-9) |
|  | AM | Trace, white |
|  | R | Pale yellowish orange (2-9-9) |
|  | SP | No |
| Water agar | G | Not so good, pale yellowish orange (2-9-9) |
|  | AM | Ordinary, white |
|  | R | Pale yellowish orange (2-9-9) |
|  | SP | No |
| Potato extract - carrot extract agar | G | Not so good, pale yellowish orange (2-9-9) |
|  | AM | Ordinary, white |
|  | R | Pale yellowish orange (2-9-9) |
|  | SP | No |

In the table, G, AM, R and SP mean growth, aerial mycelium, reverse and soluble pigment respectively.
The tones of color are indicated in the above Table according to the Color Tip Numbers described in [Standard Color Table] published by Nihon Shikisai Kenkyujo.

(3) Physiological properties

Reduction of nitrate: Positive

Hydrolysis of starch: Negative

Formation of melanoid pigment: Negative (Medium 1): Tryptone-yeast extract broth (ISP 1)

(Medium 2): Peptone-yeast extract-iron agar (ISP 6)

(Medium 3): Tyrosine agar (ISP 7)

(4) Assimilability of various kinds of carbon sources

By using Pridham-Gottlieb agar medium (ISP 9), assimilation of carbon sources was examined and judged after culture for 14 days at 28° C.

In the following table:

| + means assimilation,<br>± means a little assimilation and<br>− means no assimilation. | |
|---|---|
| D-Glucose | + |
| L-Arabinose | + |
| D-Xylose | + |
| D-Fructose | + |
| L-Rhamnose | ± |
| Inositol | + |
| Sucrose | − |
| Raffinose | − |
| D-Mannitol | + |
| Control | − |

[(5) Intracellular components

According to the methods of B. Becker et al. Applied Microbiology 12, 236 (1965)], and M. P. Lechevalier et al. [The Actinomycetales by H. Prauser, p. 311 (1970)], the acid hydrolysates of the cells of these strains were analyzed by paper chromatography. In the cell walls, meso-2,6-diaminopimelic acid was found, and arabinose and galactose were noted as sugar components of the bacterial cells, from which the bacterial components were confirmed to be type IV-A.

No mycolic acid was found.

From these results, strain SANK 62981 was determined to belong to the species *Amycolata autotrophica.*

However, SANK 62981 shows a tone of amethystine color when grown, and may thus be a sub-spicies of *Amycolata autotrophica.*

This strain has been deposited under the conditions of the Budapest Treaty at the Research Institute of Microbiological Technology, Agency of Industrial Science & Technology, Ministry of Internal Trade and Industry, Japan, under the Deposition Number FERMBP-4105.

This strain was identified according to the standard of the International Streptomyces Project; [Bergey's Manual of Determinative Bacteriology, 8th Ed.]; [The Actinomycetes, Vol. 2] by S. A. Waksman; and recent reports about Actinomycetes. The genus Amycolata was hitherto classified as par of the genus Nocardia. However, because of differences in the components of bacterial cells, Amycolata is now thought to be an independent genus from Nocardia, and each forms a new genus [International Journal of Systematic Bacteriology 36, 29 (1986)].

Mycological properties of *Syncephalastrum nigricans* Vuillemin SANK 42372

Vegetative hyphae develop well and grow rapidly.

Sporangiophores stand vertically from the hyphae, are pale brown in color with rhizoid and irregular branches, and form septa.

Lateral branches sometimes curve sharply.

At the tops of the main axis and lateral branches, vesicles are formed. Vesicles are sub-spherical or oval, sometimes elliptical in shape, and those formed at the top of the main axis are 28 μm to 50 μm in diameter, and those formed at the top of the lateral branches are 15 μm to 25 μm in diameter.

Many merosporangia are formed on the whole surface. Sporangiophores are single rod or finger-like in shape, and frequently from 5 to 10 spores are formed in a line.

Spores are almost colorless with smooth surfaces, unicellular and sub-spherical to oval in shape, from 3.5 μm to 6.5 μm in diameter.

No zygospores are observable.

Comparing these properties with those of known strains, the properties of this strain accorded well with those of *Syncephalastrum nigricans* Vuillemin described in "An Illustrated Book of Fungi" Edited by Keisuke Tsubaki & Shun-ichi Udagawa, Kodansha; p.303–304 (1978).

This strain has been deposited under the conditions of the Budapest Treaty at the Research Institute of Microbiological Technology, Agency of Industrial Science & Technology, Ministry of Internal Trade and Industry under the Deposition Number FERMBP-4106.

These microorganisms may be used to introduce a hydroxy group at the 6-position of, for example, ML-236B by cultivating the converting microorganism on a medium containing nutrients assimilable by the microorganism and under suitable culture conditions for growth of the converting microorganism, followed by any of the following methods:

Method 1

At an intermediate stage of culture of the converting microorganism, the starting compound, for example, ML-236B, is added to the medium and contacted with the microorganism during further culture.

Method 2

The converting microorganism is cultured and collected. Then, the resulting cells are contacted with the starting compound.

Method 3

A cell-free extract containing the active enzyme is prepared from cells of the converting microorganism, and a solution of the extract, without cells, is contacted with the starting compound.

Examples of media containing nutrients assimilable by the converting microorganism, the general culture method, the pH of media suitable for the growth of the converting microorganism, the temperature of the medium suitable for the growth of the converting microorganism, and isolation and purification conditions are all as described above in relation to the production of ML-236B.

It will be appreciated that the strains mentioned above, or any other strain capable of similar activity, may be subcultured or biotechnologically altered or modified to produce an organism with different characteristics. The only requirement is that the resulting organism be capable of producing the required compound. Alterations may occur naturally or artificially, by induction.

Such alterations and modifications may take any desired form, or may be consequent on such considerations as culture conditions, for example. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in species of which the above are strains. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring plasmid and inserting a desired gene or genes from another source. Natural plasmids may also be modified in any other manner that may be considered desirable.

Any such modified strain may be employed in the process of the present invention, provided only that the strain is capable of the required activity, a matter which can readily be ascertained by simple and routine experimentation.

BIOLOGICAL ACTIVITY

The compounds of the present invention have a marked ability to reduce the levels of serum cholesterol. Specifically, the compounds inhibit the biosynthesis of chlolesterol in an enzyme system or a culture cell system separated from an experimental animal by inhibiting 3-hydroxy-3-methylglutaryl-CoA reductase (HMG-CoA), the rate limiting enzyme of sterol biosynthesis, by competing with the HMG-CoA. This suggests that the compounds will exhibit a powerful serum cholesterol reducing effect when employed in the treatment of humans and other animals. The determination of the inhibitory activity of the compounds was made using the method of Kuroda et al ["Biochimica et Biophysica Acta" Vol. 486, pp. 70–81 (1977)] which is a modification of the known method of D. J. Shapiro et al ["Analytical Biochemistry" Vol. 31, pp. 383–390 (1969)] with some improvements.

The results are shown in Table 3.

TABLE 3

| Compound | HMG-CoA reductase $IC_{50}$ (nM) |
|---|---|
| Na salt of Compound of Preparation 1[1*] | 18.5 |
| Compound of Example 1c | 16.3 |
| Na salt of Compound of Preparation 9[2*] | 22.8 |
| Compound of Example 9c | 20.2 |
| Na salt of Compound of Preparation 11[3*] | 17.3 |
| Compound of Example 11c | 16.3 |
| Sodium 3,5-dihydroxy-7-[2,6-dimethyl-8-(2-methylbutyryloxy)-1,2,6,7,8,8a-hexahydro-1-naphthyl]heptanoate[4*] | 27.0 |
| 3-Hydroxy-5-oxo-7-[2,6-dimethyl-8-(2-methylbutyryloxy)-1,2,6,7,8,8a-hexahydro-1-naphthyl]heptanoate[5*] | 604 |
| Sodium 3,5-dihydroxy-7-[2,6-dimethyl-8-(2,2-dimethylbutyryloxy)-1,2,6,7,8,8a-hexahydro-1-naphthyl]heptanoate[6*] | 43.6 |
| 3-Hydroxy-5-oxo-7-[2,6-dimethyl-8-(2,2-dimethylbutyryloxy)-1,2,6,7,8,8a-hexahydro-1-naphthyl]heptanoate[7*] | 487 |

Note:
[1*]This compound was obtained by a similar treatment of the Compound of Preparation 1 to that described in Example 1b followed by a similar treatment to that described in Example 1c. This compound is the same as described in Example 1b of Japanese Patent Kokai Application No. Hei-2-255.
[2*] This compound was obtained a similar treatment of the Compound of Preparation 9 to that described in Example 1b followed by a similar treatment to that described in Example 1c.
[3*] This compound was obtained by a similar treatment of the Compound of Preparation 11 to that described in Example 1b followed by a similar treatment to that described in Example 1c.
[4*] This compound is the sodium salt of the compound described as Compound No. 2 in Journal of Medicinal Chemistry 29, 849–852 (1986), and is also the sodium salt of one of the compounds included in Table IV of Japanese Patent Publication No. Sho-64-1476, where R is a 1-methylpropyl group.
[5*] This compound is the 5-oxo derivative of Compound 4* mentioned above. In Table I of Japanese Patent Kokai Application No. Sho-60-123445, this compound is included, where $R^7OC$— is 2-methylbutyryl, $R^8$ is —$CH_3$., X is —O—, and each of a and b is a double bond.
[6*] This compound is the sodium salt of the compound described as Compound No. 16 in Journal of Medicinal Chemistry 29, 849–852 (1986), and also the sodium salt of one of the compounds included in Table IV of Japanese Patent Publication No. Sho-64-1476, where R is 1,1-dimethylpropyl. This compound is the sodium salt of sinvastatin (generic name, taken from "New Drugs in Japan").
[7*] This compound is the 5-oxo derivative of Compound 6* mentioned above. In Table I of Japanese Patent Kokai Application No. Sho-60-123445, this compound is included, where $R^7OC$— is 2,2-dimethylbutyryl, $R^8$ is —$CH_3$, X is —O—, and each of a and b is a double bond.

From Table 3, it can be seen clearly that the compounds of the present invention all have better activities than their directly comparable hydroxy equivalents, and that, in Compounds 6* and 7* which are obtained by oxidation of the hydroxy group at the 5-position of Compounds 4* and 5*, respectively, the activity is very much lower than in the original hydroxy compounds. On the other hand, in the 5-oxo compounds in the octahydronaphthalene-substituted oxime derivatives of the present invention, the activity is higher than in the original hydroxyl compounds.

The compounds of the present invention act to inhibit the synthesis of cholesterol, and thereby reduce the level of lipids in the blood. They can, therefore, be utilized in therapy, for example, as a hypolipemic agent or as an arteriosclerosis prophylactic.

These compounds can be administered orally or parenterally, for example, in the form of capsules, tablets, injections, or other conventional dosage forms. The dosage of such compound will depend on the age, condition and body weight, of the patient, as well as on the nature and severity of the symptoms, but we would normally suggest a dosage for an adult human patient of from 0.5 mg to 500 mg per day, which can be administered in a single dose or in divided doses, preferably in divided doses, e.g. in 2 to 4 doses daily. However, it can be used in an amount above this range, as necessary.

The compounds of the invention can be, and preferably are, administered in conventional pharmaceutical formulations in admixture with one or more conventional excipients, carriers or diluents, as are well known for use with compounds having this type of activity.

The invention is further illustrated by the following Examples, which illustrate the preparation of compounds of the present invention. The subsequent Preparations illustrate the preparation of certain of the starting materials used in the preparation of the compounds of the invention.

EXAMPLE 1a

Allyl 7-[5-benzyloxyimino-2-methyl-8-(2-methylbutyryloxy)-3-oxo-1,2,3,5,6,7,8,8a-octahydro-1-naphthyl]-3hydroxy-5-oxoheptanoate (allyl ester of Compound No. 1)

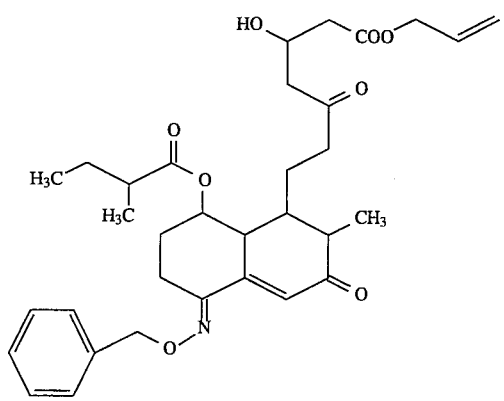

182 μl (1.3 mmole) of trifluoroacetic anhydride were dissolved in 2 ml of anhydrous toluene, and the resulting solution was cooled to −78° C. 1 ml of anhydrous toluene in which 121 μl (1.71 mmole) of dimethyl sulfoxide had been dissolved was then added dropwise under an atmosphere of nitrogen to the cooled solution over a period of 5 minutes.

After the addition was complete, the mixed solution was stirred for 3 minutes, and then 3 ml of anhydrous toluene, in which 500 mg (0.86 mmole) of allyl 7-[5-benzyloxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 1) had been dissolved, were added dropwise over a period of 15 minutes. The solution was stirred for 15 minutes at −78° C., and then 0.6 ml (4.3 mmole) of triethylamine was added dropwise over a period of 5 minutes. The resulting reaction mixture was stirred for 20 minutes at −78° C. and for a further 40 minutes at 0° C. At the end of this time, 30 ml of a 10% w/v aqueous solution of citric acid was added to the reaction mixture, and the mixture was extracted at room temperature with ethyl acetate. The ethyl acetate extract was washed with a saturated aqueous solution of sodium hydrogencarbonate and then with a saturated aqueous solution of sodium chloride, after which it was dried over anhydrous magnesium sulfate, filtered and condensed by evaporation under reduced pressure. The resulting oily residue was purified by flash column chromatography through silica gel, using a 2:1 by volume mixture of ethyl acetate and hexane as the eluent, to obtain 183 mg (yield 48%) of the title compound. At that time, 166 mg of unreacted starting material was also recovered.

Nuclear Magnetic Resonance Spectrum (CDCl$_3$, 270 MHz) δ ppm: 0.86 (3H, triplet, J=7.3 Hz); 1.01 (3H, doublet, J=7.3 Hz); 1.10 (3H, doublet, J=7.3 Hz); 1.34–1.81 (4H, multiplet); 1.91–2.10 (1H, multiplet); 2.15–2.71 (10H, multiplet); 2.54 (2H, doublet, J=6.4 Hz); 3.11–3.24 (1H, multiplet); 3.28–3.37 (1H, multiplet, exchangeable with D$_2$O); 4.40–4.52 (1H, multiplet); 4.61 (2H, doublet, J=5.9 Hz); 5.13–5.38 (2H, multiplet); 5.20 (2H, doublet, J=2.9 Hz); 5.43–5.50 (1H, multiplet); 5.82–6.00 (1H, multiplet); 6.51 (1H, doublet, J=2.5 Hz); 7.28–7.41 (5H, multiplet).

Infrared Absorption Spectrum (CHCl$_3$) $v_{max}$ cm$^{-1}$: 3500, 2950, 1720, 1660, 1450, 1370, 1180, 1150, 1050, 980.

Mass spectrum m/z=581 (M$^+$).

EXAMPLE 1b

7-[5-Benzyloxyimino-2-methyl-8-(2-methylbutyryloxy)-3-oxo-1,2,3,5,6,7,8,8a-octahydro-1-naphthyl]-3-hydroxy-5-oxoheptanoic acid (Compound No. 1)

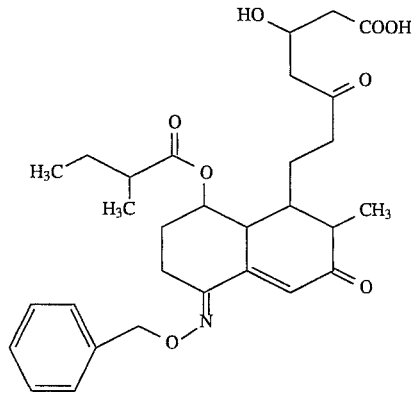

239 mg (0.4 mmole) of allyl 7-[5-benzyloxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 1a) were dissolved in 3.3 ml of anhydrous tetrahydrofuran, and 20.7 mg (0.02 mmole) of tetrakis(triphenylphosphine)palladium (0), 21.5 mg (0.08 mmole) of triphenylphosphine and 31 μl (0.82 mmole) of formic acid were added to the solution, and the resulting mixture was stirred for 18 hours under an atmosphere of nitrogen. At the end of this time, the reaction mixture was condensed by evaporation under reduced pressure, and the residue was dissolved in a 50% v/v aqueous solution of acetonitrile. The solution was filtered through a SEP-PAK C-18 Cartridge (Trade name for a product of Waters Co.) and extracted with ethyl acetate. The resulting ethyl acetate extract was dried over anhydrous magnesium sulfate, filtered and condensed by evaporation under reduced pressure. The resulting oily residue was purified through a reverse phase Lobar Column (RP-18, Size B, Merck), using as the eluent a buffer solution consisting of a 1:1 by volume mixture of acetonitrile and aqueous phosphoric acid (pH 3.0) containing 0.001M of triethylamine, to obtain 106 mg (yield 48%) of the title compound as an oily substance.

Nuclear Magnetic Resonance Spectrum (CDCl$_3$, 270 MHz) δ ppm: 0.87 (3H, triplet, J=7.3 Hz); 1.00 (3H, doublet, J=7.3 Hz); 1.10 (3H, doublet, J=7.3 Hz); 1.35–1.82 (4H, multiplet); 1.92–2.11 (1H, multiplet); 2.13–2.70 (8H, multiplet); 2.56 (2H, doublet, J=6.4 Hz); 2.65. (2H, doublet, J=6.1 Hz); 2.75–3.70 (2H, multiplet, 2H exchangeable with D$_2$O); 3.18 (1H, doublet of doublets, J=6.3 & 16.6 Hz); 4.41–4.52 (1H, multiplet); 5.21 (2H, doublet, J=2.9 Hz); 5.43–5.51 (1H, multiplet); 6.52 (1H, doublet, J=2.5 Hz); 7.28–7.41 (5H, multiplet).

Infrared Absorption Spectrum (CHCl$_3$) $v_{max}$ cm$^{-1}$: 3500, 2950, 1720, 1660, 1450, 1410, 1370, 1180, 1150, 1010, 880.

Mass spectrum m/z=479 (M$^+$).

EXAMPLE 1c

Sodium 7-[5-benzyloxyimino-2-methyl-8-(2-methylbutyryloxy)-3-oxo-1,2,3,5,6,7,8,8a-octahydro-1-naphthyl]-3-hydroxy-5-oxoheptanoate (sodium salt of Compound No. 1)

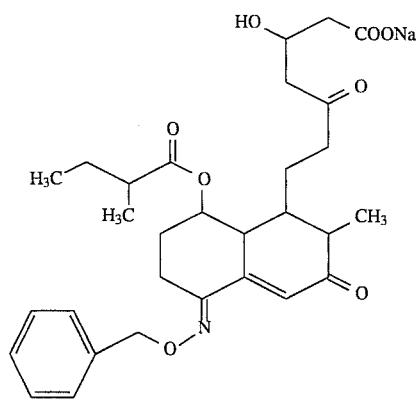

103 mg of 7-[5-benzyloxyimino-2-methyl-8-(2-methylbutyryloxy)-3-oxo-1,2,3,5,6,7,8,8a-octahydro-1-naphthyl]-3-hydroxy-5-oxoheptanoic acid (prepared as described in Example 1b) were dissolved in 2 ml of a 1:1 by volume mixture of dioxane and water. 1.8 ml of a 0.1N aqueous solution of sodium hydroxide were then added dropwise to the solution over a period of 5 minutes at 0° C., after which the solution was stirred for 1 hour at room temperature. At the end of this time, the solution was freeze-dried, to obtain 107 mg of the title compound as a colorless moisture sensitive powder.

EXAMPLE 2a

Allyl 7-[5-(furan-2-yl)methoxyimino-2-methyl-8-(2-methylbutyryloxy)3-oxo-1,2,3,5,6,7,8,8a-octahydro-1-naphthyl]-3-hydroxy-5-oxoheptanoate (allyl ester of Compound No. 39)

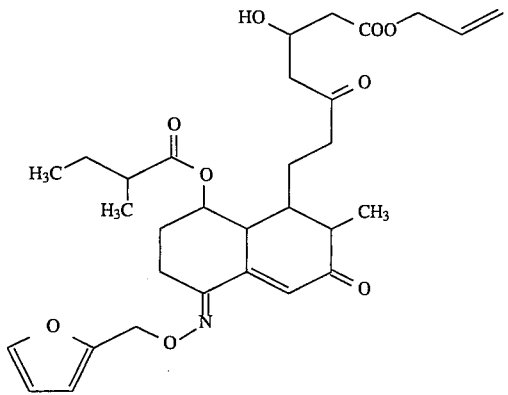

A procedure similar to that described in Example 1a was repeated, but using 1.33 g of allyl 7-[5-(furan-2-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 2), to obtain 599 mg of the title compound.

Nuclear Magnetic Resonance Spectrum (CDCl$_3$, 270 MHz) δ ppm: 0.86 (3H, triplet, J=7.3 Hz); 1.01 (3H, doublet, J=7.3 Hz); 1.09 (3H, doublet, J=7.3 Hz); 1.22–1.86 (4H, multiplet); 1.90–2.72 (11H, multiplet); 2.55 (2H, doublet, J=6.4 Hz); 3.07–3.20 (1H, multiplet); 3.28–3.39 (1H, multiplet, exchangeable with D$_2$O); 4.40–4.52 (1H, multiplet); 4.61 (2H, doublet, J=5.9 Hz); 4.98–5.38 (2H, multiplet); 5.12 (2H, doublet, J=2.0 Hz); 5.43–5.50 (1H, multiplet); 5.85–6.00 (1H, multiplet); 6.32–6.43 (2H, multiplet); 6.51 (1H, doublet, J=2.4 Hz); 7.42–7.44 (1H, multiplet).

Infrared Absorption Spectrum (CHCl$_3$) $v_{max}$ cm$^{-1}$: 3500, 2950, 1730, 1660, 1600, 1500, 1460, 1410, 1380, 1350, 1180, 1150, 1010, 980, 920, 880.

Mass spectrum m/z=571 (M$^+$).

EXAMPLE 2b

7-[5-(Furan-2-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid

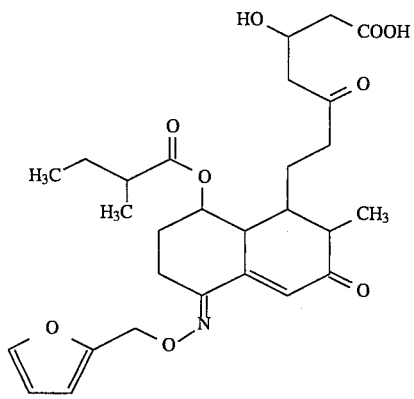

A procedure similar to that described in Example 1b was repeated, except that 490 mg of allyl 7-[5-(furan-2-yl)methoxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 2a) were used, to obtain 329 mg of the title compound.

Nuclear Magnetic Resonance Spectrum (CDCl$_3$, 270 MHz) δ ppm: 0.86 (3H, triplet, J=7.3 Hz); 1.01 (3H, doublet, J=7.3 Hz); 1.09 (3H, doublet, J=7.3 Hz); 1.30–1.82 (4H, multiplet); 1.90–2.74 (11H, multiplet); 2.56 (2H, doublet, J=6.3 Hz); 3.08–3.23 (1H, multiplet); 3.24–4.82 (2H, multiplet, 2H exchangeable with D$_2$O); 4.41–4.53 (1H, multiplet); 4.98–5.20 (2H, multiplet); 5.44–5.51 (1H, multiplet); 6.32–6.45 (2H, multiplet); 6.52 (1H, doublet, J=2.4 Hz); 7.43–7.44 (1H, multiplet).

Infrared Absorption Spectrum (CHCl$_3$) $\nu_{max}$ cm$^{-}$: 3500, 2950, 1720, 1660, 1500, 1460, 1410, 1380, 1350, 1290, 1180, 1150, 1080, 1000, 980, 920, 880.

Mass spectrum m/z=469 (M$^+$ −62).

EXAMPLE 3a

Allyl 7-[5-(1,3-dioxan-5-yl)methoxyimino-2-methyl-8-(2-methylbutyryloxy)-3-oxo-1,2,3,5,6,7,8,8a-octahydro-1-naphthyl]-3-hydroxy-5-oxoheptanoate (allyl ester of Compound No. 54)

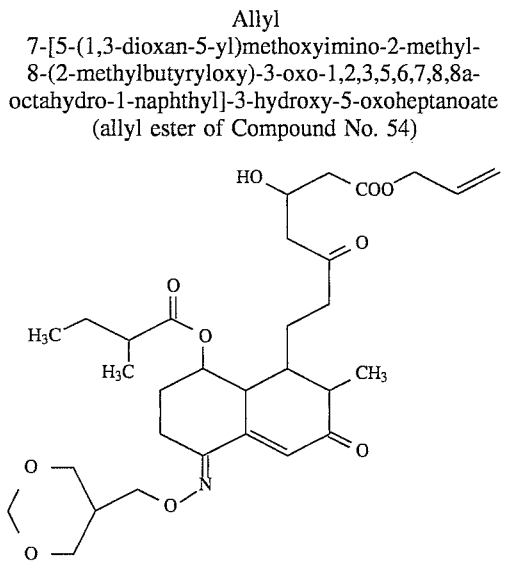

A procedure similar to that described in Example 1a was repeated, except that 10.6 g of allyl 7-[5-(1,3-dioxan-5-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 3) were used, to obtain 4.3 g of the title compound.

Nuclear Magnetic Resonance Spectrum (CDCl$_3$, 270 MHz) δ ppm: 0.88 (3H, triplet, J=7.3 Hz); 1.00 (3H, doublet, J=7.3 Hz); 1.11 (3H, doublet, J=7.3 Hz); 1.31–1.82 (5H, multiplet, 1H exchangeable with D$_2$O); 1.91–2.73 (12H, multiplet); 2.54 (2H, doublet, J=5.9 Hz); 3.04–3.19 (1H, multiplet); 3.75 (2H, doublet of doublets, J=5.9 & 11.7 Hz); 3.99 (1H, doublet, J=3.9 Hz); 4.03 (1H, doublet, J=3.4 Hz); 4.25 (2H, doublet, J=6.8 Hz); 4.41–4.54 (1H, multiplet); 4.62 (2H, doublet, J=5.9 Hz); 4.81 (1H, doublet, J=5.9 Hz); 4.89 (1H, doublet, J=5.9 Hz); 5.23–5.39 (2H, multiplet); 5.45–5.52 (1H, multiplet); 5.83–6.00 (1H, multiplet); 6.49 (1H, doublet, J=2.4 Hz).

Infrared Absorption Spectrum (CHCl$_3$) $\nu_{max}$ cm$^{-1}$: 3500, 2960, 2930, 2850, 1730, 1660, 1460, 1370, 1290, 1260, 1180, 1150, 1030, 980, 970, 930, 880.

Mass spectrum m/z=591 (M$^+$).

EXAMPLE 3b

7-[5-(1,3-Dioxan-5-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid (Compound No. 54).

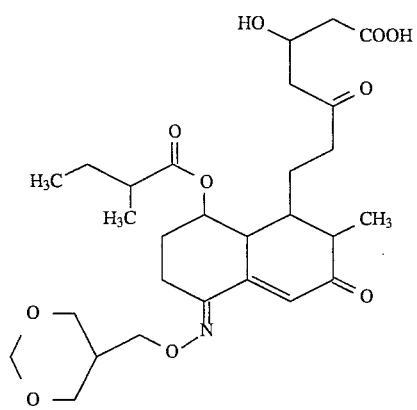

A procedure similar to that described in Example 1b was repeated, except that 4.9 g of allyl 7-[5-(1,3-dioxan-5-yl)methoxyimino-2-methyl-8-(2-methylbutyryloxy)-3-oxo-1,2,3,5,6,7,8,8a-octahydro-1-naphthyl]-3-hydroxy-5-oxoheptanoate [prepared as described in Example 3a] were used, to obtain 3.1 g of the title compound.

Nuclear Magnetic Resonance Spectrum (CDCl$_3$, 270 MHz) δ ppm: 0.88 (3H, triplet, J=7.3 Hz); 1.01 (3H, doublet, J=7.3 Hz); 1.11 (3H, doublet, J=7.3 Hz); 1.32–1.83 (4H, multiplet); 1.94–2.88 (14H, multiplet, 2H exchangeable with D$_2$O); 2.55 (2H, doublet, J=6.2 Hz); 3.04–3.19 (1H, multiplet); 3.75 (2H, doublet of doublets, J=6.4 & 11.7 Hz); 3.99 (1H, doublet, J=3.4 Hz); 4.04 (1H, doublet, J=3.9 Hz); 4.25 (2H, doublet, J=6.8 Hz); 4.41–4.54 (1H, multiplet); 4.85 (2H, doublet of doublets, J=5.9 & 20.0 Hz); 5.46–5.52 (1H, multiplet); 6.49 (1H, doublet, J=2.4 Hz).

Infrared Absorption Spectrum (CHCl$_3$) $v_{max}$ cm$^{-1}$: 3500, 2950, 2920, 2850, 1720, 1660, 1550, 1460, 1410, 1370, 1290, 1260, 1180, 1150, 1090, 1030, 970, 930, 880.

Mass spectrum m/z=551 (M$^+$).

EXAMPLE 4a

Allyl 7-[5-(2-ethoxybenzyloxyimino)-2-methyl-8-(2-methylbutyryloxy)-3-oxo-1,2,3,5,6,7,8,8a-octahydro-1-naphthyl]-3-hydroxy-5-oxoheptanoate (allyl ester of CompoUnd No. 126)

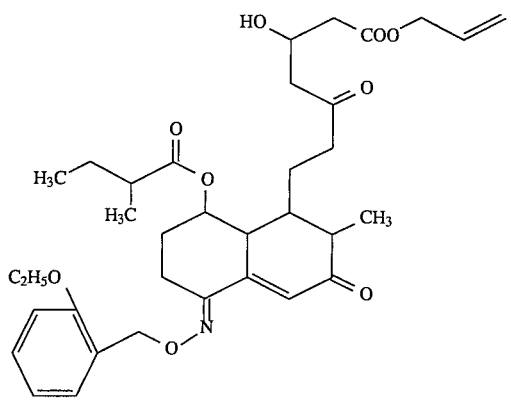

A procedure similar to that described in Example 1a was repeated, except that 670 mg of allyl 7-[5-(2-ethoxybenzyloxyimino)-2-methyl-8-(2-methylbutyryloxy)-3-oxo-1,2,3,5,6,7,8,8a-octahydro-1-naphthyl]-3,5-dihydroxyheptanoate (prepared as described in Preparation 4) were employed, to obtain 205 mg of the title compound.

Nuclear Magnetic Resonance Spectrum (CDCl$_3$, 270 MHz) δ ppm: 0.86 (3H, triplet, J=7.3 Hz); 1.01 (3H, doublet, J=7.3 Hz); 1.11 (3H, doublet, J=6.8 Hz); 1.40 (3H, triplet, J=7.3 Hz); 1.45–1.78 (6H, multiplet, 1H exchangeable with D$_2$O); 1.96–2.07 (2H, multiplet); 2.17–2.56 (8H, multiplet); 2.62 (2H, doublet, J=4.3 Hz); 3.16–3.24 (1H, multiplet); 4.02–4.10 (2H, multiplet); 4.44–4.50 (1H, multiplet); 4.62 (2H, doublet, J=5.8 Hz); 5.23–5.36 (4H, multiplet); 5.47 (1H, singlet); 5.84–5.96 (1H, multiplet); 6.54 (1H, doublet, J=2.4 Hz); 6.85–6.96 (2H, multiplet); 7.23–7.33 (2H, multiplet).

Infrared Absorption Spectrum (CHCl$_3$) $v_{max}$ cm$^{-1}$: 3500, 2925, 1725, 1660,I 1490, 1450, 1180, 1150, 1010, 1020, 990, 900, 840.

Mass spectrum m/z=625 (M$^+$ +1).

EXAMPLE 4b

7-[5-(2-Ethoxybenzyloxyimino)-2-methyl-8-(2-methylbutyryloxy)-3-oxo-1,2,3,5,6,7,8,8a-octahydro-1-naphthyl]-3-hydroxy-5-oxoheptanoic acid (Compound No. 126)

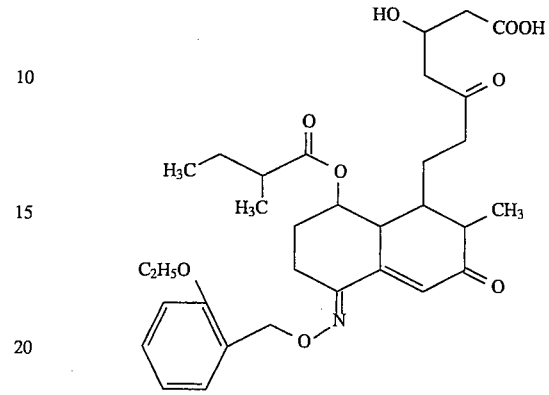

A procedure similar to that described in Example 1b was repeated, except that 191 mg of allyl 7-[5-(2-ethoxybenzyloxyimino)-2-methyl-8-(2-methylbutyryloxy)-3-oxo-1,2,3,5,6,7,8,8a-octahydro-1-naphthyl]-3-hydroxy-5-oxoheptanoate (prepared as described in Example 4a) were employed, to obtain 164 mg of the title compound.

Nuclear Magnetic Resonance Spectrum (CDCl$_3$, 270 MHz) δ ppm: 0.87 (3H, triplet, J=7.3 Hz); 1.01 (3H, doublet, J=7.3 Hz); 1.12 (3H, doublet, J=7.3 Hz); 1.41 (3H, triplet, J=6.8 Hz); 1.45–2.67 (15H, multiplet, 2H exchangeable with D$_2$O); 2.57 (2H, doublet, J=13.1 Hz); 2.64 (2H, doublet, J=4.8 Hz); 3.16–3.24 (1H, multiplet); 4.06–4.16 (2H, multiplet); 4.43–4.52 (1H, multiplet); 5.29 (2H, singlet); 5.48 (1H, singlet); 6.54 (1H, doublet, J=2.4 Hz); 6.86–6.96 (2H, multiplet); 7.23–7.33 (2H, multiplet).

Infrared Absorption Spectrum (CHCl$_3$) $v_{max}$ cm$^{-1}$: 3500, 2975, 1725, 1660, 1490, 1450, 1375, 1240, 1180, 1150, 1010.

Mass spectrum m/z=556 (M$^+$ −29).

EXAMPLE 5a

Allyl 7-[5-(2-chlorobenzyloxyimino)-2-methyl-8-(2-methylbutyryloxy)-3-oxo-1,2,3,5,6,7,8,8a-octahydro-1-naphthyl]-3-hydroxy-5-oxoheptanoate (allyl ester of Compound No. 135)

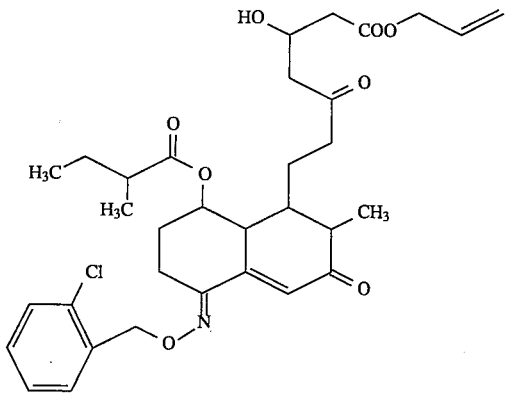

A procedure similar to that described in Example 1a was repeated, except that 960 mg of allyl 7-[5-(2-chlorobenzyloxyimino)-2-methyl-8-(2-methylbutyryloxy)-3-oxo-1,2,3,5,6,7,8,8a-octahydro-1-naphthyl]-3,5-dihydroxyheptanoate (prepared as described in Preparation 5) were employed, to obtain 334 mg of the title compound.

Nuclear Magnetic Resonance Spectrum (CDCl$_3$, 270 MHz) δ ppm: 0.87 (3H, triplet, J=7.5 Hz); 1.01 (3H, doublet, J=7.3 Hz); 1.09 (3H, doublet, J=7.3 Hz); 1.37–1.79 (6H, multiplet, 1H exchangeable with D$_2$O); 1.95–2.07 (2H, multiplet); 2.19–2.71 (8H, multiplet); 2.62 (2H, doublet, J=4.3 Hz); 3.16–3.24 (1H, multiplet); 4.44–4.53 (1H, multiplet); 4.60 (2H, doublet, J=5.8 Hz); 5.23–5.36 (4H, multiplet); 5.47 (1H, singlet); 5.84–5.96 (1H, multiplet); 6.51 (1H, doublet, J=2.4 Hz); 7.24–7.41 (4H, multiplet).

Infrared Absorption Spectrum (CHCl$_3$) ν$_{max}$ cm$^{-1}$: 3000, 2950, 1725, 1660, 1440, 1410, 1180, 1150, 1090, 1010.

Mass spectrum m/z=616 (M$^+$).

EXAMPLE 5b

7-[5-(2-Chlorobenzyloxyimino)-2-methyl-8-(2-methylbutyryloxy)-3-oxo-1,2,3,5,6,7,8,8a-octahydro-1-naphthyl]-3-hydroxy-5-oxoheptanoic acid (Compound No. 135).

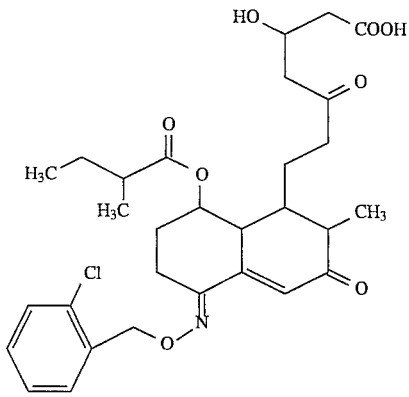

A procedure similar to that described in Example 1b was repeated, except that 289 mg of allyl 7-[5-(2-chlorobenzyloxyimino)-2-methyl-8-(2-methylbutyryloxy)-3-oxo-1,2,3,5,6,7,8,8a-octahydro-1-naphthyl]-3-hydroxy-5-oxoheptanoate (prepared as described in Example 5a) were employed, to obtain 209 mg of the title compound.

Nuclear Magnetic Resonance Spectrum (CDCl$_3$, 270 MHz) δ ppm: 0.87 (3H, triplet, J=7.5 Hz); 1.01 (3H, doublet, J=7.3 Hz); 1.09 (3H, doublet, J=6.8 Hz); 1.33–1.83 (4H, multiplet); 1.94–2.67 (11H, multiplet, 2H exchangeable with D$_2$O); 2.55 (2H, doublet, J=6.3 Hz); 2.64 (2H, doublet, J=4.3 Hz); 3.16–3.24 (1H, multiplet); 4.43–4.52 (1H, multiplet); 5.32 (2H, singlet); 5.48 (1H, singlet); 6.52 (1H, doublet, J=2.4 Hz); 7.23–7.48 (4H, multiplet).

Infrared Absorption Spectrum (CHCl$_3$) ν$_{max}$ cm$^{-1}$: 3500, 2925, 1725, 1660, 1440, 1410, 1375, 1260, 1180, 1150, 1010.

Mass spectrum m/z=577 (M$^+$ +1).

EXAMPLE 6a

Allyl 7-[5-(2,6-dichlorobenzyloxyimino)-2-methyl-8-(2-methylbutyryloxy)-3-oxo-1,2,3,5,6,7,8,8a-octahydro-1-naphthyl]-3-hydroxy-5-oxohetanoate (allyl ester of Compound No. 136)

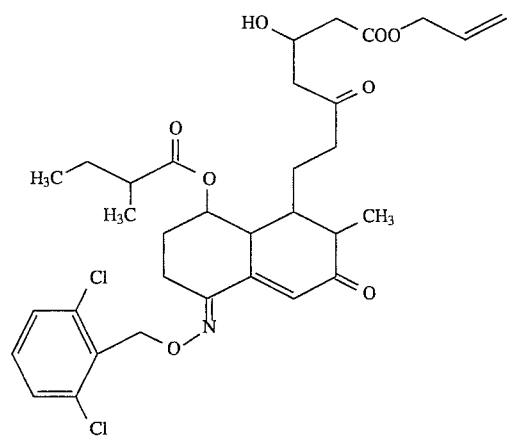

A procedure similar to that described in Example 1a was repeated, except that 1.32 g of allyl 7-[5-(2,6-dichlorobenzyloxyimino)-2-methyl-8-(2-methylbutyryloxy)-3-oxo-1,2,3,5,6,7,8,8a-octahydro-1-naphthyl]-3,5-dihydroxyheptanoate (prepared as described in Preparation 6) were employed, to obtain 481 mg of the title compound.

Nuclear Magnetic Resonance Spectrum (CDCl$_3$, 270 MHz) δ ppm: 0.86 (3H, triplet, J=7.3 Hz); 1.01 (3H, doublet, J=7.3 Hz); 1.09 (3H, doublet, J=7.3 Hz); 1.31–1.90 (5H, multiplet, 2H exchangeable with D$_2$O); 1.91–2.10 (2H, multiplet); 2.10–2.73 (9H, multiplet); 2.53 (2H, doublet, J=6.4 Hz); 3.03–3.19 (1H, multiplet); 4.39–4.52 (1H, multiplet); 4.60 (2H, doublet, J=5.9 Hz); 5.21–5.57 (3H, multiplet); 5.50 (2H, doublet, J=6.8 Hz); 5.83–6.00 (1H, multiplet); 6.56 (1H, doublet, J=2.4 Hz); 7.18–7.38 (3H, multiplet).

Infrared Absorption Spectrum (CHCl₃) $v_{max}$ cm⁻¹: 3500, 2950, 2930, 2900, 1720, 1660, 1580, 1560, 1440, 1370, 1290, 1180, 1150, 1090, 1020, 990.

Mass spectrum m/z=631 (M⁺ −19).

EXAMPLE 6b

2-[5-(2,6-Dichlorobenzyloxyimino)-2-methyl-8-(2-methylbutyryloxy)-3-oxo-1,2,3,5,6,7,8,8a-octahydro-1-naphthyl]-3-hydroxy-5-oxoheptanoic acid (Compound No. 136)

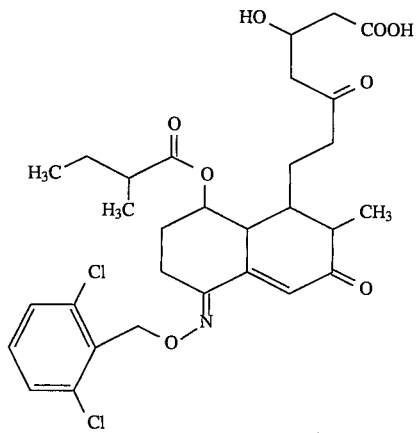

A procedure similar to that described in Example 1b was repeated, except that 465 mg of allyl 7-[5-(2,6-dichlorobenzyloxyimino)-2-methyl-8-(2-methylbutyryloxy)-3-oxo-1,2,3,5,6,7,8,8a-octahydro-1-napthyl]-3-hydroxy-5-oxoheptanoate (prepared as described in Example 6a) were employed, to obtain 339 mg of the title compound.

Nuclear Magnetic Resonance Spectrum (CDCl₃, 270 MHz) δ ppm: 0.86 (3H, triplet, J=7.3 Hz); 1.01 (3H, doublet, J=7.3 Hz); 1.09 (3H, doublet, J=7.3 Hz); 1.30–1.81 (4H, multiplet); 1.91–2.91 (11H, multiplet, 2H exchangeable with D₂O); 2.58 (2H, doublet, J=5.9 Hz); 2.66 (2H, doublet, J=5.4 Hz); 3.05–3.19 (1H, multiplet); 4.41–4.53 (1H, multiplet); 5.40–5.58 (3H, multiplet); 6.55 (1H, doublet, J=2.9 Hz); 7.18–7.39 (3H, multiplet).

Infrared Absorption Spectrum (CHCl₃) $v_{max}$ cm⁻¹: 3500, 2950, 1720, 1660, 1580, 1560, 1460, 1430, 1370, 1290, 1180, 1150, 1090, 1020, 990.

Mass spectrum m/z=445 (M⁺ 165).

EXAMPLE 7a

Allyl 7-[5-(3-methylisoxazol-5-yl)methoxyimino-2-methyl-8-(2-methylbutyryloxy)-3-oxo-1,2,3,5,6,7,8,8a-octahydro-1-naphthyl]-3-hydroxy-5-oxoheptanoate (allyl ester of Compound No. 140)

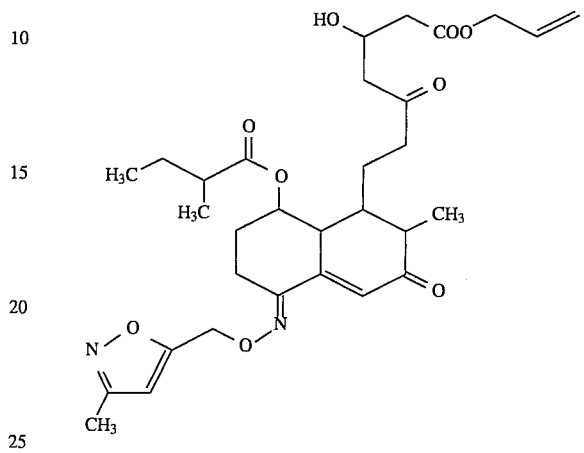

A procedure similar to that described in Example 1a was repeated, except that 727 mg of allyl 7-[5-(3-methylisoxazol-5-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 7) were employed, to obtain 298 mg of the title compound.

Nuclear Magnetic Resonance Spectrum (CDCl₃, 270 MHz) δ ppm: 0.87 (3H, triplet, J=7.3 Hz); 1.01 (3H, doublet, J=7.3 Hz); 1.10 (3H, doublet, J=7.3 Hz); 1.29–1.84 (4H, multiplet); 1.91–2.12 (1H, multiplet); 2.14–2.73 (11H, multiplet, 1H exchangeable with D₂O); 2.31 (3H, singlet); 2.54 (2H, doublet, J=6.4 Hz); 3.08–3.22 (1H, multiplet); 4.40–4.54 (1H, multiplet); 4.62 (2H, doublet, J=5.9 Hz); 5.06–5.39 (2H, multiplet); 5.20 (2H, singlet); 5.44–5.51 (1H, multiplet); 5.83–6.00 (1H, multiplet); 6.13 (1H, singlet); 6.43 (1H, doublet, J=2.4 Hz).

Infrared Absorption Spectrum (CHCl₃) $v_{max}$ cm⁻¹: 3500, 2950, 1730, 1660, 1610, 1410, 1380, 1360, 1290, 1180, 1030, 1000, 900.

Mass spectrum m/z=587 (M⁺ +1).

EXAMPLE 7b

7-[5-(3-Methylisoxazol-5-yl)methoxyimino-
2-methyl-8-(2-methylbutyryloxy)-3-oxo-
1,2,3,5,6,7,8,8a-octahydro-1-naphthyl]-3-hydroxy-
5-oxoheptanoic acid (Compound No. 140)

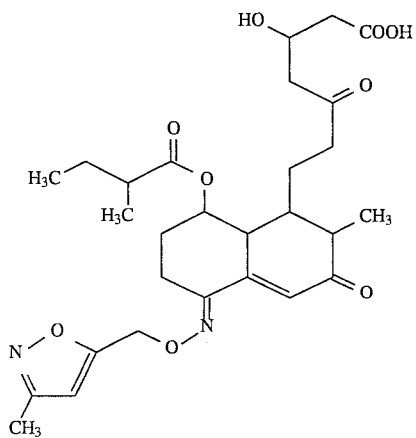

A procedure similar to that described in Example 1b was repeated, except that 285 mg of allyl 7-[5-(3-methylisoxazol-5-yl)methoxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 7a) were employed, to obtain 148 mg of the title compound.

Nuclear Magnetic Resonance Spectrum (CDCl$_3$, 270 MHz) δ ppm: 0.88 (3H, triplet, J=7.3 Hz); 1.01 (3H, doublet, J=7.3 Hz); 1.10 (3H, doublet, J=7.3 Hz); 1.32–1.85 (4H, multiplet); 1.92–2.11 (1H, multiplet); 2.15–3.02 (10H, multiplet, 2H exchangeable with D$_2$O); 2.32 (3H, singlet); 2.57 (2H, doublet, J=6.8 Hz); 2.61 (2H, doublet, J=5.9 Hz); 3.08–3.23 (1H, multiplet); 4.42–4.54 (1H, multiplet); 5.20 (2H, singlet); 5.43–5.51 (1H, multiplet); 6.13 (1H, singlet); 6.49 (1H, doublet, J=2.4 Hz).

Infrared Absorption Spectrum (CHCl$_3$) ν$_{max}$ cm$^{-1}$: 3500, 2950, 1720, 1660, 1600, 1410, 1380, 1290, 1180, 1150, 1130, 1000.

Mass spectrum m/z=546 (M$^+$).

EXAMPLE 8a

Allyl 7-[5-(2-thienyl)methoxyimino-2-methyl-
8-(2-methylbutyryloxy)-3-oxo-1,2,3,5,6,7,8,8a-
octahydro-1-naphthyl]-3-hydroxy-5-oxoheptanoate
(allyl ester of Compound No. 137)

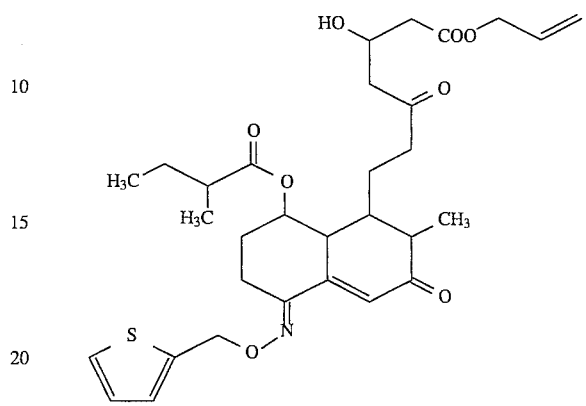

A procedure similar to that described in Example 1a was repeated, except that 1.27 g of allyl 7-[5-(2-thienyl) methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 8) were employed, to obtain 450 mg of the title compound.

Nuclear Magnetic Resonance Spectrum (CDCl$_3$, 270 MHz) δ ppm: 0.86 (3H, triplet, J=7.5 Hz); 1.02 (3H, doublet, J=7.3 Hz); 1.10 (3H, doublet, J=6.8 Hz); 1.36–1.80 (6H, multiplet, 1H exchangeable with D$_2$O); 1.94–2.08 (2H, multiplet); 2.14–2.71 (8H, multiplet); 2.62 (2H, doublet, J=4.3 Hz); 3.08–3.17 (1H, multiplet); 4.42–4.51 (1H, multiplet); 4.62 (2H, doublet, J=5.8 Hz); 5.23–5.36 (4H, multiplet); 5.46 (1H, singlet); 5.86–5.99 (1H, multiplet); 6.56 (1H, doublet, J=2.4 Hz); 6.97–7.00 (1H, multiplet); 7.07–7.09 (1H, multiplet); 7.30–7.32 (1H, multiplet).

Infrared Absorption Spectrum (CHCl$_3$) ν$_{max}$ cm$^{-1}$: 3525, 2950, 1725, 1660, 1460, 1410, 1180, 1150, 1000.

Mass spectrum m/z=587 (M$^+$).

EXAMPLE 8b

7-[5-(2-Thienyl)methoxyimino-2-methyl-
8-(2-methylbutyryloxy)-3-oxo-1,2,3,5,6,7,8,8a-
octahydro-1-naphthyl]-3-hydroxy-5-oxoheptanoic
acid (Compound No. 137)

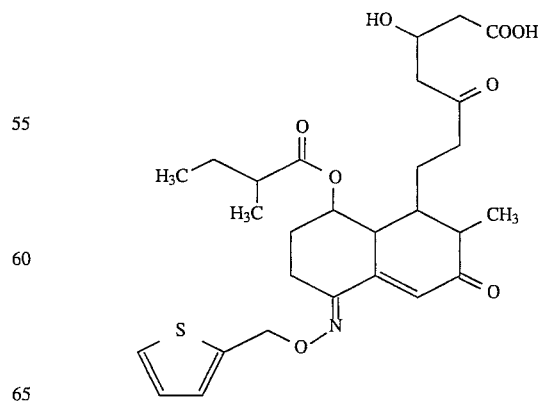

A procedure similar to that described in EXample 1b was repeated, except that 355 mg of allyl 7-[5-(2-thienyl) methoxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 8a) were employed, to obtain 311 mg of the title compound.

Nuclear Magnetic Resonance Spectrum (CDCl₃, 270 MHz) δ ppm: 0.86 (3H, triplet, J=7.3 Hz); 1.02 (3H, doublet, J=7.3 Hz); 1.08 (3H, doublet, J=6.8 Hz); 1.37–1.80 (4H, multiplet); 1.95–2.66 (11H, multiplet, 2H exchangeable with D₂O); 2.55 (2H, doublet, J=6.3 Hz); 2.64 (2H, doublet, J=4.3 Hz); 3.09–3.17 (1H, multiplet); 4.42–4.52 (1H, multiplet); 5.33 (2H, doublet, J=0.9 Hz); 5.47 (1H, singlet); 6.57 (1H, doublet, J=2.9 Hz); 6.97–7.01 (1H, multiplet); 7.07–7.09 (1H, multiplet); 7.30–7.33 (1H, multiplet).

Infrared Absorption Spectrum (CHCl₃) ν$_{max}$ cm⁻¹: 3500, 2950, 1725, 1660, 1460, 1430, 1375, 1220, 1180, 1150, 1000.

Mass spectrum m/z=485 (M⁺ –62).

EXAMPLE 9a

Allyl 7-[5-(isoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoate (allyl ester of Compound No. 138)

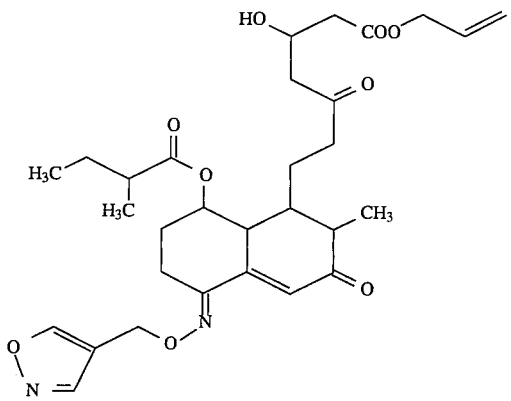

A procedure similar to that described in Example 1a was repeated, except that 630 mg of allyl 7-[5-(isoxazol-4-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 9) were employed, to obtain 208 mg of the title compound.

Nuclear Magnetic Resonance Spectrum (CDCl₃, 270 MHz) δ ppm: 0.87 (3H, triplet, J=7.3 Hz); 1.01 (3H, doublet, J=7.3 Hz); 1.10 (3H, doublet, J=6.8 Hz); 1.40–1.72 (4H, multiplet); 1.98–2.04 (2H, multiplet); 2.20–2.56 (9H, multiplet, 1H exchangeable with D₂O); 2.61–2.65 (2H, multiplet); 3.04–3.12 (1H, multiplet); 3.33 (1H, singlet, exchangeable with D₂O); 4.45–4.49 (1H, multiplet); 4.60–4.63 (2H, multiplet); 5.09 (2H, singlet); 5.84–5.97 (1H, multiplet); 6.49 (1H, doublet, J=2.4 Hz); 6.48 (1H, singlet); 8.34 (1H, singlet).

Infrared Absorption Spectrum (CHCl₃) ν$_{max}$ cm⁻¹: 3525, 2950, 1710, 1660, 1370, 1180, 980.

Mass spectrum m/z=515 (M⁺ –57), 474, 452, 434, 389, 354, 342.

EXAMPLE 9b

7-[5-(Isoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid (Compound No. 138)

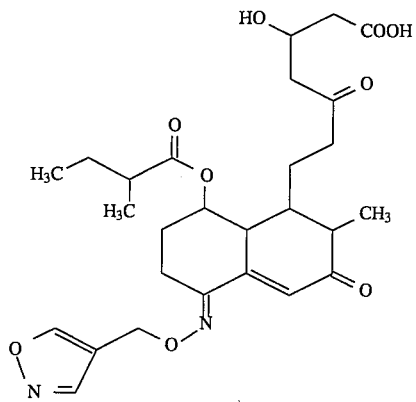

A procedure similar to that described in Example 1b was repeated, except that 196 mg of allyl 7-[5-(isoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 9a) were employed, to obtain 171 mg of the title compound.

Nuclear Magnetic Resonance Spectrum (CDCl₃, 270 MHz) δ ppm: 0.87 (3H, triplet, J=7.3 Hz); 0.95 (3H, doublet, J=7.3 Hz); 1.10 (3H, doublet, J=6.8 Hz); 1.38–1.79 (5H, multiplet); 1.97–2.09 (2H, multiplet); 2.16–2.67 (10H, multiplet); 4.00 (2H, broad, 2H exchangeable with D₂O); 4.44–4.49 (1H, multiplet); 5.09 (2H, singlet); 5.49 (1H, singlet); 6.50 (1H, doublet, J=2.4 Hz); 6.48 (1H, singlet); 8.34 (1H, singlet).

Infrared Absorption Spectrum (CHCl₃) ν$_{max}$ cm⁻¹: 3525, 2950, 1710, 1660, 1370, 1180, 980.

Mass spectrum m/z=485 (M⁺ –47), 435, 393, 372, 322, 314.

EXAMPLE 9c

Sodium 7-[5-(isoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoate (sodium salt of Compound No. 138)

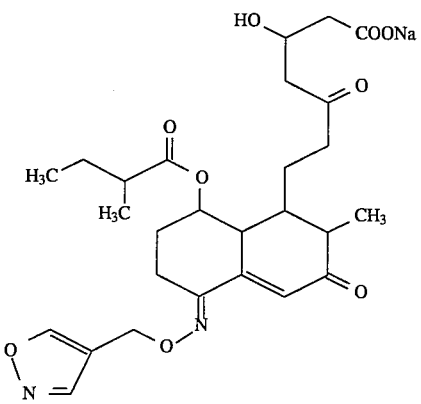

151 mg of 7-[5-(isoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid (prepared as described in Example 9b) were dissolved in 2.5 ml of a 1:1 by volume. mixture of dioxane and water. 2.7 ml of a 0.1N aqueous solution of sodium hydroxide were then added dropwise over a period of 5 minutes at 0° C. to the solution, and the resulting mixture was stirred for 1 hour at room temperature. At the end of this time, the solution was freeze-dried, to obtain 153 mg of the title compound as a colorless moisture sensitive powder.

EXAMPLE 10a

Allyl 7-[5-(5-methylisoxazol-3-yl)methoxyimino-2-methyl-8-(2-methylbutyryloxy)-3-oxo-1,2,3,5,6,7,8,8a-octahydro-1-naphthyl]-3-hydroxy-5-oxoheptanoate (allyl ester of Compound No. 139)

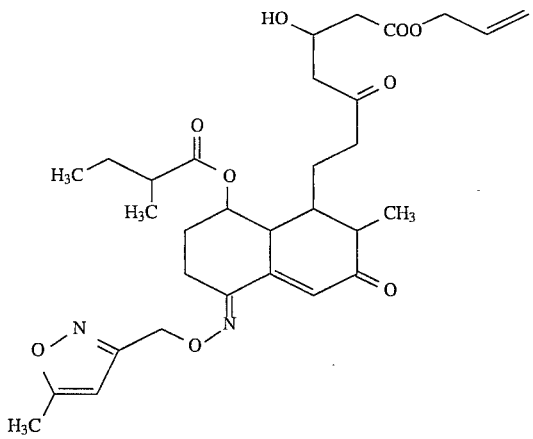

A procedure similar to that described in Example was repeated, except that 843 mg of allyl 7-[5-(5-methylisoxazol-3-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 10) were employed, to obtain 310 mg of the title compound.

Nuclear Magnetic Resonance Spectrum (CDCl$_3$, 270 MHz) δ ppm: 0.87 (3H, triplet, J=7.3 Hz); 1.01 (3H, doublet, J=7.3 Hz); 1.10 (3H, doublet, J=7.3 Hz); 1.33–1.85 (4H, multiplet); 1.92–2.11 (1H, multiplet); 2.15–2.74 (11H, multiplet, 1H exchangeable with D$_2$O); 2.44 (3H, singlet); 2.54 (2H, doublet, J=6.3 Hz); 3.08–3.21 (1H, multiplet); 4.41–4.54 (1H, multiplet); 4.63 (2H, doublet, J=5.9 Hz); 5.14–5.39 (2H, multiplet); 5.21 (2H, singlet); 5.44–5.51 (1H, multiplet); 5.84–6.00 (1H, multiplet); 6.05 (1H, singlet); 6.51 (1H, doublet, J=2.4 Hz).

Infrared Absorption Spectrum (CHCl$_3$) ν$_{max}$ cm$^{-1}$: 3500, 2950, 1730, 1660, 1600, 1460, 1380, 1300, 1180, 1150, 1040, 1010, 980.

Mass spectrum m/z=587 (M$^+$ +1).

EXAMPLE 10b

7-[5-(5-Methylisoxazol-3-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid (Compound No 139)

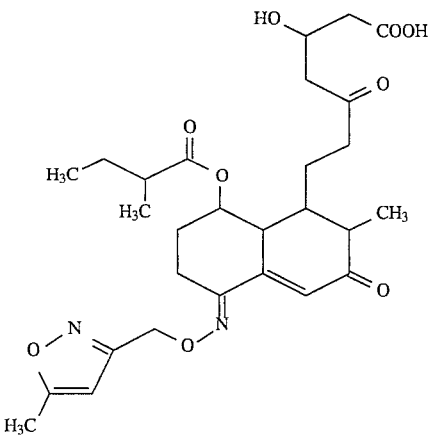

A procedure similar to that described in Example 1b was repeated, except that 290 mg of allyl 7-[5-(5-methylisoxazol-3-yl)methoxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 10a) were employed, to obtain 201 mg of the title compound.

Nuclear Magnetic Resonance Spectrum (CDCl$_3$, 270 MHz) δ ppm: 0.87 (3H, triplet, J=7.3 Hz); 1.01 (3H, doublet, J=7.3 Hz); 1.10 (3H, doublet, J=7.3 Hz); 1.33–2.54 (14H, multiplet, 1H exchangeable with D$_2$O); 2.44 (3H, singlet); 2.57 (2H, doublet, J=6.4 Hz); 2.66 (2H, doublet, J=5.9 Hz); 3.11–3.20 (1H, multiplet); 3.27–3.83 (1H, multiplet, exchangeable with D$_2$O); 4.42–4.53 (1H, multiplet); 5.20 (2H, singlet); 5.45–5.52 (1H, multiplet); 6.04 (1H, singlet); 6.51 (1H, doublet, J=2.4 Hz).

Infrared Absorption Spectrum (CHCl$_3$) ν$_{max}$ cm$^{-1}$: 3500, 2950, 1720, 1660, 1600, 1380, 1340, 1290, 1180, 1150, 1040, 1000, 970, 900.

Mass spectrum m/z=484 (M$^+$ −62).

EXAMPLE 11a

Allyl 7-[5-(3,5-dimethylisoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoate (allyl ester of Compound No. 141)

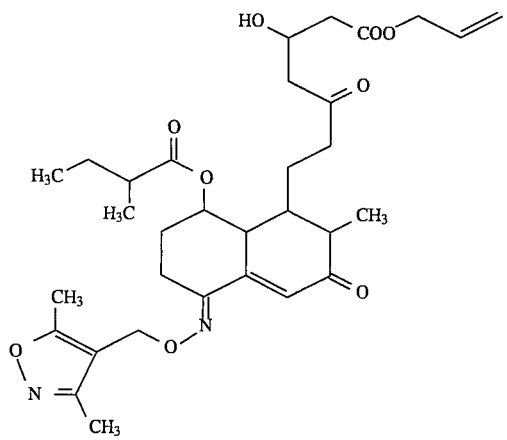

A procedure similar to that described in Example 1a was repeated, except that 243 mg of allyl 7-[5-(3,5-dimethylisoxazol-4-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 11) were employed, to obtain 95 mg of the title compound.

Nuclear Magnetic Resonance Spectrum ($CDCl_3$, 270 MHz) δ ppm: 0.87 (3H, triplet, J=7.3 Hz); 1.01 (3H, doublet, J=7.3 Hz); 1.10 (3H, doublet, J=7.3 Hz); 1.34–1.78 (4H, multiplet); 1.91–2.68 (12H, multiplet, 1H exchangeable with $D_2O$); 2.28 (3H, singlet); 2.41 (3H, singlet); 2.53 (2H, doublet, J=6.4 Hz); 3.04 (1H, doublet of doublets, J=6.8 & 17.9 Hz); 4.41–4.52 (1H, multiplet); 4.61 (2H, doublet, J=5.4 Hz); 4.94 (2H, singlet); 5.22–5.38 (2H, multiplet); 5.43–5.49 (1H, multiplet); 5.84–6.00 (1H, multiplet); 6.47 (1H, doublet, J=2.9 Hz).

Infrared Absorption Spectrum ($CHCl_3$) $v_{max}$ $cm^{-1}$: 3500, 2830, 1720, 1660, 1460, 1420, 1180, 1150, 1000.

High resolution mass spectrum: Calculated for $C_{32}H_{44}O_9N_2$: 600.3031 ($M^+$). Found: 600.3033.

EXAMPLE 11b

7-[5-(3,5-Dimethylisoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid (Compound No. 141)

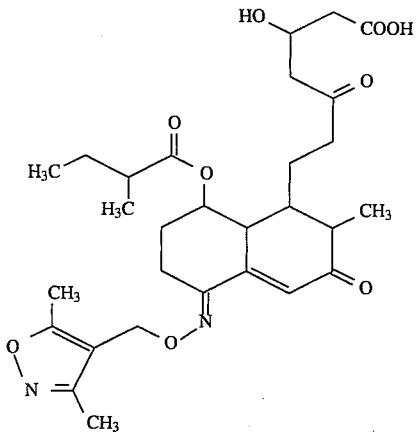

A procedure similar to that described in Example 1b was repeated, except that 218 mg of allyl 7-[5-(3,5-dimethylisoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoate (prepared as described in Example 11a) were employed, to obtain 155 mg of the title compound.

Nuclear Magnetic Resonance Spectrum ($CDCl_3$, 270 MHz) δ ppm: 0.87 (3H, triplet, J=7.3 Hz); 1.01 (3H, doublet, J=7.3 Hz); 1.10 (3H, doublet, J=7.3 Hz); 1.38–1.80 (4H, multiplet); 1.92–3.20 (11H, multiplet, 2H exchangeable with $D_2O$); 2.28 (3H, singlet); 2.41 (3H, singlet); 2.56 (2H, doublet, J=6.4 Hz); 2.65 (2H, doublet, J=6.3 Hz); 3.04 (1H, doublet of doublets, J=6.8 & 17.9 Hz); 4.41–4.53 (1H, multiplet); 4.95 (2H, singlet); 5.42–5.50. (1H, multiplet); 6.48 (1H, doublet, J=2.9 Hz).

Infrared Absorption Spectrum ($CHCl_3$) $v_{max}$ $cm^{-1}$: 3500, 2950, 1720, 1660, 1460, 1420, 1380, 1260, 1180, 1150, 1000.

Mass spectrum m/z=498 ($M^+$ −62).

EXAMPLE 11c

Sodium 7-[5-(3,5-dimethylisoxazol-4-yl)methoxyimino-2-methyl-8-(2-methylbutyryloxy)-3-oxo-1,2,3,5,6,7,8,8a-octahydro-1-naphthyl]-3-hydroxy-5-oxoheptanoate (sodium salt of Compound No. 141)

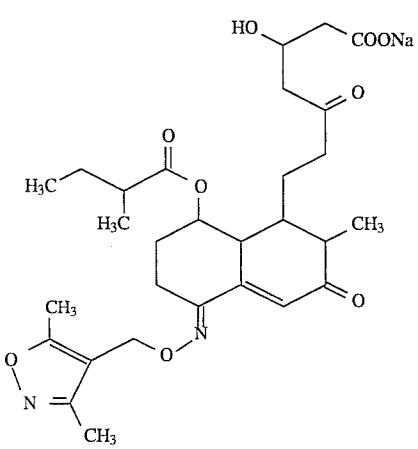

139 mg of 7-[5-(3,5-dimethylisoxazol-4-yl)methoxy-imino-2-methyl-8-(2-methylbutyryloxy)-3-oxo-1,2,3,5,6,7,8,8a-octahydro-1-naphthyl]-3-hydroxy-5-oxoheptanoic acid (prepared as described in Example 11b) were dissolved in 2.7 ml of a 1:1 by volume mixture of dioxane and water. 2.35 ml of a 0.1N aqueous solution of sodium hydroxide were added dropwise over a period of minutes at 0° C. to the solution, which was then stirred for 1 hour at room temperature. At the end of this time, the solution was freeze-dried, to obtain 140 mg of the title compound as a colorless moisture sensitive powder.

EXAMPLE 12a

Allyl 7-[5-hexylimino-2-methyl-8-(2-methylbutyryloxy)-3-oxo-1,2,3,5,6,7,8,8a-octahydro-1-naphthyl]-3-hydroxy-5-oxoheptanoate (allyl este of Compound No. 142)

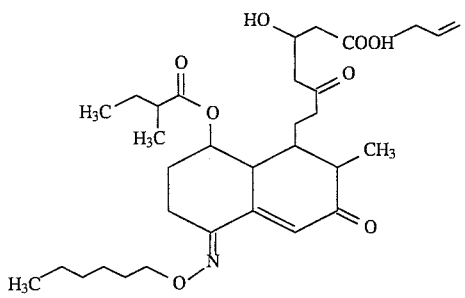

A procedure similar to that described in Example 1a was repeated, except that 515 mg of allyl 7-[5-hexylimino-2-methyl-8-(2-methylbutyryloxy)-3-oxo-1,2,3,5,6,7,8,8a-octahydro-1-naphthyl]-3,5-dihydroxyheptanoate (prepared as described in Preparation 12) were employed, to obtain 149 mg of the title compound.

Nuclear Magnetic Resonance Spectrum (CDCl$_3$, 270 MHz) δ ppm: 0.87 (3H, triplet, J=7.3 Hz); 0.89 (3H, doublet, J=6.4 Hz); 1.00 (3H, doublet, J=7.3 Hz); 1.11 (3H, doublet, J=7.3 Hz); 1.23–1.80 (12H, multiplet); 1.93–2.09 (3H, multiplet, 1H exchangeable with D$_2$O); 2.13–2.56 (9H, multiplet); 2.61–2.72 (2H, multiplet); 3.09–3.17 (1H, multiplet); 4.11–4.21 (2H, multiplet); 4.43–4.50 (1H, multiplet); 4.60–4.63 (2H, multiplet); 5.23–5.37 (2H, multiplet); 5.47 (1H, singlet); 5.85–5.97 (1H, multiplet); 6.52 (1H, doublet, J=2.9 Hz).

Infrared Absorption Spectrum (CHCl$_3$) $\nu_{max}$ cm$^{-1}$: 3525, 2925, 1720, 1660, 1460, 1380, 1180, 1150, 1020, 980.

High resolution mass spectrum: Calculated for C$_{32}$H$_{49}$O$_9$N$_2$: 576.3502 (M$^+$ +1); Found: 576.3498.

EXAMPLE 12b

7-[5-Hexylmethoxyimino-2-methyl-8-(2-methylbutyryloxy)-3-oxo-1,2,3,5,6,7,8,8a-octahydro-1-naphthyl]-3-hydroxy-5-oxoheptanoic acid (Compound No. 142)

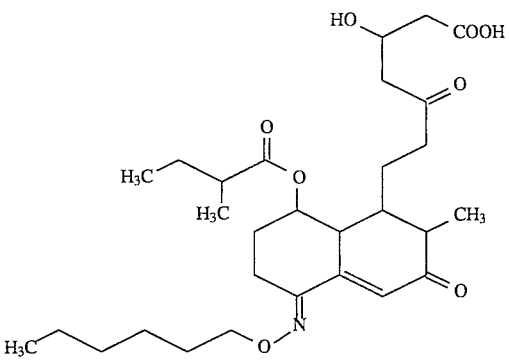

A procedure similar to that described in Example 1b was repeated, except that 140 mg of allyl 7-[5-hexylmethoxy-imino-2-methyl-8-(2-methylbutyryloxy)-3-oxo-1,2,3,5,6,7,8,8a-octahydro-1-naphthyl]-3-hydroxy-5-oxo-heptanoate (prepared as described in Example 12a) were employed, to obtain 106 mg of the title compound.

Nuclear Magnetic Resonance Spectrum (CDCl$_3$, 270 MHz) δ ppm: 0.88 (3H, triplet, J=7.3 Hz); 0.89 (3H, doublet, J=6.4 Hz); 1.01 (3H, doublet, J=7.3 Hz); 1.11 (3H, doublet, J=6.8 Hz); 1.23–1.81 (13H, multiplet); 1.98–2.10 (2H, multiplet); 2.14–2.67 (10H, multiplet); 3.09–3.19 (1H, multiplet); 3.72 (2H, broad, 1H exchangeable with D$_2$O); 4.08–4.24 (2H, multiplet); 4.44–4.53 (1H, multiplet); 5.49 (1H, singlet); 6.53 (1H, doublet, J=2.4 Hz).

Infrared Absorption Spectrum (CHCl$_3$) $\nu_{max}$ cm$^{-1}$: 3500, 2925, 1720, 1660, 1460, 1380, 1180, 1150, 1020, 900.

Mass spectrum m/z=473 (M$^+$ −62), 432, 371, 340.

EXAMPLE 13

Benzyl
7-[5-(1,3-dioxan-5-yl)methoxyimino-2-methyl-
8-(2-methylbutyryloxy)-3-oxo-1,2,3,5,6,7,8,8a-
octahydro-1-naphthyl]-3-hydroxy-5-oxoheptanoate
(benzyl ester of Compound No. 54)

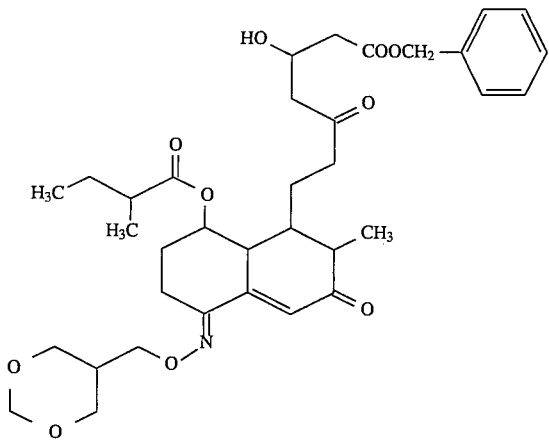

A procedure similar to that described in Example 1a was repeated, except that 11.7 g of benzyl 7-[5-(1,3-dioxan-5-yl)methoxyimino-2-methyl-8-(2-methylbutyryloxy)-3-oxo-1,2,3,5,6,7,8,8a-octahydro-1-naphthyl]-3,5-dihydroxyheptanoate (prepared as described in Preparation 13) were employed, to obtain 5.3 g of the title compound.

Nuclear Magnetic Resonance Spectrum (CDCl$_3$, 270 MHz) δ ppm: 0.87 (3H, triplet, J=7.3 Hz); 0.99 (3H, doublet, J=7.3 Hz); 1.11 (3H, doublet, J=7.3 Hz); 1.37 1.72 (4H, multiplet); 1.90–2.09 (2H, multiplet); 2.13–2.72 (12H, multiplet); 3.04–3.18 (1H, multiplet); 3.33 (1H, broad singlet, exchangeable with D$_2$O); 3.75 (2H, doublet of doublets, J=6.3 & 11.6 Hz); 4.02 (2H, doublet of doublets, J=4.0 & 11.9 Hz); 4.25 (2H, doublet, J=6.6 Hz); 4.42–4.54 (1H, multiplet); 4.85 (2H, AB-quartet, J=5.9 & 19.8 Hz); 5.15 (2H, singlet); 5.48 (1H, broad singlet); 6.49 (1H, doublet, J=2.0 Hz); 7.36 (5H, singlet).

PREPARATION 1

Allyl 7-[5-benzyloxyimino-2-methyl-
8-(2-methylbutyryoxy)-3-oxo-1,2,3,5,6,7,8,8a-
octahydro-1-naphthyl]-3,5-dihydroxyheptanoate

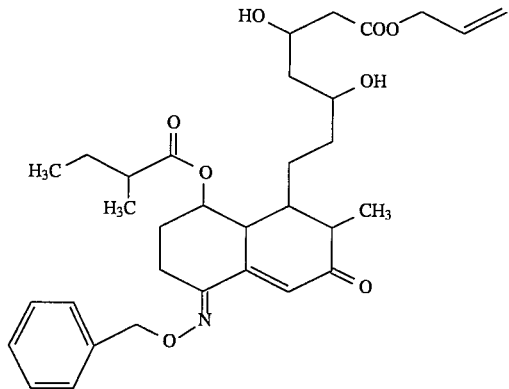

0.98 g (1.87 mmole) of {2-[5-benzyloxyimino-2-methyl-8-(2-methylbutyryloxy)-3-oxo-1,2,3,5,6,7,8,8a-octahydro-1-naphthyl]ethyl}-4-hydroxy-3,4,5,6-tetra-hydro-2 H-pyran-2-one was dissolved in 20 ml of a 1:1 by volume mixture of dioxane and water. 19.6 ml of a 0.1N solution of sodium hydroxide was then added dropwise to the solution over a period of 2.5 hours at 0° C.; it was then stirred for 30 minutes at the same temperature and then for a further 1 hour at room temperature. At the end of this time, the solution was freeze-dried. The resulting sodium salt was dissolved in 11 ml of dimethylformamide, and then 1.62 ml (18.7 mmole) of allyl bromide was added, and the mixture was stirred for 17 hours under an atmosphere of nitrogen. At the end of this time, the dimethylformamide was removed from the reaction mixture by distillation under reduced pressure. 40 ml of water were added to the residue and the resulting mixture was extracted with ethyl acetate (twice, each time with 30 ml). The ethyl acetate extract was then washed with a saturated aqueous solution of sodium chloride, dried over anhydrous magnesium sulfate, filtered and condensed by evaporation under reduced pressure. The resulting oily residue was purified by flash column chromatography through silica gel, using a 2:1 by volume mixture of ethyl acetate and hexane as the eluent, to obtain 0.90 g (yield 84%) of the title compound.

Nuclear Magnetic Resonance Spectrum (CDCl$_3$, 270 MHz) δ ppm: 0.86 (3H, triplet, J=7.3 Hz); 1.04 (3H, doublet, J=7.3 Hz); 1.10 (3H, doublet, J=7.3 Hz); 1.15–1.84 (8H, multiplet); 1.91–2.08 (1H, multiplet); 2.16–2.79 (8H, multiplet, 2H exchangeable with D$_2$O); 2.52 (2H, doublet, J=6.4 Hz); 3.10–3.22 (1H, multiplet); 3.78–3.86 (1H, multiplet); 4.21–4.32 (1H, multiplet); 4.62 (2H, doublet, J=5.9 Hz); 5.12–5.39 (2H, multiplet); 5.20 (2H, doublet, J=2.9 Hz); 5.47–5.53 (1H, multiplet); 5.82–6.01 (1H, multiplet); 6.52 (1H, doublet, J=2.5 Hz); 7.29–7.43 (5H, multiplet).

Infrared Absorption Spectrum (CHCl$_3$) ν$_{max}$ cm$^{-1}$: 3500, 2940, 1720, 1660, 1450, 1370, 1180, 1150, 1010, 980, 910.

Mass spectrum m/z=583 (M$^+$).

PREPARATION 2

Allyl 7-[5-(furan-2-yl)methoxyimino-2-methyl-
8-(2-methylbutyryloxy)-3-oxo-1,2,3,5,6,7,8,8a-
octahydro-1-naphthyl]-3,5-dihydroxyheptanoate

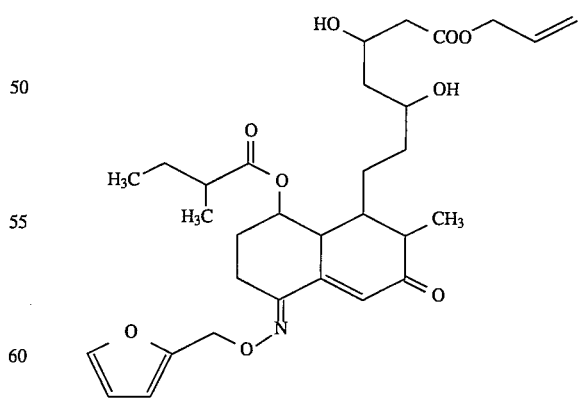

A procedure similar to that described in Preparation 1 was repeated, but using 1.31 g of {2-[5-(furan-2-yl)methoxy-imino-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 1.34 g of the title compound.

Nuclear Magnetic Resonance Spectrum (CDCl$_3$, 270 MHz) δ ppm: 0.86 (3H, triplet, J=7.3 Hz); 1.02 (3H, doublet, J=7.3 Hz); 1.09 (3H, doublet, J: 7.3 Hz); 1.13–1.84 (8H, multiplet); 1.91–2.68 (11H, multiplet, 2H exchangeable with D$_2$O); 3.07–3.20 (1H, multiplet); 3.73–3.88 (1H, multiplet); 4.20–4.33 (1H, multiplet); 4.62 (2H, doublet, J=5.9 Hz); 5.03–5.39 (4H, multiplet); 5.45–5.55 (1H, multiplet); 5.84–6.00 (1H multiplet); 6.32–6.56 (3H, multiplet); 7.43 (1H, doublet, J=2.4 Hz).

Infrared Absorption Spectrum (CHCl$_3$) $v_{max}$ cm$^{-1}$: 3500, 2950, 2850, 1720, 1660, 1500, 1430, 1370, 1350, 1320, 1180, 1150, 1080, 1000, 980, 920, 880.

Mass spectrum m/z=556 (M$^+$ −17)

PREPARATION 3

Allyl 7-[5-(1,3-dioxan-5-yl)methoxyimino-2-methyl-8-(2-methylbutyryloxy)-3-oxo-1,2,3,5,6,7,8,8a-octahydro-1-naphthyl]-3,5-dihydroxyheptanoate

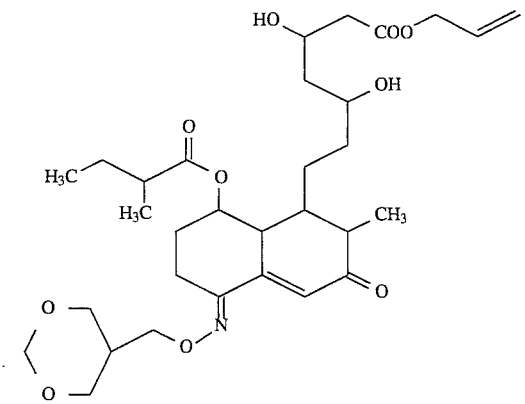

A procedure similar to that described in preparation was repeated, but using 10.0 g of {2-[5-(1,3-dioxan-5-yl) methoxyimino-2-methyl-8-(2-methylbutyryloxy)-3-oxy-1,2,3,5,6,7,8,8a-octahydro-1-naphthyl]ethyl}-4-hydroxy-3,4,5,6-tetrahydro-2H-pyran-2-one, to obtain 10.6 g of the title compound.

Nuclear Magnetic Resonance Spectrum (CDCl$_3$, 270 MHz) δ ppm: 0.87 (3H, triplet, J=7.3 Hz); 1.01 (3H, doublet, J=7.3 Hz); 1.10 (3H, doublet, J=7.3 Hz); 1.15–2.08 (11H, multiplet, 2H exchangeable with D$_2$O); 2.19–2.60 (7H, multiplet); 2.52 (2H, doublet, J=5.9 Hz); 3.12 (1H, doublet of doublets, J=5.9 & 16.1 Hz); 3.71–3.87 (1H, multiplet); 3.74 (2H, doublet of doublets, J=6.4 & 11.7 Hz); 3.98–4.07 (2H, multiplet); 4.22–4.32 (1H, multiplet); 4.25 (2H, doublet, J=7.3 Hz); 4.62 (2H, doublet, J=5.9 Hz); 4.81 (1H, doublet, J=6.6 Hz); 4.88 (1H, doublet, J=5.9 Hz); 5.23–5.38 (2H, multiplet); 5.50–5.55 (1H, multiplet); 5.86–5.98 (1H, multiplet); 6.49 (1H, doublet, J=2.2 Hz).

Infrared Absorption Spectrum (CHCl$_3$) $v_{max}$ cm$^{-1}$: 3500, 2960, 2930, 2850, 1720, 1660, 1460, 1370, 1290, 1180, 1150, 1030, 980, 930, 880, 840.

Mass spectrum m/z=593 (M$^+$)

PREPARATION 4

Allyl 7-[5-(2-ethoxybenzyloxyimino)-2-methyl-8-(2-methylbutyryloxy)-3-oxo-1,2,3,5,6,7,8,8a-octahydro-1-naphthyl]-3,5-dihydroxyheptanoate

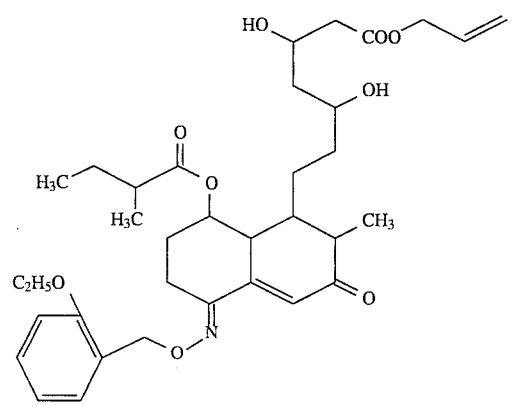

A procedure similar to that described in preparation 1 was repeated, but using 690 mg of {2-[5-(2-ethoxybenzylimino)-2-methyl-8-(2-methylbutyryloxy)-3-oxo-1,2,3,5,6,7,8,8a-octahydro-1-naphthyl]ethyl]-4-hydroxy-3,4,5,6-tetrahydro-2H-pyran-2-one, to obtain 680 mg of the title compound.

Nuclear Magnetic Resonance Spectrum (CDCl$_3$, 270 MHz) δ ppm: 0.86 (3H, triplet, J=7.3 Hz); 1.02 (3H, doublet, J=7.3 Hz); 1.11 (3H, doublet, J=6.8 Hz); 1.36–1.81 (12H, multiplet); 1.92–2.04 (2H, multiplet); 2.17–2.60 (8H, multiplet, 1H exchangeable with D$_2$O); 3.15–3.25 (1H, multiplet); 3.78–3.83 (1H, multiplet); 4.02–4.16 (2H, multiplet); 4.24–4.29 (1H, multiplet); 4.63 (2H, doublet, J=5.8 Hz); 5.23–5.37 (4H, multiplet); 5.51 (1H, singlet); 5.84–5.99 (1H, multiplet); 6.54 (1H, doublet, J=2.4 Hz); 6.86–6.96 (2H, multiplet); 7.23–7.34 (2H, multiplet).

Infrared Absorption Spectrum (CHCl$_3$) $v_{max}$ cm$^{-1}$: 3500, 2960, 1725, 1660, 1490, 1450, 1180, 1150, 1010.

Mass spectrum m/z=627 (M$^+$).

PREPARATION 5

Allyl 7-[5-(2-chlorobenzyloxyimino)-2-methyl-8-(2-methylbutyryloxy)-3-oxo-1,2,3,5,6,7,8,8a-octahydro-1-naphthyl]-3,5-dihydroxyheptanoate

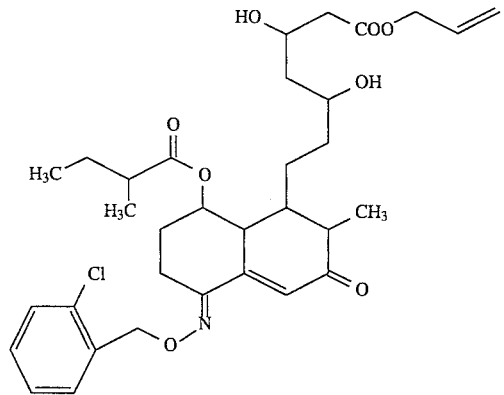

A procedure similar to that described in Preparation 1 was repeated, but using 970 mg of {2-[5-(2-chlorobenzyloxy-imino)-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 970 mg of the title compound.

Nuclear Magnetic Resonance Spectrum (CDCl$_3$, 270 MHz) δ ppm: 0.86 (3H, triplet, J=7.5 Hz); 1.02 (3H, doublet, J=7.3 Hz); 1.11 (3H, doublet, J=6.8 Hz); 1.36–1.82 (SH, multiplet); 1.94–2.01 (1H, multiplet); 2.19–2.60 (10H, multiplet, 1H exchangeable with D$_2$O); 3.15–3.25 (1H, multiplet); 3.76–3.85 (1H, multiplet); 4.22–4.31 (1H, multiplet); 4.63 (2H, doublet, J=5.8 Hz); 5.23–5.37 (4H, multiplet); 5.51 (1H, singlet); 5.84–5.99 (1H, multiplet); 6.52 (1H, doublet, J=2.4 Hz); 7.24–7.42 (4H, multiplet).

Infrared Absorption Spectrum (CHCl$_3$) ν$_{max}$ cm$^{-1}$: 3500, 2925, 1720, 1660, 1440, 1180, 1150, 1010.

Mass spectrum m/z=541 (M$^+$ −77).

PREPARATION 6

Allyl 7-[5-(2,6-dichlorobenzyloxyimino)-2-methyl-8-(2-methylbutyryloxy)-3-oxo-1,2,3,5,6,7,8,8a-octahydro-1-naphthyl]-3,5-dihydroxyheptanoate

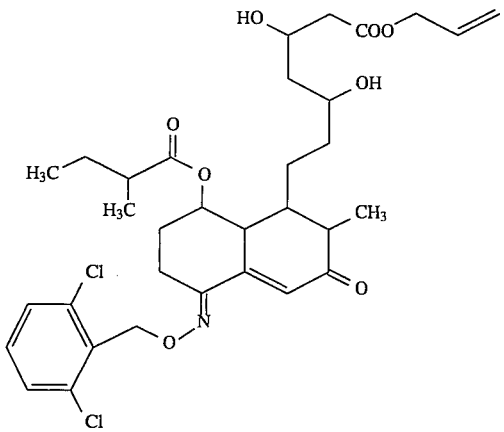

A procedure similar to that described in Preparation 1 was repeated, but using 1.41 g of {2-[5-(2,6-dichlorobenzyloxy imino)-2-methyl-8-(2-methylbutyryloxy)-3-oxo-1,2,3,5,6,7,8,8a-octahydro-1-naphthyl]ethyl}-4-hydroxy-3,4,5,6-tetrahydro-2M-pyran-2-one, to obtain 1.33 g of the title compound.

Nuclear Magnetic Resonance Spectrum (CDCl$_3$, 270 MHz) δ ppm: 0.86 (3H, triplet, J=7.3 Hz); 1.02 (3H, doublet, J=7.3 Hz); 1.08 (3H, doublet, J=7.3 Hz); 1.13–1.30 (1H, multiplet); 1.31–1.84 (9H, multiplet, 2H exchangeable with D$_2$O); 1.92–2.08 (1H, multiplet); 2.12–2.60 (6H, multiplet); 2.51 (2H, doublet, J=6.4 Hz); 3.05–3.19 (1H, multiplet); 3.72–3.89 (1H, multiplet); 4.20–4.32 (1H, multiplet); 4.62 (2H, doublet, J=5.9 Hz); 5.21–5.57 (3H, multiplet); 5.50 (2H, doublet, J=7.3 Hz); 5.83–6.00 (1H, multiplet); 6.55 (1H, doublet, J=2.4 Hz); 7.18–7.38 (3H, multiplet).

Infrared Absorption Spectrum (CHCl$_3$) ν$_{max}$ cm$^{-1}$: 3500, 2950, 2930, 2900, 1720, 1660, 1580, 1560, 1440, 1370, 1290, 1180, 1150, 1090, 1020, 990, 900, 840.

Mass spectrum m/z=549 (M$^+$ −103).

PREPARATION 7

Allyl 7-[5-(3-methylisoxazol-5-yl)methoxyimino-2-methyl-8-(2-methylbutyryloxy)-3-oxo-1,2,3,5,6,7,8,8a-octahydro-1-naphthyl]-3,5-dihydroxyheptanoate

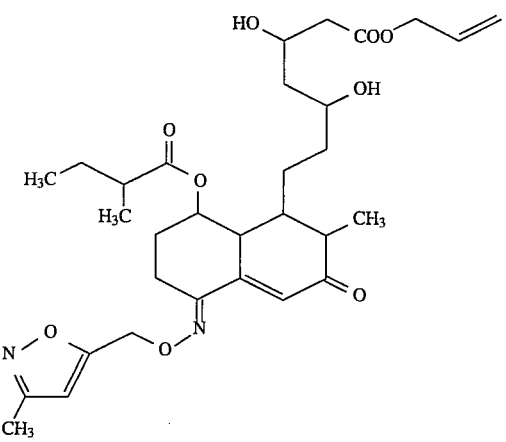

A procedure similar to that described in Preparation 1 was repeated, but using 700 mg of {2-[5-(3-methylisoxazol-5-yl)methoxyimino-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 736 mg of the title compound.

Nuclear Magnetic Resonance Spectrum (CDCl$_3$, 270 MHz) δ ppm: 0.87 (3H, triplet, J=7.3 Hz); 1.02 (3H, doublet, J=7.3 Hz); 1.10 (3H, doublet, J=7.3 Hz); 1.15–1.27 (1H, multiplet); 1.34–1.85 (7H, multiplet); 1.93–2.70 (9H, multiplet, 2H exchangeable with D$_2$O); 2.32 (3H, singlet); 2.51 (2H, doublet, J=6.4Hz); 3.07–3.21 (1H, multiplet); 3.73–3.90 (1H, multiplet); 4.20–4.34 (1H, multiplet); 4.62 (2H, doublet, J=5.4 Hz); 5.10–5.39 (2H, multiplet); 5.20 (2H, singlet); 5.48–5.55 (1H, multiplet); 5.83–6.00 (1H, multiplet); 6.14 (1H, singlet); 6.49 (1H, doublet, J=2.9 Hz).

Infrared Absorption Spectrum (CHCl$_3$) ν$_{max}$ cm$^{-1}$: 3500, 2950, 1730, 1660, 1600, 1370, 1360, 1180, 1150, 1070, 1030, 1000, 980.

Mass spectrum m/z=571 (M$^+$ −17).

PREPARATION 8

Allyl 7-[5-(2-thienyl)methoxyimino-2-methyl-8-(2-methylbutyryloxy)-3-oxo-1,2,3,5,6,7,8,8a-octahydro-1-naphthyl]-3,5-dihydroxyheptanoate

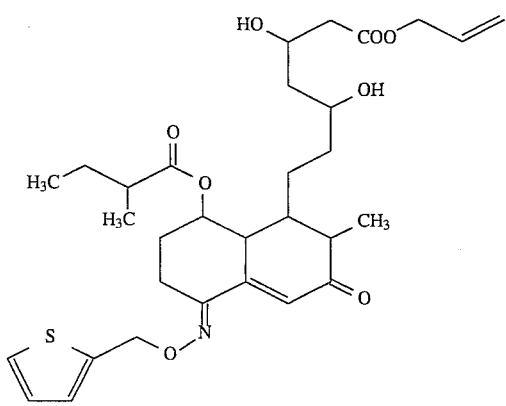

A procedure similar to that described in Preparation 1 was repeated, but using 1.37 g of {2-[5-(2-thienyl)methoxyimino]-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 1.28 g of the title compound.

Nuclear Magnetic Resonance Spectrum (CDCl$_3$, 270 MHz) δ ppm: 0.85 (3H, triplet, J=7.3 Hz); 1.03 (3H, doublet, J=7.3 Hz); 1.10 (3H, doublet, J=6.8 Hz); 1.33–1.80 (8H, multiplet); 1.95–2.58 (9H, multiplet); 3.09–3.18 (1H, multiplet); 3.59 (1H, singlet, exchangeable with D$_2$O); 3.79–3.83 (2H, multiplet, 1H exchangeable with D$_2$O); 4.26–4.29 (1H, multiplet); 4.63 (2H, doublet, J=5.8 Hz); 5.22–5.38 (4H, multiplet); 5.50 (1H, singlet); 5.89–5.99 (1H, multiplet); 6.57 (1H, doublet, J=2.5 Hz); 6.97–7.01 (1H, multiplet); 7.07–7.09 (1H, multiplet); 7.30–7.33 (1H, multiplet).

Infrared Absorption Spectrum (CHCl$_3$) ν$_{max}$ cm$^{-1}$: 3500, 2925, 1725, 1660, 1460, 1180, 1150, 980.

Mass spectrum m/z=513 (M$^+$ −76).

PREPARATION 9

Allyl 7-[5-(isoxazol-4-yl)methoxyimino-2-methyl-8-(2-methylbutyryloxy)-3-oxo-1,2,3,5,6,7,8,8a-octahydro-1-naphthyl]-3,5-dihydroxyheptanoate

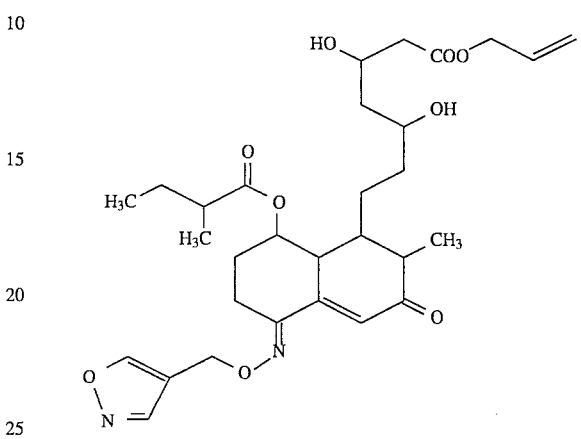

A procedure similar to that described in Preparation 1 was repeated, but using 600 mg of {2-[5-(isoxazol-4-yl) methoxyimino-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 630 mg of the title compound.

Nuclear Magnetic Resonance Spectrum (CDCl$_3$, 270 MHz) δ ppm: 0.87 (3H, triplet, J=7.3 Hz); 1.02 (3H, doublet, J=7.3 Hz); 1.10 (3H, doublet, J=6.8 Hz); 1.16–1.79 (7H, multiplet); 1.96–2.09 (2H, multiplet); 2.15–2.60 (10H, multiplet, 2H exchangeable with D$_2$O); 2.61–2.65 (2H, multiplet); 3.09 (1H, doublet of doublets, J=6.4 & 16.1 Hz); 3.78–3.84 (1H, multiplet); 4.23–4.32 (1H, multiplet); 4.61–4.64 (2H, multiplet); 5.09 (2H, singlet); 5.24–5.37 (2H, multiplet); 5.51 (1H, singlet); 5.85–5.99 (1H, multiplet); 6.50 (1H, doublet, J=2.4 Hz); 8.34 (1H, singlet); 8.48 (1H, singlet).

Infrared Absorption Spectrum (CHCl$_3$) ν$_{max}$ cm$^{-1}$: 3500, 2925, 1715, 1660, 1180, 980.

Mass spectrum m/z=538 (M$^+$ −36), 476, 436, 374, 356.

PREPARATION 10

Allyl 7-[5-(5-methylisoxazol-3-yl)methoxyimino-2-methyl-8-(2-methylbutyryloxy)-3-oxo-1,2,3,5,6,7,8,8a-octahydro-1-naphthyl]-3,5-dihydroxyheptanoate

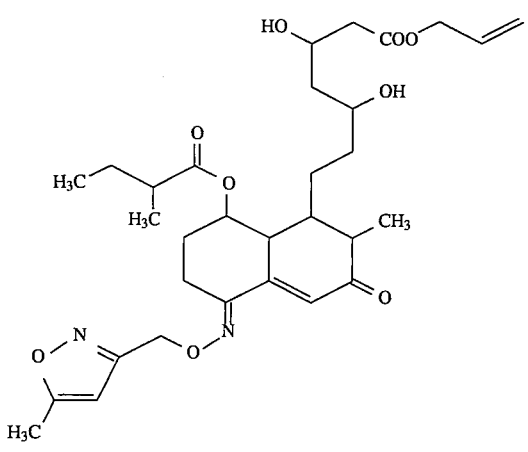

A procedure similar to that described in Preparation 1 was repeated, but using 800 mg of {2-[5-(5-methylisoxazol-3-yl)methoxyimino-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 857 mg of the title compound.

Nuclear Magnetic Resonance Spectrum (CDCl$_3$, 270 MHz) δ ppm: 0.87 (3H, triplet, J=7.3 Hz); 1.02 (3H, doublet, J=7.3 Hz); 1.10 (3H, doublet, J=7.3 Hz); 1.17–1.89 (8H, multiplet); 1.89–2.80 (9H, multiplet, 2H exchangeable with D$_2$O); 2.43 (3H, singlet); 2.51 (2H, doublet, J=6.3 Hz); 3.08–3.22 (1H, multiplet); 3.70–3.90 (1H, multiplet); 4.19–4.33 (1H, multiplet); 4.61 (2H, doublet, J=5.9 Hz); 5.13–5.39 (2H, multiplet); 5.21 (2H, singlet); 5.45–5.56 (1H, multiplet); 5.82–6.00 (1H, multiplet); 6.05 (1H, singlet); 6.51 (1H, doublet, J=2.9 Hz).

Infrared Absorption Spectrum (CHCl$_3$) ν$_{max}$ cm$^{-1}$: 3500, 2900, 1720, 1660, 1600, 1370, 1180, 1150, 1070, 1030, 1000, 980.

Mass spectrum m/z=589 (M$^+$ +1).

PREPARATION 11

Allyl 7-[5-(3,5-dimethylisoxazol-4-yl)methoxyimino-2-methyl-8-(2-methylbutyryloxy)-3-oxo-1,2,3,5,6,7,8,8a-octahydro-1-naphthyl]-3,5-dihydroxyheptanoate

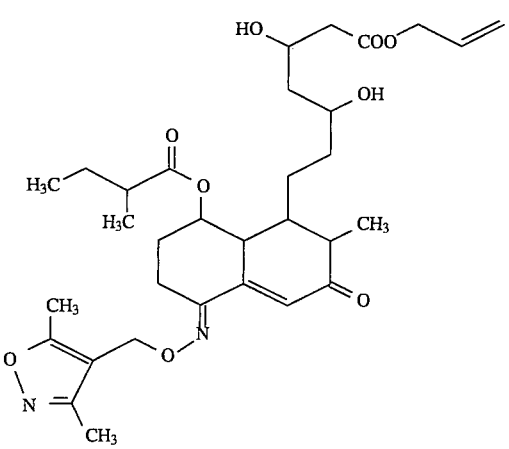

A procedure similar to that described in Preparation 1 was repeated, but using 1.01 g of {2-[5-(3,5-dimethylisoxazol-4-yl)methoxyimino-2-methyl-8-(2-methylbutyryloxy)-3-oxo-1,2,3,5,6,7,8,8a-octahydro-1-naphthyl]ethyl}-4-hydroxy-3,4,5,6-tetrahydro-2H-pyran-2-one, to obtain 1.02 g of the title compound.

Nuclear Magnetic Resonance Spectrum (CDCl$_3$, 270 MHz) δ ppm: 0.86 (3H, triplet, J=7.3 Hz); 1.01 (3H, doublet, J=7.3 Hz); 1.10 (3H, doublet, J=7.3 Hz); 1.16–1.27 (1H, multiplet); 1.36–1.83 (7H, multiplet); 1.93–2.04 (1H, multiplet); 2.12–2.76 (8H, multiplet, 1H exchangeable with D$_2$O); 2.29 (3H, singlet); 2.42 (3H, singlet); 2.51 (2H, doublet, J=6.4 Hz); 3.05 (1H, doublet of doublets, J=6.8 & 16.6 Hz); 3.75–3.86 (1H, multiplet); 4.22–4.33 (1H, multiplet); 4.63 (2H, doublet, J=5.9 Hz); 4.95 (2H, singlet); 5.23–5.38 (2H, multiplet); 5.48–5.54 (1H, multiplet); 5.84–6.00 (1H, multiplet); 6.48 (1H, doublet, J=2.9 Hz).

Infrared Absorption Spectrum (CHCl$_3$) ν$_{max}$ cm$^{-1}$: 3500, 2940, 1720, 1660, 1460, 1420, 1180, 1150, 1000.

High resolution mass spectrum: Calculated for C$_{32}$H$_{46}$O$_9$N$_2$: 602.3181 (M$^+$); Found: 602.3183

PREPARATION 12

Allyl 7-[5-hexylimino-2-methyl-8-(2-methylbutyryloxy)-3-oxo-1,2,3,5,6,7,8,8a-octahydro-1-naphthyl]-3,5-dihydroxyheptanoate

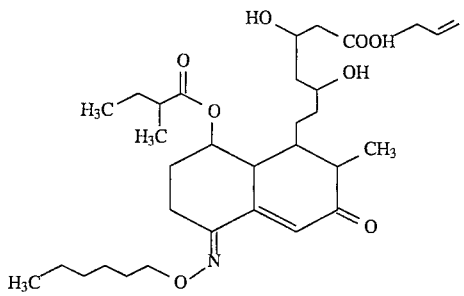

A procedure similar to that described in Preparation 1 was repeated, but using 750 mg of {2-[5-hexylimino-1-methyl-8-(2-methylbutyryloxy)-3-oxo-1,2,3,5,6,7,8,8a-octahydro-1-naphthyl]ethyl}-4-hydroxy-3,4,5,6-tetra-hydro-2H-pyran-2-one, to obtain 563 mg of the title compound.

Nuclear Magnetic Resonance Spectrum (CDCl$_3$, 270 MHz) δ ppm: 0.86 (3H, triplet, J=7.3 Hz); 0.89 (3H, doublet, J=6.8 Hz); 1.02 (3H, doublet, J=7.3 Hz); 1.11 (3H, doublet, J=6.8 Hz); 1.19–1.81 (17H, multiplet, 1H exchangeable with D$_2$O); 1.96–2.02 (1H, multiplet); 2.16–2.30 (2H, multiplet); 2.36 (1H, quartet, J=6.8 Hz); 2.46–2.55 (4H, multiplet); 3.13 (1H, doublet of doublets, J=6.4 & 16.1 Hz); 3.59 (1H, singlet, exchangeable with D$_2$O); 3.78–3.84 (2H, multiplet); 4.24–4.30 (1H, multiplet); 4.61–4.64 (2H, multiplet); 5.24–5.37 (2H, multiplet); 5.52 (1H, singlet); 5.85–5.99 (1H, multiplet); 6.53 (1H, doublet, J=2.4 Hz).

Infrared Absorption Spectrum (CHCl$_3$) $\nu_{max}$ cm$^{-1}$: 3500, 2925, 1730, 1660, 1460, 1380, 1180, 1150, 1020, 980.

High resolution mass spectrum: Calculated for C$_{32}$H$_{51}$O$_8$N$_2$: 577.3623 (M$^+$); Found: 577.3623.

PREPARATION 13

Benzyl 7-[5-(1,3-dioxan-5-yl)methoxyimino-2-methyl-8-(2-methylbutyryloxy)-3-oxo-1,2,3,5,6,7,8,8a-octahydro-1-naphthyl]-3,5-dihydroxyheptanoate

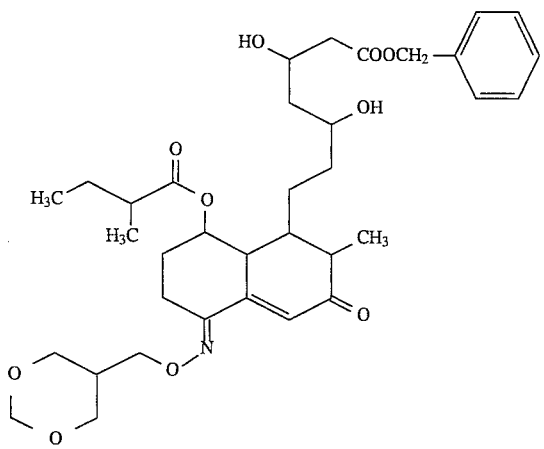

10.0 g (18.7 mmole) of 2-[5-(1,3-dioxan-5-yl)methoxyimino-2-methyl-8-(2-methylbutyryloxy)-3-oxo-1,2,3,5,6,7,8,8a-octahydro-1-naphthyl]ethyl]-4-hydroxy-3,4,5,6-tetrahydro-2H-pyran-2-one were dissolved in 230 ml of a 1:1 by volume mixture of dioxane and water. 196 ml of a 0.1N aqueous solution of sodium hydroxide were added dropwise over a period of 3.5 hours to the solution, and the resulting mixture was stirred for 1 hour at 0° C. and then for a further 1 hour at room temperature. At the end of this time, the solution was freeze-dried. The resulting sodium salt was dissolved in 110 ml of dimethylformamide, and then 6.67 ml (56.1 mmole) of benzyl bromide were added, and the mixture was stirred for 17 hours under an atmosphere of nitrogen. At the end of this time, the dimethylformamide was removed from the reaction mixture by distillation under reduced pressure. 400 ml of water were added to the residue, and then the resulting mixture was extracted with ethyl acetate (twice, each time with 300 ml). The ethyl acetate layer was washed with a saturated aqueous solution of sodium chloride, dried over anhydrous magnesium sulfate, filtered and condensed by evaporation under reduced pressure. The resulting oily residue was purified by flash column chromatography through silica gel, using a 1:2 by volume mixture of ethyl acetate and hexane as the eluent, to obtain 11.7 g of the title compound.

Nuclear Magnetic Resonance Spectrum (CDCl$_3$, 270 MHz) δ ppm: 0.88 (3H, triplet, J=7.3 Hz); 1.03 (3H, doublet, J=7.3 Hz); 1.12 (3H, doublet, J=6.6 Hz); 1.15–1.85 (11H, multiplet, 2H exchangeable with D$_2$O); 1.92–2.07 (1H, multiplet); 2.13–2.58 (4H, multiplet); 2.53 (2H, doublet, J=5.9 Hz); 3.11 (1H, doublet of doublets, J=5.9 & 15.8 Hz); 3.72–3.88 (3H, multiplet); 4.03 (2H, doublet of doublets, J=4.0 & 11.9 Hz); 4.22–4.33 (1H, multiplet); 4.27 (2H, doublet, J=7.3 Hz); 4.83 (1H, doublet, J=5.9 Hz); 4.90 (1H, doublet, J=5.9 Hz); 5.18 (2H, singlet); 5.51–5.57 (1H, multiplet); 6.51 (1H, doublet, J=2.6 Hz); 7.38 (5H, singlet).

Infrared Absorption Spectrum (CHCl$_3$) $\nu_{max}$ cm$^{-1}$: 3500, 2960, 2930, 2850, 1720, 1660, 1460, 1380, 1290, 1180, 1150, 1030, 970.

Mass spectrum m/z=518 (M$^+$ −123).

PREPARATION 14

O-Furfurylhydroxylamine hydrochloride

14(i) N-Furfuryl oxyphthal imide 43.5 g of N-hydroxyphthalimide were added to a solution of 31.1 g of furfuryl chloride in 80 ml of dimethylformamide, and the mixture was cooled to 0° C. 40.6 ml of triethylamine were then added dropwise to the mixture, after which the reaction mixture was stirred at 0° C. for 2 hours and then at room temperature for 24 hours. At the end of this time, the reaction mixture was poured into ice-water. The resulting colorless crystals were collected by filtration, to afford 53.1 g of N-furfuryloxyphthalimide, melting at 145–147° C.

14(ii) O-Furfurylhydroxylamine hydrochloride 4.28 g of [-furfuryloxyphthalimide [prepared as described in step (i) above] were dissolved in 20 ml of ethanol, and 1.37 g of butylamine were added to the resulting solution. The mixture was then stirred for 1 hour at room temperature, after which diethyl ether was added. The mixture was then acidified by the addition of a 10% by volume methanolic solution of hydrogen chloride, and the resulting crystals were collected by filtration, to afford 2.62 g of the title compound. Nuclear Magnetic Resonance Spectrum (CD₃OD, 270 MHz), δ ppm: 5.07 (2H, singlet); 6.54 (1H, doublet of doublets, J=2 & 3 Hz); 6.72 (1H, doublet, J=3 Hz); 7.67 (1H, doublet, J=2 Hz).

PREPARATION 15

O-o-Chlorobenzylhydroxylamine hydrochloride

15(i) N-o-Chlorobenzyloxyphthalimide

A procedure similar to that described in Preparation 14(i) was repeated, except that 8.10 g of o-chlorobenzyl chloride were employed, to obtain 7.63 g of N-o-chlorobenzyloxyphthalimide as colorless crystals, melting at 161°–163° C.

15(ii) O-o-Chlorobenzylhydroxylamine hydrochloride

Then following a procedure similar to that described in Preparation 14(ii), but using 2.87 g of N-o-chlorobenzyloxyphthalimide [prepared as described in step (i) above], 1.54 g of the title compound were obtained as colorless crystals, melting at 143°–145° C.

PREPARATION 16

O-(2,6-Dichlorobenzyl)hydroxylamine hydrochloride

16(i) N-(2,6-Dichlorobenzyloxy) phthalimide

A procedure similar to that described in Preparation 14(i) was repeated, except that 9.86 g of 2,6-dichlorobenzyl chloride were employed, to obtain 8.31 g of N-(2,6-dichlorobenzyloxy)phthalimide as colorless crystals, melting at 201°–206° C.

16(ii) O-(2,6-Dichlorobenzyl) hydroxylamine hydrochloride

Then following a procedure similar to that described in Preparation 14(ii), but using 3.22 g of N-(2,6-dichlorobenzyloxy)phthalimide [prepared as described in step (i) above], 2.11 g of the title compound were obtained as colorless crystals, melting at 165°–167° C.

PREPARATION 17

O-(3-Methylisoxazol-5-yl) methylhydroxylamine hydrochloride

17(i) N-(3-Methylisoxazol-5-yl)methoxyphthalimide 8.17 g of N-hydroxyphthalimide and 23.9 g of triphenylphosphine were added to a solution of 5.15 g of 5-hydroxymethyl-3-methylisoxazole in 245 ml of tetrahydrofuran. A solution of 13.3 g of dimethyl azodicarboxylate in 20 ml of tetrahydrofuran was then added dropwise at room temperature under an atmosphere of nitrogen to the resulting solution. The mixture was then allowed to stand for 30 minutes, after which the solvent was removed by distillation under reduced pressure. The resulting residue was purified by flash column chromatography through silica gel, using a 4:1 by volume mixture of hexane and ethyl acetate as the eluent, to afford 7.21 g of N-(3-methylisoxazol-5-yl)methoxyphthalimide, melting at 129°–131° C.

17(ii) O-(3-Methylisoxazol-5-yl)methylhydroxylamine hydrochloride 2.04 g of butylamine were added to a solution of 7.21 g of N-(3-methylisoxazol-5-yl)methoxyphthalimide [prepared as described in step (i) above] in 80 ml of ethanol, and the mixture was stirred for 1 hour at 60° C. At the end of this time, the temperature of the reaction mixture was lowered to room temperature, and then the reaction mixture was diluted with 300 ml of diethyl ether and acidified by the addition of a 10% by volume methanolic solution of hydrogen chloride at 0° C. The resulting crystals were collected by filtration, to afford 3.22 g of the title compound, melting at 193°–198° C.

PREPARATION 18

O-(2-Thiophenemethyl)hydroxylamine hydrochloride 20.3 ml of triethylamine and 9.0 ml of mesyl chloride were added, whilst ice-cooling and stirring, to a solution of 8.31 g of 2-thiophenemethanol in 80 ml of ethyl acetate, and the mixture was stirred for 1 hour at 0° C. and then for a further 3 hours at room temperature. At the end of this time, the reaction mixture was poured into ice-water and extracted with ethyl acetate. The extract was washed with 10% w/v aqueous hydrochloric acid, with a saturated aqueous solution of sodium hydrogencarbonate and with a saturated aqueous solution of sodium chloride, in that order. The extract was then dried over anhydrous sodium sulfate, after which the solvent was removed by distillation under reduced pressure, to afford 1.39 g of an oily residue. 1.07 g of this oily residue was dissolved in 5 ml of dimethylformamide, and then 0.91 g of N-hydroxyphthalimide was added to the resulting solution. The mixture was cooled to 0° C., and then 0.85 g of triethylamine was added, and the mixture was stirred for 2 hours at 0° C., then for 20 hours at room temperature and then for 1 hour at 60° C. At the end of this time, the reaction mixture was cooled to room temperature and diluted with water. The aqueous solution was acidified by the addition of 10% w/v aqueous hydrochloric acid, and the mixture was then extracted with ethyl acetate. The extract was washed with a 5% w/v aqueous solution of sodium hydrogencarbonate and with a saturated aqueous solution of sodium chloride, in that order, after which it was dried over anhydrous sodium sulfate. The mixture was filtered, and then the solvent was removed by distillation under reduced pressure, to afford 7.23 g of an oily residue. This oily residue was dissolved in 36 ml of dimethylformamide, and 6.14 g of N-hydroxyphthalimide were added to the resulting solution. The mixture was then ice-cooled, and 5.8 ml of triethylamine were added thereto. The reaction mixture was stirred for 15 minutes whilst ice-cooling, and was then stirred at room temperature for 17 hours. At the end of this time, the mixture was diluted with water and acidified by the addition of 10% w/v aqueous hydrochloric acid; it was then extracted with ethyl acetate. The extract was washed with a 5% w/v aqueous solution of potassium carbonate and with a saturated aqueous solution of sodium chloride, in that order, after which it was dried over anhydrous sodium sulfate and filtered. The solvent was removed from the filtrate by distillation under reduced pressure, to afford 9.87 g of N-(2-thiophenemethoxy)phthalimide. The whole of this compound was dissolved in 75 ml of ethanol, and 4.20 ml of butylamine were added to the resulting solution. The mixture was then stirred for 3 hours at 60° C. At the end of this time, the reaction mixture was cooled to room temperature and diluted with diethyl ether. It was then acidified by the addition of a 10% methanolic solution of hydrogen chloride, whilst ice-cooling. The resulting crystals were collected by filtration, to afford 5.79 g of the title compound as colorless crystals, melting at 164°–167° C.

PREPARATION 19

O-(Isoxazol-4-yl)methylhydroxylamine hydrochloride

19(i) 4-Hydroxymethylisoxazole 60 ml of a 1.0 M-hexane solution of diisobutyl-aluminum hydride were added over the course of 13 minutes and at −78° C. to a solution of 2.00 g of ethyl isoxazole-4-carboxylate in 20 ml of methylene chloride. The mixture was then stirred for 5 minutes at the same temperature, after which 4 ml of methanol were added, and the temperature of the mixture was allowed to rise to room temperature. 10 ml of methylene chloride and 3 ml of a saturated aqueous solution of sodium chloride were added to the reaction mixture, and then the mixture was filtered though a Celite (trade mark) pad. The filtrate was dried over anhydrous sodium sulfate and then the drying agent was removed by filtration. The solvent was removed by distillation under reduced pressure, to afford 781 mg of an oily residue, which was purified by distillation (120° C./7 mmHg) using a distillation bulb, to obtain 510 mg of 4-hydroxymethylisoxazole.

19(ii) N-(Isoxazol-4-yl)methoxyphthalimide

Following a procedure similar to that described in Preparation 17(i), but using 505 mg of 4-hydroxymethylisoxazole [prepared as described in step (i) above], 621 mg of N-(isoxazol-4-yl)methoxyphthalimide, melting at 133°–135° C., were obtained.

19(iii) O-(Isoxazol-4-yl)methylhydroxylamine hydrochloride

Following a procedure similar to that described in Preparation 17(ii), but using 597 mg of N-(isoxazol-4-yl)methoxyphthalimide [prepared as described in step (ii) above], 338 mg of the title compound were obtained.

Nuclear Magnetic Resonance Spectrum (CD$_3$OD, 60 MHz), δ ppm: 4.6–5.3 (2H, broad singlet); 5.1 (2H, singlet); 8.64 (1H, singlet); 9.0 (1H, singlet).

Infrared Absorption Spectrum (Nujol—trade mark) $\nu_{max}$ cm$^{-1}$: 3123, 3099, 2656, 2002, 1615, 1173, 1120, 1004.

PREPARATION 20

O-(5-Methylisoxazol-3-yl)methylhydroxylamine hydrochloride

20(i) N-(5-Methylisoxazol-3-yl)methoxyphthalimide

A procedure similar to that described in Preparation 17(i) was repeated, but using 565.6 mg of 3-hydroxymethyl-5-methylisoxazole, to obtain 1.13 g of N-(5-methylisoxazol-3-yl)methoxyphthalimide.

20(ii) O-(5-Methylisoxazol-3-yl)methylhydroxylamine hydrochloride 9.27 g of N-(5-methylisoxazol-3-yl)methoxyphthalimide [prepared as described in step (i) above] was then treated by a procedure similar to that described in Preparation 17(ii), to obtain 5.32 g of the title compound, melting at 195–196° C.

PREPARATION 21

O-(3,5-Dimethylisoxazol-4-yl)methylhydroxylamine hydrochloride

21(i) N-(3,5-Dimethylisoxazol-4-yl)methoxyphthalimide

Following a procedure similar to that described in Preparation 14(i), but using 291 mg of 4-chloromethyl-3,5-dimethylisoxazole, 362 mg of [-(3,5-dimethylisoxazol-4-yl) methoxyphthalimide, melting at 144°–146° C., were obtained.

21(ii) O-(3,5-Dimethylisoxazol-4-yl)methylhydroxylamine hydrochloride

A procedure similar to that described in Preparation 14(ii) was repeated, except that 14.8 g of N-(3,5-dimethylisoxazol-4-yl)methoxyphthalimide were employed, to obtain 8.93 g of the title compound, melting at 165°–169° C.

PREPARATION 22

Preparation of ML-236B (1) Culture

Seed culture medium:

Glycerin 30 g

Glucose 20 g

Soybean meal 20 g

Mikuni-peptone 8 g (Mikuni Chemical Industries Inc.)

Sodium nitrate 2 g

Magnesium sulfate 1 g

Tap water to 1000 ml (pH: 6.0–6.5). 50 ml of the seed culture medium having the composition described above was charged into a 500 ml Erlenmeyer flask and autoclaved at 120° C. for 30 minutes before the inoculation of the microorganism. One platinum loop from a slant of *Penicillium citrinum* Thom SANK 13380 (FERM BP-4129) was aseptically transferred into the flask containing this medium. The inoculated flask was incubated at 24° C. for 3 days on a rotary shaker at a speed of 210 rpm.

A 2000 ml Erlenmeyer flask containing 700 ml of the seed culture medium was then autoclaved at 120° C. for 30 minutes, after which it was inoculated with the whole (about 50 ml) of the fermentation broth obtained as described above. This flask was incubated for 2 days at 24° C. on a rotary shaker at a speed of 210 rpm, to prepare a second generation culture.

Production culture medium (1):

Sufficient tap water was added to 150 g of glycerin and 600 g of liquid Sanmalt (Sanwa Starch Industry, Ltd.) to adjust the total volume of the solution to 5 liters. The production culture medium (1) was then sterilized by autoclaving for 30 minutes at 120° C.

Production culture medium (2):

The following components were mixed:

Soybean meal 300 g

Mikuni-peptone 150 g (Mikuni Chemical Industries Co.)

Honen CSL 300 g (Honen Corporation)

Gluten meal 150 g (Nihon Food Processing Co.).

Magnesium sulfate 15 g

The pH was adjusted to a value of 6.0–6.5 by the addition of a 10% w/v aqueous solution of sodium hydroxide, and then the total volume was adjusted to 10 liters by the addition of tap water. The production culture medium (2) was then sterilized by autoclaving for 30 minutes at 120° C.

Feed liquor A:

Tap water was added to a mixture of 1600 g of glycerin and 6400 g of Sanmalt S (Sanwa Starch Industry, Ltd.), and then the mixture was heated to above 90° C. After the Sanmalt S had completely dissolved, tap water was added to the solution to make a total volume of 10 liters. The solution was then autoclaved at 120° C. for 30 minutes.

Feed liquor B:

600 ml of Sannicks PP 2000 (Sanyo Chemical Industries Co., Ltd.) medium were autoclaved at 120° C. for 30 minutes.

After autoclaving, 5 liters of production culture medium (1) and 10 liters of production culture medium (2) were charged into a stainless-steel 30 liter jar fermentor.

The whole contents of an Erlenmeyer flask (about 700 ml) containing the second generation culture prepared as described above was then used to inoculate the autoclaved production culture medium in the jar fermentor. The fermentor was incubated at 24° C. with stirring at an automatically controlled range of 260 to 500 rpm, whilst aerating at an air flow of 7.5 liters per minute and at a pressure of 0.5 $kg/cm^2$ such as to maintain a dissolved oxygen concentration of from 3 to 5 ppm.

During the period from the third to the sixth day after commencement of the incubation, 150 ml of Feed liquor B were added to the culture medium once per day (a total of 4 times). After the concentration of reducing sugar was estimated to be no more than 1%, Feed liquor A was continuously added in order to ensure that the pH of the broth was kept at a value of about pH 4.

After 14 days, the resulting broth was harvested.

(2) Isolation

The pH of the culture broth (40 liters) was adjusted to a value of 12 by the addition of 800 ml of a 6N aqueous solution of sodium hydroxide, and the resulting mixture was stirred for 60 minutes at room temperature. At the end of this time, the broth was mixed with 1.5 kg of a Celite filter aid (Celite #545, a trade mark for a product of Johns-Manville Products Corp.), and the mixture was stirred. The resulting mixture was filtered through a filter press to produce a filtrate.

850 ml of 6N aqueous hydrochloric acid were carefully added to the filtrate, and the pH of the mixture was adjusted to a value of 5.0. 80 liters of ethyl acetate were added to the resulting solution, and the mixture was stirred to extract the desired product. The organic layer was separated and the aqueous layer was treated with 40 liters of ethyl acetate and stirred to extract the desired product. The combined ethyl acetate extracts were then extracted with 10 liters of a 3% w/v aqueous solution of sodium hydrogencarbonate. The aqueous layer was separated and the organic layer was again extracted with a 3% w/v aqueous solution of sodium hydrogencarbonate.

1600 ml of 6N aqueous hydrochloric acid were carefully added to the combined aqueous extracts, and the pH of the mixture was adjusted to a value of 5.0. 20 liters of ethyl acetate were added to the resulting mixture, and the mixture was stirred to extract the desired product. The organic layer was separated and the aqueous layer was treated with 10 liters of ethyl acetate and stirred to extract the desired product. The combined ethyl acetate extracts were washed with 15 liters of a 10% w/v aqueous solution of sodium chloride. The extract was then dried over 3000 g of anhydrous sodium sulfate, and the solvent was removed by evaporation to dryness under reduced pressure, using a rotary evaporator to afford an oily residue.

This oily residue was dissolved in 1000 ml of ethyl acetate. 0.5 ml of trifluoroacetic acid was added to the solution, and the mixture was heated under reflux for 30 minutes in a vessel fitted with a reflux condenser. The contents were cooled to 10° C., and then washed twice, each time with 500 ml of a 3% w/v aqueous solution of sodium hydrogencarbonate, and once with 500 ml of a 10% w/v aqueous solution of sodium chloride, in that order. The organic layer was dried over 100 g of anhydrous sodium sulfate and filtered. The filtrate was freed from the solvent by evaporation to dryness under reduced pressure, using a rotary evaporator, to afford 50 g of an oily residue.

The whole of this oily residue was dissolved in 500 ml of acetonitrile, and the resulting solution was divided into five parts. Each part was purified by chromatography through an ODS reverse phase column [ODS-1050-20SR, 10 cm (internal diameter)×50 cm, 15–30 μm (particle size); Kurita Kogyo Co., Ltd.]. The column was eluted with 70% by volume aqueous acetonitrile, used as the mobile phase, at a flow rate of 200 ml/minute. The fractions recovered from the column were monitored by ultraviolet absorption and, on the basis of the peaks thus detected, those fractions having retention times between 30 and 36 minutes were collected.

The purity of these fractions was assessed by high speed liquid chromatography through a column (ODS-262, Senshu Kagaku Co., Ltd.) using 70% by volume aqueous acetonitrile as the mobile phase at flow rate of 1.0 ml/minute, whilst monitoring the fractions by ultraviolet absorption at 236 nm. A fraction having a retention time of 11 minutes showed a single peak of characteristic ultraviolet absorption.

Those fractions having a retention time between 30 and 36 minutes from the reverse phase column chromatography were concentrated by distillation under reduced pressure, using a rotary evaporator to distill off the acetonitrile. The concentrate was twice extracted with one half its volume of ethyl acetate. The ethyl acetate extracts were combined and concentrated by evaporation to dryness under reduced pressure, to afford 30 g of oily residue.

The oil was triturated with a mixture of ethanol and water to induce crystallization. 17 g of the title compound were obtained as colorless crystals.

The physico-chemical properties of this compound are known and are identical with those described in Japanese Patent Publication No. Sho 56-12114 (=GB Patent No. 453425) and other literature.

PREPARATION 23

Preparation of the sodium salt of M-4

Yeast MY culture medium:

Yeast extract (Difco) 0.3% (w/v).

Malt extract (Difco) 0.3% (w/v)

Polypeptone 0.5% (w/v) (Daigo Nutrition Chemicals Co.)

Glucose 1.0% (w/v)

Tap water balance (pH: not adjusted).

A 500 ml Erlenmeyer flask containing 100 ml of the above yeast MY culture medium was inoculated with a platinum loop from a slant of *Amycolata autotrophica* SANK 62981 (FERM BP-4105). The flask was incubated at 28° C. on a rotary shaker at a speed of 200 rpm.

After 3 days, twenty 500 ml Erlenmeyer flasks each containing 100 ml of the yeast MY culture medium were each inoculated with 5 ml of the flask contents of the seed culture. The cultures were then incubated at 28° C. on a rotary shaker at a speed of 200 rpm. After 2 days, an aqueous solution of the sodium salt of ML-236B was added to a final concentration of 0.1% of the sodium salt, and the mixture was incubated at 28° C. on a rotary shaker at a speed of 200 rpm for 5 days.

At the end of this time, the fermentation broth was filtered, and the filtrate was absorbed on 200 ml of a non-ionic resin, Diaion HP-20 (trade mark). The resin was washed with 300 ml of distilled water and the fractions containing the title compound were eluted with 800 ml of 50% v/v aqueous acetone.

The eluate was concentrated by evaporation to dryness under reduced pressure, and the concentrate was purified by chromatography through a preparative ODS column (ODS-H-5251) using a 480:520:1 by volume mixture of acetonitrile, water and acetic acid as the eluent, whilst monitoring the fractions by ultraviolet absorption at 237 nm. The desired fractions were collected, and their pH was adjusted to a value of 8.0 by the addition of an aqueous solution of sodium hydroxide. The mixture was then concentrated by evaporation under reduced pressure. The concentrate was dissolved in water, and the resulting aqueous solution was treated with 50 ml of Diaion HP-20. The resin was washed with 100 ml of distilled water and then eluted with 200 ml of 50% v/v aqueous acetone, to afford 618 mg of the title compound.

The physico-chemical properties are known and are identical with those described in Japanese Patent Publication No. Sho 61-13699 (=GB Patent No. 2077264) and other literature.

We claim:

1. A pharmaceutically acceptable salt of 7-[5-(1,3-dioxan-5-yl)methoxyimino-2-methyl-8-(2-methylbutyryloxy)-3-oxo-1,2,3,5,6,7,8,8a-octahydro-1-naphthyl]-3-hydroxy-5-oxoheptanoic acid.

2. A pharmaceutical composition comprising an active compound for inhibiting cholesterol biosynthesis in admixture with a pharmaceutically acceptable carrier or diluent, wherein said active compound is as claimed in claim 1.

3. A method of treating a mammal suffering from a disorder arising from a blood cholesterol imbalance, which comprises administering to said mammal an effective amount of an active compound inhibiting cholesterol biosynthesis, wherein said active compound is as claimed in claim 1.

4. The pharmaceutically acceptable salt of claim 1, wherein the salt is selected from the group consisting of a metal salt, an amino acid salt and an amine salt.

5. The pharmaceutically acceptable salt of claim 1, wherein the salt is selected from the group consisting of an alkali metal salt and an alkaline earth metal salt.

6. The pharmaceutically acceptable salt of claim 1, wherein the salt is selected from the group consisting of a sodium salt, a potassium salt, a calcium salt, a magnesium salt, an aluminum salt, an iron salt, a zinc salt, a copper salt, a nickel salt, a cobalt salt, an arginine salt, a lysine salt, a histidine salt, an α,γ-diaminobutyric acid salt, an ornithine salt, a t-octylamine salt, a dibenzylamine salt, a dicyclohexylamine salt, a morpholine salt, a D-phenylglycine alkyl ester salt and D-glucosamine salt.

7. The pharmaceutically acceptable salt of claim 6, wherein the salt is selected from the group consisting of a sodium salt, a potassium salt, a calcium salt and an aluminum salt.

8. The pharmaceutically acceptable salt of claim 6, wherein the salt is selected from the group consisting of a sodium salt, a potassium salt and a calcium salt.

9. The pharmaceutically acceptable salt of claim 6, wherein the salt is a sodium salt.

* * * * *